(12) United States Patent
Ouyang et al.

(10) Patent No.: US 8,592,564 B2
(45) Date of Patent: Nov. 26, 2013

(54) IMMUNOASSAYS FOR LAMOTRIGINE

(75) Inventors: Anlong Ouyang, Fremont, CA (US);
Lili Arabshahi, Fremont, CA (US);
Mark Roberts, Carmel, IN (US);
Melissa Wall, Avon, IN (US)

(73) Assignee: Seradyn, Inc., Indianapolis, IN (US)

( * ) Notice: Subject to any disclaimer, the term of this patent is extended or adjusted under 35 U.S.C. 154(b) by 441 days.

(21) Appl. No.: 12/693,341

(22) Filed: Jan. 25, 2010

(65) Prior Publication Data
US 2010/0209416 A1 Aug. 19, 2010

Related U.S. Application Data

(62) Division of application No. 11/254,637, filed on Oct. 20, 2005, now Pat. No. 7,678,551.

(60) Provisional application No. 60/621,764, filed on Oct. 25, 2004.

(51) Int. Cl.
*C07K 16/00* (2006.01)
*C07K 1/04* (2006.01)
*C07K 1/13* (2006.01)

(52) U.S. Cl.
USPC .................. 530/389.8; 530/388.9; 530/403; 530/405; 424/175.1

(58) Field of Classification Search
None
See application file for complete search history.

(56) References Cited

U.S. PATENT DOCUMENTS

| | | | |
|---|---|---|---|
| 4,492,762 A | 1/1985 | Wang | |
| 4,593,089 A | 6/1986 | Wang | |
| 4,668,640 A | 5/1987 | Wang | |
| 4,708,929 A | 11/1987 | Henderson | |
| 4,751,190 A | 6/1988 | Chiapetta | |
| 4,847,209 A | 7/1989 | Lewis | |
| 5,120,653 A | 6/1992 | Henderson | |
| 5,571,728 A | 11/1996 | Kraus | |
| 5,604,091 A | 2/1997 | Henderson | |
| 5,643,734 A | 7/1997 | Henderson | |
| 5,798,083 A | 8/1998 | Massey | |
| 5,834,206 A | 11/1998 | Neuenhofer | |
| 6,232,082 B1 | 5/2001 | Ennifar | |
| 6,248,597 B1 | 6/2001 | Eda | |
| 6,333,198 B1 | 12/2001 | Edmeades | |
| 6,448,091 B1 | 9/2002 | Massey | |
| 6,514,770 B1 | 2/2003 | Sorin | |
| 7,026,134 B2 | 4/2006 | Lamont | |
| 2003/0099636 A1 | 5/2003 | Epshtein | |
| 2006/0115865 A1 | 6/2006 | Ouyang | |

OTHER PUBLICATIONS

Chappey et al. Monoclonal antibodies in Hapten Immunoassays. Pharmaceutical Research 1992, vol. 9, No. 11, pp. 1375-1379.*

(Continued)

*Primary Examiner* — Shafiqul Haq
(74) *Attorney, Agent, or Firm* — Workman Nydegger

(57) ABSTRACT

Generally, the present invention relates to lamotrigine analogs that have substituents at the triazine 3-position and on the benzene 4-position and 5-position. The lamotrigine analogs can include immunogenic moieties that can be used to prepare anti-lamotrigine antibodies, or antigenic moieties that can be used in immunodiagnostic assays for lamotrigine. Also, the lamotrigine analog can include tracer moieties for detecting the presence or amount of the analog during an immunodiagnostic assay. Additionally, the lamotrigine analogs can be used in immunodiagnostic assays to compete with lamotrigine for binding with anti-lamotrigine antibodies.

10 Claims, 20 Drawing Sheets

(56) References Cited

OTHER PUBLICATIONS

Tuomola et al., Production and characterisation of monoclonal antibodies against a very small hapten, 3-methylinodole. Journal of Immunological Methods 2000, vol. 24, pp. 111-124.

Bidlecombe, R.A. et al., "Validation of a Dadioimmunoassay for the Determination of Human Plasma Concentrations of Lamotrigine," Journal of Pharmaceutical and Biochemical Analysis, New York, NY, US, vol. 8, No. 8/12, Jan. 1, 1990, pp. 691-694.

Ballesteros et al., Influence of the Hapten Design on the Development of a Cmpetitive ELISA for the Determination of the Antifouling Agent Irgarol 1051 at Trace Label. 1998, Anal. Chem. vol. 70, pp. 4004-4014.

Marco et al., Hapten Design and Development of an ELISA (Enzyme-linked Immunosorbent Assay) for the Detection of the Mercapturic Acid Conjugates of Naphthalene, 1998, J. Org. Chem. vol. 58, pp. 7548-7556.

Croci, Danilo, et al.; "New High-Performance Liquid Chromatographic Method for Plasma/Serum Analysis of Lamotrigine," *Therapeutic Drug Monitoring*, 23: 665-668; received Mar. 20, 2001; accepted Jul. 2, 2001.

Morris, Raymond G., et al.; "Lamotrigine and Therapeutic Drug Monitoring: Retrospective Survey Following the Introduction of a Routine Service," *Br J Clin Pharmocol*, 1998; 46: 547-551.

Lensmeyer, Gary L., et al.; "Optimized High-Performance Liquid Chromatographic Method for Determination of Lamotrigine in Serum with Con Comitant Determination of Phenytoin, Carbamazipine, and Carbamazepine Epoxide," *Therapeutic Drug Monitoring*, 196/21/2011292-300, 1997; received Jul. 5, 1996; accepted Oct. 17, 1996.

Fraser, Albert D., "Lamotrigine Analysis in Serum by High-Performance Liquid Chromatography," *Therapeutic Drug Monitoring*, 17:174-178, 1995; received Aug. 11, 1994, accepted Oct. 10, 1994.

Sailstad, Jeffrey M., "Immunofluorometric Assay for Lamotrigine (Lamictal) in Human Plasma," *Therapeutic Drug Monitoring*, 13:243-300, 1991 received Dec. 4, 1990; accepted May 3, 1991.

European Search Report from EPO Patent Application No. EP05812520, dated Dec. 23, 2008, 13 pages.

U.S. Appl. No. 11/254,637, mailed Mar. 26, 2007, Office Action.
U.S. Appl. No. 11/254,637, mailed Oct. 9, 2007, Office Action.
U.S. Appl. No. 11/254,637, mailed Mar. 26, 2008, Office Action.
U.S. Appl. No. 11/254,650, mailed Jun. 25, 2008, Office Action.
U.S. Appl. No. 11/254,637, mailed Oct. 2, 2008, Office Action.
U.S. Appl. No. 11/254,637, mailed Apr. 29, 2009, Office Action.
U.S. Appl. No. 11/254,637, mailed Oct. 28, 2009, Notice of Allowance.

* cited by examiner

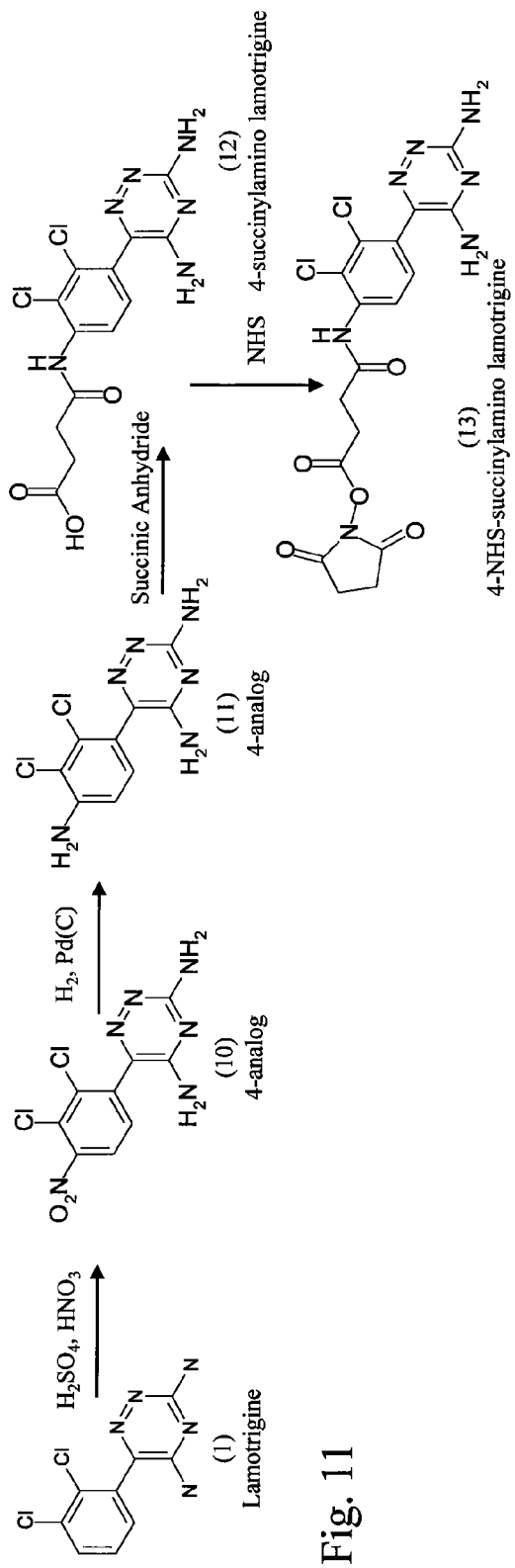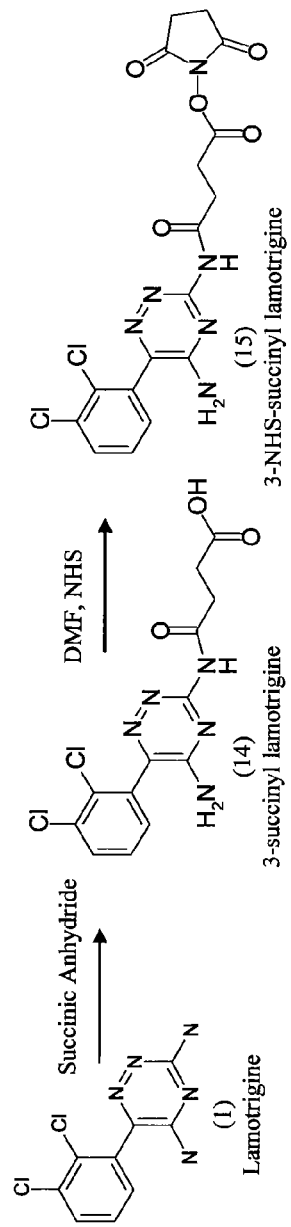
Fig. 11
Fig. 12

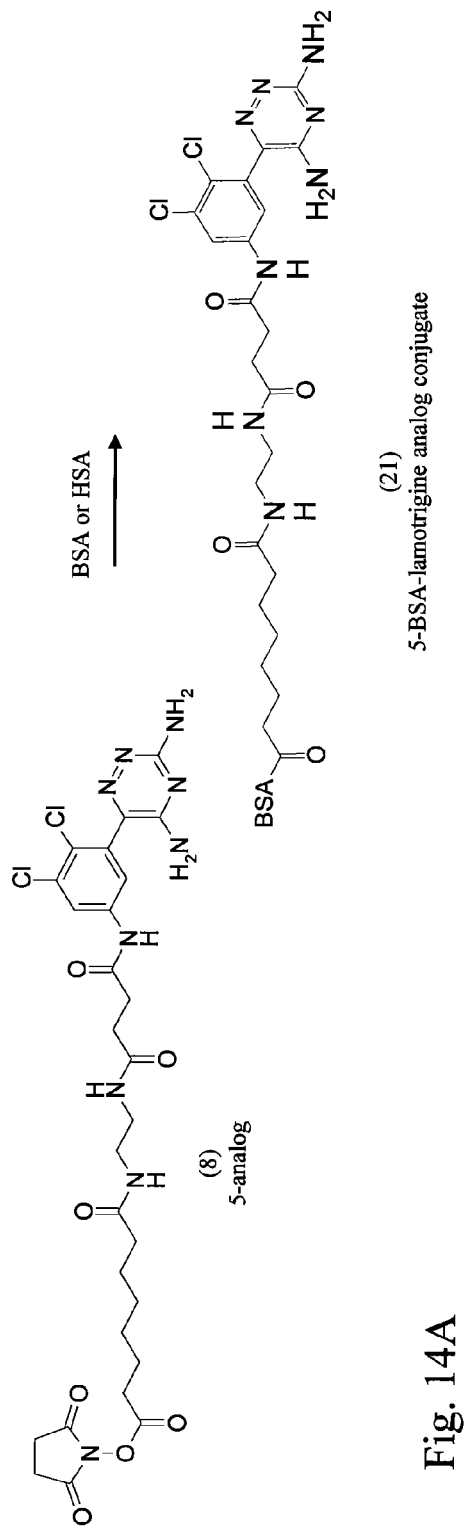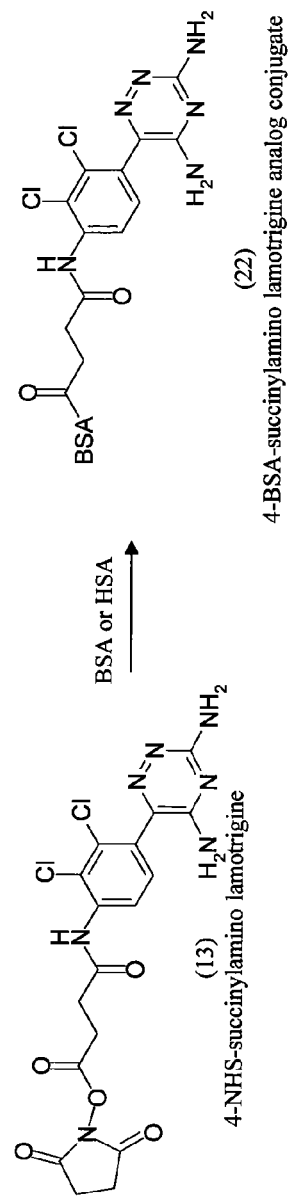
Fig. 14A
Fig. 14B

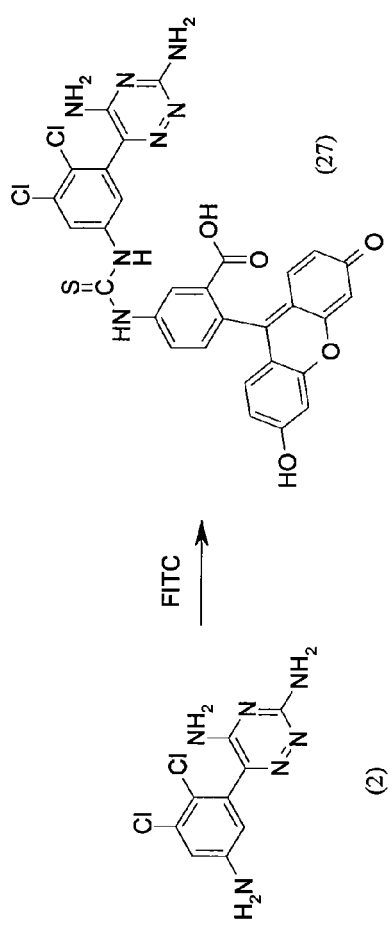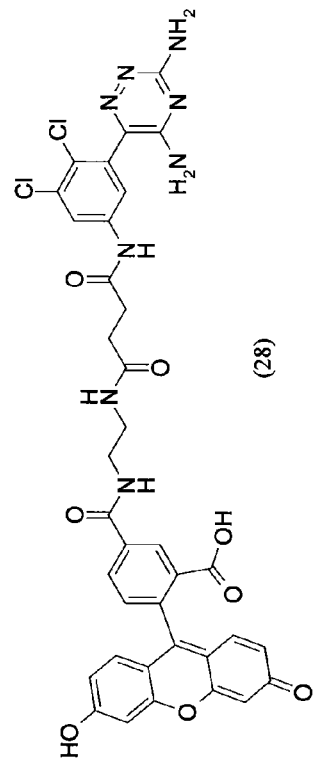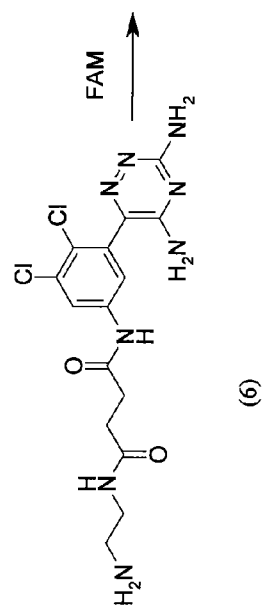
Fig. 16A
Fig. 16B

IMMUNOASSAYS FOR LAMOTRIGINE

CROSS-REFERENCE TO RELATED APPLICATIONS

This U.S. patent application is a divisional of U.S. patent application having Ser. No. 11/254,637 filed on Oct. 20, 2005 now U.S. Pat. No. 7,678,551 with Anlong Ouyang, Ph.D. et al. as inventors and entitled, "IMMUNOASSAYS FOR LAMOTRIGINE," which claims the benefit of U.S. Provisional Application having Ser. No. 60/621,764, entitled, "IMMUNOASSAYS FOR LAMOTRIGINE," which was filed on Oct. 25, 2004, with Anlong Ouyang, Ph.D. et al. as inventors, the entireties of which are incorporated herein by reference.

BACKGROUND OF THE INVENTION

1. The Field of the Invention

The present invention relates to lamotrigine immunodiagnostic reagents and protocols. More particularly, the present invention relates to lamotrigine, lamotrigine analogs, immunogens and antigens prepared from lamotrigine analogs, antibodies prepared from lamotrigine-based immunogens, and methods of making and using the same.

2. The Related Technology

Lamotrigine, chemically represented as 3,5-diamino-6-(2,3-dichlorophenyl)-1,2,4-triazine and shown below, is an anti-epileptic drug ("AED") of the phenyltriazine class, and is chemically unrelated to existing AEDs. Lamotrigine is the active ingredient in LAMICTAL® (Glaxo Wellcome), an FDA-approved drug used for anti-epileptic treatment as well as for treatment of the psychiatric disorders, such as bipolar disease.

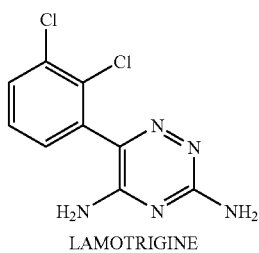 [SMILES: Nc1nnc(-c2cccc(Cl)c2Cl)c(N)n1]

LAMOTRIGINE

Epilepsy is brain function disorder that results in repeated seizures. Lamotrigine has been shown to have a broad spectrum of clinical efficacy, and is effective in treating and/or preventing partial seizures, primary and secondarily generalized seizures, absence seizures, and drop attacks associated with Lennox-Gastaut syndrome.

It is well known that various drugs such as AEDs, can have different pharmacokinetic and/or pharmacodynamic profiles in different patient populations, which results in the therapeutic drug monitoring ("TDM") of AEDs to be vitally important. One goal of a TDM program is to optimize a patient's clinical outcome by managing and/or optimizing a medication regimen with the assistance of determining drug concentrations at various times. Accordingly, the drug dose and regimen can be modulated for a single patient or patient population based on TDM.

Several characteristics of lamotrigine suggest there is a clinical need to individualize patient therapy by use of TDM. It has been suggested that there are large inter-individual variations in dose versus serum concentrations in patients, and pharmacokinetic variability plays a major role in the lamotrigine dosage requirements needed to achieve optimum serum concentrations.

It as been suggested that an appropriate range of optimal serum concentrations for lamotrigine would be 12 to 55 µmol/L in patients with refractory epilepsy. See Morris R G et al, *Br J Clin Pharmacol;* 46:547-51 (1998). In the responders (>50% seizure reduction), the median lamotrigine concentration was 31 µmol/L (range, 8-60 µmol/L) compared with 62 µmol/L (range, 31-60 µmol/L) in patients with side effects. As such, a target range of 10 to 60 µmol/L (2.54-15.24 µg/mL) is now suggested for lamotrigine. Thus, effective TDM can be used to predict dosing regimens that can obtain appropriate lamotrigine concentrations within the therapeutic index.

Many methods have been described for analyzing lamotrigine. Primarily, the methods include HPLC with ultraviolet ("UV") detection. See, Fraser et al, *Ther Drug Monitoring,* 17:174-178, 1995; Lensmeyer et al, *Ther Drug Monitoring,* 19:292-300, 1997; Croci et al. *Ther Drug Monitoring* 23:665-668, 2001. In addition, a competitive binding enzyme immunoassay (ELISA) for the measurement of lamotrigine in sera has been reported. See, Sailstad et al, *Ther Drug Monitoring,* 13:433-442, 1991. However, such methods are impractical for commercial use due to, for example, long sample preparation time, long assay time, high cost, and labor-intensive procedures. Thus, a simple and fast analytical method for measuring lamotrigine plasma levels is needed for effective TDM, which immunoassay techniques are well suited for such analytical applications.

Immunoassay techniques have been developed to detect various drugs in biological samples and are well suited for such commercial analytical applications. Accordingly, immunoassays can be used to quickly assess the amount of a drug and/or drug metabolite in a patient's blood. Examples of immunoassays can include, but not limited to, homogeneous microparticle immunoassay (e.g., immunoturbidimetric) or quantitative microsphere system ("QMS®"), fluorescence polarization immunoassay ("FPIA"), cloned enzyme donor immunoassay ("CEDIA"), chemiluminescent microparticle immunoassay ("CMIA"), and the like.

Accordingly, it would be advantageous to have immunoassays configured to detect lamotrigine in a patient's blood, serum, plasma, and/or other biological fluids or samples. Additionally, it would be advantageous to have lamotrigine analogs for use in such immunoassays, and/or lamotrigine analog-based immunogens for use in producing anti-lamotrigine antibodies.

BRIEF SUMMARY OF THE INVENTION

Generally, the present invention relates to lamotrigine analogs and immunodiagnostic assays for lamotrigine. The lamotrigine analogs can include operative groups, such as: immunogenic moieties that can be used to prepare anti-lamotrigine antibodies; antigenic moieties that can be used in immunodiagnostic assays for lamotrigine; or tracer moieties that can be used in immunodiagnostic assays. Additionally, the lamotrigine analogs can be used in immunodiagnostic assays to compete with lamotrigine for anti-lamotrigine antibodies.

In one embodiment of the present invention, a lamotrigine analog can include a chemical structure of at least one of Formula 1A, Formula 2A, or Formula 3 A.

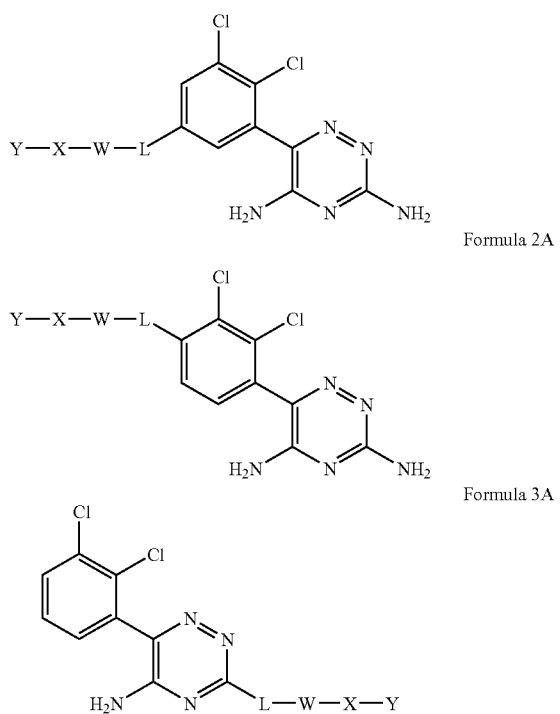

Formula 1A

Formula 2A

Formula 3A

Additionally, the foregoing chemical structures of Formula 1A, Formula 2A, and/or Formula 3A are scaffolds that can include a variety of moieties conjugated thereto. As such, the scaffolds can be further defined by the following: (a) L can be one of the group NH, NHCO, or O; (b) W can be a saturated or unsaturated, substituted or unsubstituted, and straight or branched chain of 1-10 carbon or hetero chain atoms; (c) X can be at least one of a bond between W and Y, a substituted or unsubstituted aromatic or aliphatic group having from 1-2 rings, and/or a saturated or unsaturated, substituted or unsubstituted, or straight or branched chain having 1-10 carbon or hetero chain atoms; (d) Y is selected from the group consisting of aliphatic, alcohol, amine, amide, carboxylic acid, aldehyde, ester, activated ester, aliphatic ester, imidoester, isocyanate, isothiocyanate, anhydride, thiol, alcohol, thiolactone, diazonium, and maleimido groups; and (e) Y—X—W-L- of Formula 1 is not a 5-succinylamino moiety. Additionally, Y can be a linker group coupled to an operative group.

In one embodiment, a lamotrigine analog in accordance with any of the scaffolds depicted by formulas 1A, 2A, and/or 3A can be characterized by being coupled to an immunogenic moiety via appropriate chemistry, to form an immunogen that generates an antibody at a titer sufficient for use in an immunodiagnostic assay for lamotrigine. Also, it is possible for the lamotrigine analog to be coupled to an immunogenic moiety to form an immunogen that generates an antibody that interacts with the antigen and lamotrigine wherein the affinity, specificity, and/or avidity is substantially similar for lamotrigine and the analog and can be used in competitive binding studies. Additionally, the lamotrigine analog can be coupled to a tracer moiety and have sufficient solubility for use in an immunodiagnostic assay. The analog can also be coupled to an antigen moiety and have sufficient solubility for use in an immunodiagnostic assay. Further, the lamotrigine analog can be stably loaded onto a particle or microparticle. Furthermore, the lamotrigine analog can be coupled to an enzyme, enzyme donor, or enzyme acceptor.

One embodiment of the present invention includes an antibody composition for use in an immunodiagnostic system for detecting the presence of lamotrigine in a sample. The antibody composition can include an anti-lamotrigine antibody having at least one binding domain, wherein the antibody is capable of binding lamotrigine and is capable of binding a lamotrigine analog. Also, the antibody can be present in a titer of at least about 1:5,000, more preferably at least about 1:10,000, even more preferably at least about 1:50,000, still more preferably at least about 1:100,000, and most preferably at least about 1:300,000. In some instances it can be preferably to have an antibody titer as low as 1:5,000 or as high as 1:300,000.

Additionally, the antibody is a monoclonal antibody and/or a polyclonal antibody. The antibody can have at least one of affinity, specificity, or avidity for a lamotrigine analog compared to lamotrigine that is sufficient for use in a homogeneous or heterogeneous immunodiagnostic assay. As such, the interaction between the antibody and the lamotrigine analog can be at least 50% of at least one of affinity, specificity, or avidity of the antibody for lamotrigine, even more preferably at least 70% of at least one of affinity, specificity, or avidity of the antibody for lamotrigine, most preferably at least 90% of at least one of affinity, specificity, or avidity of the antibody for lamotrigine. Optionally, at least one of affinity, specificity, or avidity of the antibody for a lamotrigine analog is substantially the same as for lamotrigine.

In one embodiment, the present invention includes a system for use in an immunodiagnostic system for detecting the presence of lamotrigine in a sample. Such a system can include the lamotrigine analog and the anti-lamotrigine antibody. In one aspect, the lamotrigine analog includes a linker substituent coupled to an end group selected from the group consisting of saturated or unsaturated aliphatics, alcohols, amines, amides, carboxylic acids, aldehydes, esters, activated esters, aliphatic esters, imidoesters, isocyanates, isothiocyanates, anhydrides, thiols, alcohols, thiolactones, diazonium groups, and maleimido groups. In the system, the linker substituent can be characterized by at least one of the following: (a) a 5-position substituent having at least a 5 carbon or hetero atom aliphatic chain; (b) a 4-position substituent having at least at least a 4 carbon or hetero atom aliphatic chain; or (c) a 3-position substituent having at least a 4 carbon or hetero atom aliphatic chain. Additionally, one of the lamotrigine analog or anti-lamotrigine antibody can be coupled with one of a particle, magnetic particle, microparticle, microsphere, support, enzyme donor, or enzyme acceptor.

In one embodiment, the system can include at least one of the following: (a) a stock composition of lamotrigine; (b) a series of compositions containing lamotrigine at different concentrations, the series of compositions forming a concentration gradient; (c) the lamotrigine analog having a tracer moiety; (d) the lamotrigine analog coupled to a microparticle; (e) the antibody coupled to a microparticle; (f) the lamotrigine analog having an enzyme donor and a corresponding enzyme acceptor; (g) the lamotrigine analog having to an enzyme acceptor and a corresponding enzyme donor; or (h) the antibody loaded on a particle suitable for separation by filtration or sedimentation.

The present invention also includes methods of performing immunodiagnostic assays for detecting the presence of lamotrigine in a sample. Such methods can include combining an anti-lamotrigine antibody at a titer of at least 1:5,000 and a lamotrigine analog with a sample obtained from a subject previously administered lamotrigine to form a first composition. Any free lamotrigine from the sample and the lamotrigine analog are then allowed to compete for binding with the antibody. After the competitive binding, the binding between the lamotrigine analog and the antibody is detected.

In one embodiment, the immunodiagnostic assay utilizes a lamotrigine analog including a fluorescent moiety, and is combined with the antibody and sample as described. The fluorescent moiety can be excited with polarized light having a first amount of polarization, and the polarized light emitted from the fluorescent moiety having a second amount of polarization is detected. Optionally, the first amount of polarization is compared with the second amount of polarization, and a determination is made as to whether lamotrigine is present in the sample, wherein the second amount of polarization being different from the first amount of polarization is an indication that lamotrigine is present in the sample. Additionally, the immunodiagnostic assay can include a control by combining a known amount of lamotrigine with the lamotrigine analog and antibody to form a control binding composition. The polarized light emitted from the florescent conjugate in the control binding composition having a third amount of polarization is detected, and compared with the second amount of polarization. The amount of lamotrigine present in the sample is then determined.

In one embodiment, an immunodiagnostic assay uses a lamotrigine analog or antibody loaded onto a microparticle. The analog, antibody, and sample are combined into a first composition, where any free lamotrigine competes with the analog for binding with the antibody. The first composition is then irradiated with incident light, and a first intensity of light transmitted from the first composition is detected. The minimum intensity of light transmitted from a control binding composition having the lamotrigine analog and antibody and not having free lamotrigine is identified and compared with the first intensity of the transmitted light. A determination is made as to whether lamotrigine is present in the sample, wherein the minimum intensity being different from the first intensity is an indication that lamotrigine is present in the sample. Additionally, the immunodiagnostic assay can include a control by combining a known amount of lamotrigine with the lamotrigine analog and antibody to form a control binding composition. The control binding composition is then irradiated with incident light, and a second intensity of light transmitted from the control binding composition is detected. The amount of lamotrigine present in the sample can then be determined, wherein a comparison between the first intensity and the second intensity is an indication of the amount of lamotrigine present in the sample.

In one embodiment, an immunodiagnostic assay uses a lamotrigine analog having an enzyme donor. The analog, antibody, and sample are combined into a first composition, where any free lamotrigine competes with the analog for binding with the antibody. An enzyme acceptor and substrate are then combined with the first composition, wherein the substrate is cleavable by interacting with the enzyme donor and enzyme acceptor. The enzyme activity is then detected. Additionally, the immunodiagnostic assay can include a control by combining a known amount of lamotrigine with the lamotrigine analog and antibody to form a control binding composition, and the enzyme acceptor and substrate are then combined therewith. The amount of lamotrigine present in the sample is determined by a comparison between the enzyme activity and the control enzyme activity providing an indication of the amount of lamotrigine present in the sample.

In one embodiment, an immunodiagnostic assay uses a lamotrigine analog that includes a tracer conjugate. The analog, antibody, and sample are combined into a first composition, where any free lamotrigine competes with the analog for binding with the antibody. The antibody is then separated from the first composition, and any unbound lamotrigine analog is separated from the antibody. The tracer conjugate bound with the antibody from the competitive binding composition is then detected. Additionally, the immunodiagnostic assay can include a control by combining a known amount of lamotrigine with the lamotrigine analog and antibody to form a control binding composition. Accordingly, the amount of lamotrigine present in the sample can be determined by a comparison between the amount of tracer conjugate in the first composition and the amount of tracer conjugate in the control binding composition in order to provide an indication of the amount of lamotrigine present in the sample.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 11 is a schematic diagram illustrating an embodiment of a synthesis protocol for synthesizing a lamotrigine analog;

FIG. 12 is a schematic diagram illustrating an embodiment of a synthesis protocol for synthesizing a lamotrigine analog;

FIGS. 14A-14D are schematic diagrams illustrating embodiments of synthesis protocols for synthesizing a lamotrigine-based antigens;

FIGS. 16A-16B are schematic diagrams illustrating embodiments of synthesis protocols for synthesizing lamotrigine-based fluorescent tracers;

DETAILED DESCRIPTION OF THE PREFERRED EMBODIMENTS

Figure 1:
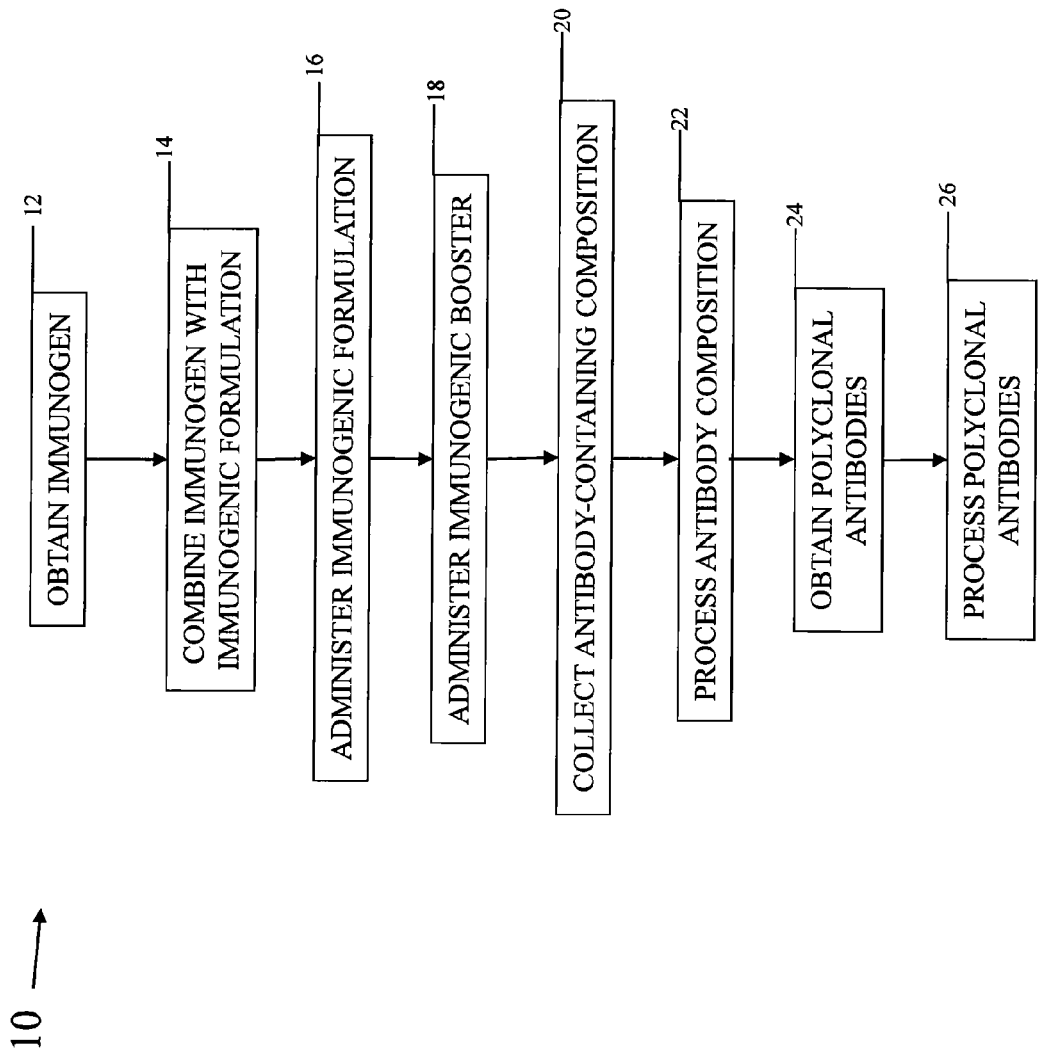
FIG. 1 is a flow diagram illustrating an embodiment of a method for preparing an anti-lamotrigine antibody.

Generally, the present invention relates to lamotrigine analogs and immunodiagnostic assays for lamotrigine. The lamotrigine analogs can include immunogenic moieties that can be used to prepare anti-lamotrigine antibodies, or antigenic moieties or tracer moieties that can be used in immunodiagnostic assays for lamotrigine. Additionally, the lamotrigine analogs can be used in immunodiagnostic assays to compete with lamotrigine for anti-lamotrigine antibodies. As such, the following terminology is meant to describe embodiments of the invention, and is not intended to be limiting.

As used herein, the term "hapten" is meant to refer to a partial or incomplete antigen, and can be a small molecule or drug. Also, a hapten can be a low molecular weight molecule that is a protein-free or polypeptide-free substance. Usually, a hapten is not capable of stimulating antibody formation alone, but can be capable of interacting with antibodies. Accordingly, lamotrigine and lamotrigine analogs in accordance with the present invention can be haptens.

As used herein, the term "analog" or "derivative" is meant to refer to a chemical compound or molecule made from a parent compound or molecule by one or more chemical reactions. As such, an analog can be a compound with a structure similar to that of lamotrigine or based on a lamotrigine scaffold, but differing from it in respect to certain components or structural makeup, which may have a similar or opposite action metabolically. An analog or derivative of lamotrigine in accordance with the present invention can be used to compete for binding with an antibody that recognize both the analog and lamotrigine. Also, an analog can include an operative group coupled to lamotrigine through a linker group.

As used herein, the terms "immunogen" and "immunogenic" are meant to refer to substances capable of producing or generating an immune response in an organism. An immunogen can also be antigen. Usually, an immunogen has a fairly high molecular weight (e.g., greater than 10,000), thus, a variety of macromolecules such as proteins, lipoproteins, polysaccharides, some nucleic acids, and certain of the teichoic acids, can be coupled to a hapten in order to form an immunogen in accordance with the present invention.

As used herein, the term "immunogenicity" is meant to refer to the ability of a molecule to induce an immune response, which is determined both by the intrinsic chemical structure of the injected molecule and by whether or not the host animal can recognize the compound. Small changes in the structure of an antigen can greatly alter the immunogenicity of a compound, and have been used extensively as a general procedure to increase the chances of raising an antibody, particularly against well-conserved antigens. For example, these modification techniques either alter regions of the immunogen to provide better sites for T-Cell binding or expose new epitopes for B-cell binding.

As used herein, the terms "carrier," "immunogenic moiety," or "immunogenic carrier," are meant to refer to an operative group that is an immunogenic substance, commonly a protein, that can be coupled to a hapten. An immunogenic moiety coupled to a hapten can induce an immune response and elicit the production of antibodies that can bind specifically with the hapten. Immunogenic moieties are operative groups that include proteins, polypeptides, glycoproteins, complex polysaccharides, particles, nucleic acids, polynucleotides, and the like that are recognized as foreign and thereby elicit an immunologic response from the host. Additionally, linkers can comprise modified or unmodified nucleotides, nucleosides, polymers, sugars and other carbohydrates, polyethers such as, for example, polyethylene glycols, polyalcohols, polypropylenes, propylene glycols, mixtures of ethylene and propylene glycols, polyalkylamines, polyamines such as spermidine, polyesters such as poly(ethyl acrylate), polyphosphodiesters, and alkylenes. An example of an operative group and its linker is cholesterol-TEG-phosphoramidite, wherein the cholesterol is the operative group and the tetraethylene glycol and phosphate serve as linkers.

In one example, an operative group is an immunogenic carrier that can be coupled with a hapten in order to stimulate immunogenicity and antibody formation against the hapten. Usually, immunogenic carriers are large molecules that are highly immunogenic and capable of imparting immunogenicity to a hapten. For example, a protein can be used as an immunogenic carrier because foreign proteins can elicit such an immunological response. Protein carriers can be highly soluble and include functional groups that could facilitate easy conjugation with a hapten molecule. Some of the most common carrier proteins in use today are keyhole limpet hemocyanin (KLH; MW 450,000 to 13,000,000), and bovine serum albumin (BSA, MW 67,000). Keyhole limpet hemocyanin is the oxygen-carrying protein of the marine keyhole limpet, and is extremely large and exhibits increased immunogenicity when it is disassociated into subunits, probably due to exposure of additional epitopic sites to the immune system. BSA is highly soluble protein containing numerous functional groups suitable for conjugation.

As used herein, the term "antibody" is meant to refer to a protein that is produced in response to the presence of foreign molecules in the body. They can be characterized by their ability to bind both to antigens and to specialized cells or proteins of the immune system. Antibodies are divided into five classes, IgG, IgM, IgA, IgE, and IgD, and are immunoglobulin produced by plasma cells.

As used herein, the term "epitope" is meant to defines the region of an antigen that interacts with an antibody. Accordingly, a molecule or other substance, which is an antigen, can include at least one epitope with antibody activity. This can allow for an antigen to have various epitopes recognized by the same or different antibody. Also, an epitope is not an intrinsic property of any particular structure, but can be defined as a binding site that interacts with the antibody.

As used herein, the term "affinity" is meant to refer to a measure of the strength of binding between an epitope and an antibody. Accordingly, a single antibody can have a different affinity for various epitopes. This can allow a single antibody to bind strongly to one epitope and less strongly to another. As such, an antibody can have a first affinity to a drug, such as lamotrigine, and have a second affinity to a lamotrigine analog. However, it is possible for the antibody to have substantially equivalent or similar affinity for both lamotrigine and a lamotrigine analog, which allows the analog to be used to generate antibodies for lamotrigine, and their use in competitive binding studies. Thus, lamotrigine analogs in accordance with the present invention can be used to generate antibodies with affinity for lamotrigine.

As used herein, the term "avidity" is meant to refer to a measure of the overall stability of the complex between antibodies and antigens. The overall stability of an antibody-antigen interaction can be governed by three major factors as follows: (a) the intrinsic affinity of the antibody for the epitope; (b) the valency of the antibody and antigen; and (c) the geometric arrangement of the interacting components. As such, the avidity of the antibody-antigen complex can be modulated by varying the foregoing parameters, as well as others.

As used herein, the term "specificity" is meant to refer to the preferential binding of an antibody with an epitope in comparison with other available epitopes. That is, the specificity of an antibody can preferentially bind lamotrigine and/or analog instead of a lamotrigine metabolite. This can be used to generate anti-lamotrigine antibodies that preferentially bind with lamotrigine over its metabolites so that the true concentration of lamotrigine can be assessed so as to not be contaminated by adverse antibody-metabolite binding. Also, the specificity of an antibody for binding with lamotrigine can be used to tailor analogs with similar or substantially the same specificity as lamotrigine.

As used herein, the term "polyclonal antibody" is meant to refer to a heterogeneous mixture of antibodies with a wide range of specificities and affinities to a given antigen or epitope. Thus, the polyclonal antibody can include a plurality of antibodies, each distinguishable from the others, that bind or otherwise interact with an antigen. The different antibodies that comprise a polyclonal antibody can be produced or generated by injecting an immunogen having an epitope into an animal and, after an appropriate time, collecting and optionally purifying the blood fraction containing the antibodies of interest. In producing antibodies, several parameters can be considered with respect to the final use for the polyclonal antibody. These parameters include the following: (1) the specificity of the antibody (i.e., the ability to distinguish between antigens); (2) the avidity of the antibody (i.e., the strength of binding an epitope); and (3) the titer of the antibody, which determines the optimal dilution of the antibody in the assay system.

As used herein, the term "monoclonal antibody" is meant to refer to an antibody that is isolated from a culture of normal antibody-producing cells and one progenitor cell. A monoclonal antibody can have a homogeneous binding constant, and are well known in the art.

As used herein, "antibody titer" is meant to refer to the reciprocal of the serum dilution. Titers are reported this way for more convenient reporting and formatting. The titer of 1/50000 means that the antibody effectively detects the epitope of an antigen when bound together when the antigen is at a dilution of 1:50000. The titer is calculated by end point titer having about 10% of the maximum O.D.

As used herein, the terms "immunoassay" or "immunodiagnostic" are meant to refer to laboratory techniques that make use of the binding between an antigen and an antibody in order to identify and/or quantify at least one of the specific antigen or specific antibody in a biological sample. Currently, there are three classes of immunoassay, which are described as follows: (1) antibody capture assays; (2) antigen capture assays; and (3) two-antibody sandwich assays. Additionally, it is contemplated that new immunoassays will be developed and will be capable of employing the analogs and antibodies of the present invention.

As used here, the term "competitive immunoassay" is meant to refer to an experimental protocol in which a known amount of an identifiable antigen competes with another antigen for binding with an antibody. That is, a known antigen that binds with a known antibody is combined with a sample that is suspected of containing another antigen that also binds with the known antibody. This allows for the known antigen and another antigen to both compete for the binding site on the antibody. For example, a lamotrigine analog that binds with an anti-lamotrigine antibody can be combined with a sample suspected of containing lamotrigine, and the analog and lamotrigine compete for binding with the anti-lamotrigine antibody. The competition for binding with the antibody can then be used to determine whether or not lamotrigine is present in the sample, and can further be used to quantify the amount of lamotrigine in the sample.

As used herein, the term "turbidimetric detection" is meant to refer to the measurement of a decrease in the intensity in the transmission, or an increase in absorbance, of incident light due to light scattered by agglutinated particles. A decrease in intensity of transmitted light is measured against a higher starting background intensity of transmitted light. Usually, the reading is made with a detector in line with the light source, wherein the agglutination of particles inhibits transmission of the light. Therefore, the inhibition or promotion of agglutination can be used as a means for assessing the presence of a target analyte, such as lamotrigine. Turbidimetric assays may be easily adapted to a variety of clinical analyzers.

As used herein, the term "microparticle agglutination assays" is meant to refer to immunoassays that use the principle of inhibiting agglutination of microparticles by a target analyte. That is, decreased agglutination is attributed to the presence of the target analyte. For example, a derivative of the target drug is covalently linked to the surface of microparticle and/or the sensitized particles are agglutinated by a monoclonal antibody. When a sample contains free drug the agglutination is inhibited in proportion to the drug concentration, which leads to a classic inhibition curve relating drug concentration to absorbance.

As used herein, the term "operative group" is meant to refer to a molecule or macromolecule coupled to lamotrigine through a linker group. An operative group can include an immunogenic moiety, antigen moiety, tracer moiety, and the like. Additionally, the Z group in the chemical scaffolds described herein is an operative group. As such, the operative group can be coupled to the Y linker group and provide an additional functionality to the analong.

As used herein, the terms "active ester" or "activated ester" are meant to refer to an ester group that can react with a free amino group of a compound such as, for example, peptides and proteins. An active ester can include a carboxyl group linked to an active leaving group. Often, the active leaving group includes the ester oxygen so the active leaving group removes the ester oxygen. For example, an active ester is susceptible to being displaced by a primary amine, which results in the removal of the ester oxygen and formation of an amide group. Examples of active leaving groups that form active esters include N-hydroxysuccinimide ("NHS"), p-nitrophenyl, pentafluorophenyl, N-hydroxybenzotriazolyl, and the like. Accordingly, use of the term "NHS" is meant to be defined as N-hydroxysuccinimide.

As used herein, the terms "label," "detector molecule," or "tracer" are meant to refer to any operative group which produces, or can be induced to produce, a detectable signal. The label can be conjugated to lamotrigine, lamotrigine analog, hapten, analyte, immunogen, antibody, or to another molecule such as a receptor or a molecule that can bind to a receptor. Non-limiting examples of tracers include radioactive isotopes, enzymes, enzyme fragments, enzyme substrates, enzyme inhibitors, coenzymes, catalysts, fluorophores, dyes, chemiluminescers, luminescers, sensitizers, non-magnetic or magnetic particles, solid supports, liposomes, ligands, receptors, hapten radioactive isotopes, and the like. As described herein, the analogs can also be coupled to a variety of labels by methods well known in the art to provide a variety of reagents useful in various immunoassay formats. For detecting the results of the immunoassays, detector molecules such as fluorophores, for example, fluorescein, radio-labels, or chemiluminescent groups can be coupled to the analogs to produce tracers.

As used herein, the terms "linking group" or "linker" are meant to refer to a portion of a chemical structure that connects two or more substructures such as lamotrigine, lamotrigine analogs, haptens, and operative groups, such as immunogenic moieties, carriers, immunogens, labels, tracers, and the like. A linking group can have at least one uninterrupted chain of atoms other than hydrogen (or other monovalent atoms) extending between the substructures. Usually, a linking group includes a chain of carbon atoms or hetero atoms, which can be substituted or unsubstituted. The atoms of a linking group and the atoms of a chain within a linking group can be interconnected by chemical bonds. For example, linkers maybe straight or branched, substituted or unsubstituted, saturated or unsaturated chains, wherein the chain atoms can include carbon and/or hetero atoms. This can include one or more hetero atoms within the chain or at termini of the chains. Additionally, a linking group may also include cyclic and/or aromatic groups as part of the chain or as a substitution on one of the atoms in the chain. The number of atoms in a linking group or linker is determined by counting the atoms other than hydrogen in the backbone of the chain, which is the shortest route between the substructures being connected. Linking groups may be used to provide an available site on a hapten for conjugating a hapten with a tracer, label, carrier, immunogenic moiety, and the like.

As used herein, the term "hetero atoms" is meant to refer to atoms other than carbon atoms such as oxygen, nitrogen, sulfur, phosphorus, and the like. Usually, a heteroatom is multivalent so as to form at least two covalent bonds, which can be used in a linking group or other moiety.

As used herein, the term "biological sample" is meant to refer to a solid or fluid sample that is obtained from a biological entity. As such, a biological sample can include, but is not limited to, any quantity of a substance from a living thing or formerly living thing, such as humans and other animals. Such a substance can include, but is not limited to, blood, serum, plasma, urine, tears, cells, organs, tissues, bone, bone marrow, lymph, lymph nodes, synovial tissue, chondrocytes, synovial macrophages, endothelial cells, skin, and the like.

As used herein, the term "patient" is meant to refer to human and other animal subjects. More particularly, a patient is a human or other animal subject needing an anti-epileptic drug such as lamotrigine.

The lamotrigine analogs can include a lamotrigine molecule coupled to a linker moiety, and optionally include an operative group. The linker moiety and operative group can be any of a wide range of chemical compounds that can modify the physicochemical properties of lamotrigine. Accordingly, the linker moiety can be comprised of an alkyl, aliphatic, straight chain aliphatic, branched aliphatic, substituted aliphatic, cyclic aliphatic, heterocyclic aliphatic, aromatic, heteroaromatic, polyaromatic, and the like.

As used herein, the term "aliphatic" is meant to refer to a hydrocarbyl moiety, such as an alkyl group, that can be straight or branched, saturated or unsaturated, and/or substituted or unsubstituted, which has twenty or less carbons or hetero atoms in the backbone. Additionally, an aliphatic can include 10 or less carbons or hetero atoms in the backbone. An aliphatic group may comprise moieties that are linear, branched, cyclic and/or heterocyclic, and contain functional groups such as ethers, ketones, aldehydes, carboxylates, and the like. Exemplary aliphatic groups include but are not limited to substituted and/or unsubstituted groups of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, alkyl groups of higher number of carbons and the like, as well as 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl, and the like. The terms aliphatic or alkyl also encompasses alkenyl groups, such as vinyl, allyl, aralkyl and alkynyl groups.

Substitutions within an aliphatic group can include any atom or group that can be tolerated in the aliphatic moiety, including but not limited to halogens, sulfurs, thiols, thioethers, thioesters, amines (primary, secondary, or tertiary), amides, ethers, esters, alcohols, oxygen, and the like. The aliphatic groups can by way of example also comprise modifications such as azo groups, keto groups, aldehyde groups, carbonyl groups, carboxyl groups, nitro, nitroso or nitrile groups, heterocycles such as imidazole, hydrazino or hydroxylamino groups, isocyanate or cyanate groups, and sulfur containing groups such as sulfoxide, sulfone, sulfide, and disulfide. Additionally, the substitutions can be via single, double, or triple bonds, when relevant or possible.

Further, aliphatic groups may also contain hetero substitutions, which are substitutions of carbon atoms, by hetero atoms such as, for example, nitrogen, oxygen, phosphorous, or sulfur. As such, a linker comprised of a substituted aliphatic can have a backbone comprised of carbon, nitrogen, oxygen, sulfur, phosphorous, and/or the like. Heterocyclic substitutions refer to alkyl rings having one or more hetero atoms. Examples of heterocyclic moieties include but are not limited to morpholino, imidazole, and pyrrolidino.

As used herein, the term "aromatic" is meant to refer to molecule is one in which electrons are free to cycle around circular or cyclic arrangements of atoms, which are alternately singly and doubly bonded to one another. More properly, these bonds may be seen as a hybrid of a single bond and a double bond, each bond in the ring being identical to every other. Examples of aromatic compounds that can be present in lamotrigine analogs include benzene, benzyl, toluene, xylene, and the like. The aromatic compound can include hetero atoms so as to be a hetero aromatic such as pyridine, furan, tetrahydrofuran, and the like. Also, an aromatic can be a polycyclic aromatic such as naphthalene, anthracene, phenanthrene, polycyclic aromatic hydrocarbons, indole, quinoline, isoquinoline, and the like.

As used herein, the term "amine" is meant to refer to moieties that can be derived directly or indirectly from ammonia by replacing one, two, or three hydrogen atoms by other groups, such as, for example, alkyl groups. Primary amines have the general structures $RNH_2$ and secondary amines have the general structure $R_2NH$. The term amine includes, but is not limited to methylamine, ethylamine, propylamine, isopropylamine, aniline, cyclohexylamine, benzylamine, polycyclic amines, heteroatom substituted aryl and alkylamines, dimethylamine, diethylamine, diisopropylamine, dibutylamine, methylpropylamine, methylhexylamine, methylcyclopropylamine, ethylcyclohexylamine, methylbenzylamine, methycyclohexylmethylamine, butylcyclohexylamine, morpholine, thiomorpholine, pyrrolidine, piperidine, 2,6-dimethylpiperidine, piperazine, and heteroatom substituted alkyl or aryl secondary amines.

As used herein, the term "poly(amino acid)" or "polypeptide" is a polyamide formed from amino acids. Poly(amino acid)s will generally range from about 200-2,000 molecular weight or greater than about 2,000 molecular weight, or having no upper molecular weight limit, and normally being less than 10,000,000 and usually not more than about 600,000 daltons. There will usually be different ranges, depending on whether an immunogenic carrier or an enzyme is involved.

As used herein, the term "peptide" is meant to refer to any compound formed by the linkage of two or more amino acids by amide (peptide) bonds, usually a polymer of α-amino acids in which α-amino group of each amino acid residue (except the NH$_2$ terminus) is linked to the α-carboxyl group of the next residue in a linear chain. The terms "peptide," "polypeptide," and "poly(amino acid)" are used synonymously herein to refer to this class of compounds without restriction as to size. The largest members of this class are referred to as proteins having a defined polypeptide sequence.

Additionally, the terms used herein to describe the invention can be construed using the foregoing definitions and/or definitions well known in the art. As such, the foregoing terminology is meant to describe the invention and is not intended to be limiting.

I. Lamotrigine Analogs

In one embodiment, the present invention relates to analogs of lamotrigine, which can be used to prepare lamotrigine analog-based tracers, immunogens and/or analogs. The lamotrigine analogs can be prepared as derivatives of the benzene ring, such as a 4- or 5-position substitution on the benzene ring at the 4 and 5 atoms, and/or derivatives of the triazine ring, such as a 3-position substitution on the triazine ring at the 3 atom, as shown below. The lamotrigine analogs can be coupled to an immunogenic moiety in order to produce a lamotrigine analog-based immunogens that can be used in preparing monoclonal and polyclonal antibodies. Accordingly, the antibodies generated using unique lamotrigine immunogens can interact and/or bind with lamotrigine and the analogs. These antibodies, immunogens, antigens, and analogs can be useful in preparing for and performing immunoassays for the detection of lamotrigine in biological fluids.

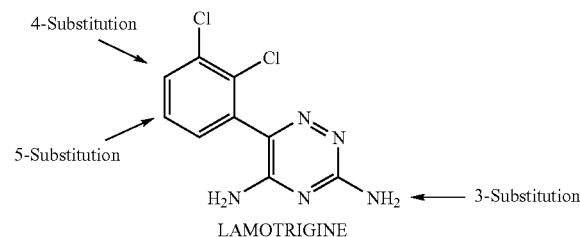 [SMILES: Nc1nnc(-c2cccc(Cl)c2Cl)c(N)n1]

LAMOTRIGINE

In one embodiment, the present invention describes novel analogs of lamotrigine having 5-substitutions at the 5 atom on the benzene ring. That is, the benzene ring can be conjugated to a linking moiety and/or analog moiety at the 5 atom so as to form an analog. The analog moiety can be considered to be the substituent that is coupled with the lamotrigine scaffold in order to form the analog. The analog moiety can be any of a wide array of chemical entities, which are described in more detail below. Accordingly, the 5-substitution analog of lamotrigine can have the generic structure of Formula 1A and/or Formula 1B:

FORMULA 1A

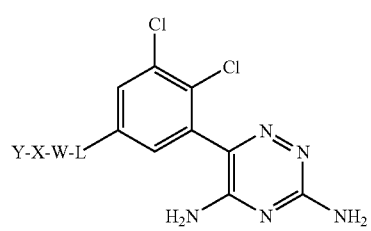

FORMULA 1B

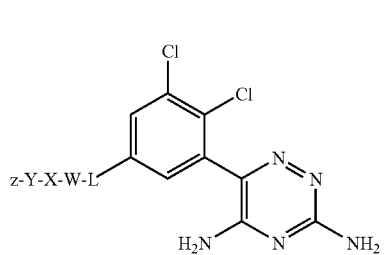

The lamotrigine scaffold depicted in Formula 1A and/or Formula 1B can be substituted with a wide range of chemical entities. However, it has been found that a 5-substitution succinylamino has unfavorable qualities. Although a 5-succinylamino analog (e.g., succinamic acid) of lamotrigine, which is know as chemical 74W86, can be coupled to a carrier directly, it is highly polar with poor solubility in most common solvents. Moreover, activated esters or activated species, which can be generated in situ, are highly unstable. The coupling between 74W86 and carrier protein is very inefficient and do not produce anti-lamotrigine antibodies that are sufficient for use in immunoassays, which usually have a low titer. Thus, the following descriptions of the analog moiety can be construed to be exclusive of the 5-succinylamino analog. However, 74W86 can be further modified for improved physiochemical properties in order to produce a lamotrigine analog in accordance with the present invention.

Additionally, with respect to Formulas 1A and 1B, when L and W cooperate so as to form an amide bond coupled to the lamotrigine scaffold, W, X, and Y cannot cooperate so as to form HOOC(CH$_2$)$_2$C=O. Thus, L-W—X—Y does not form a 5-succinylamide group.

In another embodiment, the lamotrigine scaffold can include a 4-substitution similar to the 5-substitution. Accordingly, the 4-substitution analog of lamotrigine can have the generic structure of Formula 2A and/or Formula 2B:

FORMULA 2A

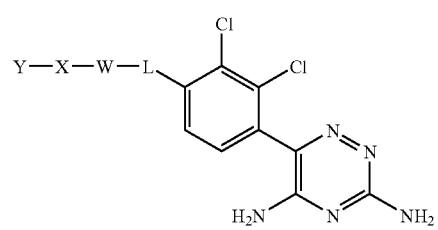

FORMULA 2B

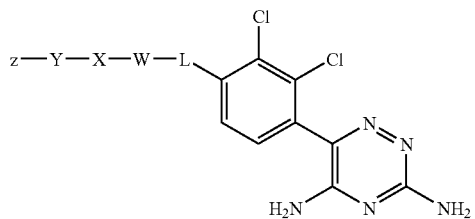

With regard to Formulas 2A and 2B, when Z is nothing and L and W cooperate so as to form an amide bond coupled to the lamotrigine scaffold, W, X, and Y can cooperate so as to form $HOOC(CH_2)_2C=O$. As such, the analog moiety can consist of a 4-succinylamido substitution.

In another embodiment, the lamotrigine scaffold can include a 3-substitution in the triazine ring. Accordingly, the 3-substitution analog of lamotrigine can have the generic structure of Formula 3A and/or Formula 3B:

FORMULA 3A

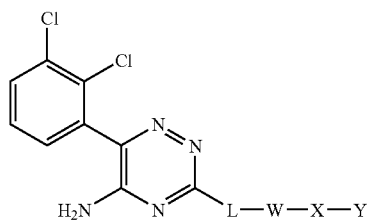

FORMULA 3B

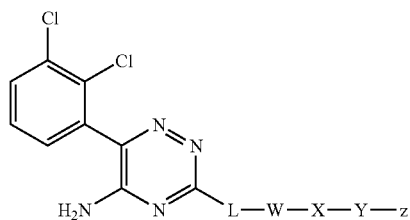

With regard to Formulas 3A and 3B, when Z is nothing and L and W cooperate so as to form an amide bond coupled to the lamotrigine scaffold, W, X, and Y can cooperate so as to form $HOOC(CH_2)_2C=O$. As such, the analog moiety can consist of a 4-succinylamido substitution.

The lamotrigine scaffolds depicted in Formulas 1A, 1B, 2A, 2B, 3A, and 3B, L can be a wide range of chemical entities. Accordingly, the L group can be selected from the group NH (amino), NHCO (amide), $SO_2$, O, and aliphatic groups. As such, the L group can be used as a linking group to conjugate the analog moiety and/or immunogenic moiety to the lamotrigine scaffold.

Additionally, the W group can be an aliphatic, which can be exemplified as a saturated or unsaturated, substituted or unsubstituted, and straight or branched chain having 1-10 carbon or hetero atoms. The X group can be at least one of an aliphatic, bond between W and Y, a substituted or unsubstituted aromatic or aliphatic group having from 1-2 rings, and/or a saturated or unsaturated, substituted or unsubstituted, or straight or branched chain having 1-10 carbon or hetero atoms. Some examples of substitutions on the aliphatic linker groups include primary and secondary amines, carbonyl groups, halogens, and the like.

The Y group can be an end group or a coupling group, which can be used for coupling the linker group with an operative group, such as a carrier, label, immunogenic moiety, and the like. Also, the Y group can be a reactive group that is used to couple the linking group to the Z group. As such, Y can be various groups, such as aliphatics, amines, amides, carboxylic acids, aldehydes, esters, activated esters, aliphatic esters, imidoesters, isocyanates, isothiocyanates, anhydrides, thiols, alcohols, thiolactones, diazoniums, maleimido groups, and the like. Also, Y can be a $Y_1$—Z, wherein $Y_1$ is linking group derived from the Y end group or coupling group being coupled to the Z group.

Furthermore, the operative group Z can be nothing or any moiety that can be coupled to the linker moiety. As such, the L-W—X—Y group can be considered to be the linker moiety and the Z group can be an operative group. As such, the linker moiety can functionally serve as a linker or linking group between the lamotrigine scaffold and an operative group. For example, the operative group can be a carrier, label, tracer, protein, enzyme, fluorogenic compound, phosphorogenic compound, thermochromic compound, photochromic compound, anti-stokes up-regulating compound, chemiluminescent material, electrochemical mediator, particle, reporter group, enzyme inhibitor, nucleic acid, polypeptide, and the like.

For example, the W group can comprise a chain of one or more atoms, wherein at least one atom is carbon if present. Illustratively, W can be any of the following groups: $CH_2$; $(CH_2)_2$; $(CH_2)_3$; $(CH_2)_4$; $(CH_2)_5$; $(CH_2)_6$; $CH_2CO$; $(CH_2)_2CO$; $(CH_2)_3CO$; $(CH_2)_4CO$; $(CH_2)_5CO$; $(CH_2)_6CO$; $CH_2COO$; $(CH_2)_2COO$; $(CH_2)_3COO$; $(CH_2)_4COO$; $(CH_2)_5COO$; $(CH_2)_6COO$; CO; COO; $COCH_2$; $CO(CH_2)_2$; $CO(CH_2)_3$; $CO(CH_2)_4$; $CO(CH_2)_5$; $CO(CH_2)_6$; $COCH_2CO$; $CO(CH_2)_2CO$; $CO(CH_2)_3CO$; $CO(CH_2)_4CO$; $CO(CH_2)_5CO$; $CO(CH_2)_6CO$; $COCH_2COO$; $CO(CH_2)_2COO$; $CO(CH_2)_3COO$; $CO(CH_2)_4COO$; $CO(CH_2)_5COO$; $CO(CH_2)_6COO$; $CO(CH_2)_2CONHCH_2$; $CO(CH_2)_2CONH(CH_2)_2$; $CONH(CH_2)_3$; $CONH(CH_2)_3CO$; $CONH(CH_2)_3COO$; $NHCH_2$; $NH(CH_2)_2$; $NH(CH_2)_3$; $NH(CH_2)_4$; $NH(CH_2)_5$; $NH(CH_2)_6$; $NHCH_2CO$; $NH(CH_2)_2CO$; $NH(CH_2)_3CO$; $NH(CH_2)_4CO$; $NH(CH_2)_5CO$; $NH(CH_2)_6CO$; $NHCH_2COO$; $NH(CH_2)_2COO$; $NH(CH_2)_3COO$; $NH(CH_2)_4COO$; $NH(CH_2)_5COO$; $NH(CH_2)_6COO$; $NHCO(CH_2)_2$; $NHCO(CH_2)_6$; $NHCO(CH_2)_2CO$; $HCO(CH_2)_6CO$; $NHCO(CH_2)_2COO$; or $NHCO(CH_2)_6COO$; combinations thereof; and the like. More preferably, W is selected from the group consisting of $CH_2$j ($CH_2)_2$, $(CH_2)_3$, $CH_2COO$, $(CH_2)_2CO$, $(CH_2)_2COO$, $(CH_2)_3CO$, $(CH_2)_3COO$, $CO(CH_2)_6$, $CO(CH_2)_6CO$, $CO(CH_2)_6COO$, CO, COO $CONH(CH_2)_3$, $CONH(CH_2)_3CO$, $CONH(CH_2)_3COO$, $CO(CH_2)_2$, $COCH_2$, $CO(CH_2)_2CONHCH_2$, $CO(CH_2)_2CONH(CH_2)_2$, combinations thereof, and the like. Most preferably, W is selected from the group consisting of $CO(CH_2)_2$, $COCH_2$, $CO(CH_2)_2CONHCH_2$, and $CO(CH_2)_2CONH(CH_2)_2$. In one embodiment, W can be an aliphatic group having from 5 to 10 carbon and/or hetero chain atoms.

For example, the X group can be a bond or a chain of zero or more atoms, wherein at least one atom is carbon if present. As such, X can be a covalent bond between L and Y. Illustratively, X can be any of the following groups: $CH_2$; $(CH_2)_2$; $(CH_2)_3$; $(CH_2)_4$; $(CH_2)_5$; $(CH_2)_6$; $CH_2CO$; $(CH_2)_2CO$; $(CH_2)_3CO$; $(CH_2)_4CO$; $(CH_2)_5CO$; $(CH_2)_6CO$; $CH_2COO$; $(CH_2)_2COO$; $(CH_2)_3COO$; $(CH_2)_4COO$; $(CH_2)_5COO$; $(CH_2)_6COO$; CO; COO; $COCH_2$; $CO(CH_2)_2$; $CO(CH_2)_3$; $CO(CH_2)_4$; $CO(CH_2)_5$; $CO(CH_2)_6$; $COCH_2CO$; $CO(CH_2)_2CO$; $CO(CH_2)_3CO$; $CO(CH_2)_4CO$; $CO(CH_2)_5CO$; $CO(CH_2)_6CO$; $COCH_2COO$; $CO(CH_2)_2COO$; $CO(CH_2)_3COO$;

$CO(CH_2)_4COO$; $CO(CH_2)_5COO$; $CO(CH_2)_6COO$; $CO(CH_2)_2CONHCH_2$; $CO(CH_2)_2CONH(CH_2)_2$; Ph; $CONHCH_2Ph$; $CONH(CH_2)_3$; $CONH(CH_2)_3CO$; $CONH(CH_2)_3COO$; $NHCH_2$; $NH(CH_2)_2$; $NH(CH_2)_3$; $NH(CH_2)_4$; $NH(CH_2)_5$; $NH(CH_2)_6$; $NHCH_2CO$; $NH(CH_2)_2CO$; $NH(CH_2)_3CO$; $NH(CH_2)_4CO$; $NH(CH_2)_5CO$; $NH(CH_2)_6CO$; $NHCH_2COO$; $NH(CH_2)_2COO$; $NH(CH_2)_3COO$; $NH(CH_2)_4COO$; $NH(CH_2)_5COO$; $NH(CH_2)_6COO$; $NHCO(CH_2)_2$; $NHCO(CH_2)_6$; $NHCO(CH_2)_2CO$; $HCO(CH_2)_6CO$; $NHCO(CH_2)_2COO$; or $NHCO(CH_2)_6COO$; combinations thereof; and the like. More preferably, X is selected from the group consisting of $CH_2$, $(CH_2)_2$, $(CH_2)_3$, $CH_2COO$, $(CH_2)_2CO$, $(CH_2)_2COO$, $(CH_2)_3CO$, $(CH_2)_3COO$, $CO(CH_2)_6$, $CO(CH_2)_6CO$, $CO(CH_2)_6COO$, CO, COO, Ph, $CONH(CH_2)_3$, $CONH(CH_2)_3CO$, $CONH(CH_2)_3COO$, combinations thereof, and the like. Most preferably, X is selected from the group consisting of $CH_2$, $CONHCH_2Ph$, $CONH(CH_2)_2$, Ph, $NHCO(CH_2)_6$, and $NHCO(CH_2)_2$.

For example, in each of Formulas 1 and 2 the Y group can comprise an end group or linker derived from the end group and is always present. Illustratively, Y can be any of the following end groups or a linker group derived therefrom: COOH (carboxylic acid); COO; COO—NHS(NHS active ester); NHS; COO-tertbutyl; tertbutyl (t-butyl); OH; O—NHS(NHS active ester linker); $COOCH_2CH_3$; $COOCH_3$; $OCH_2CH_3$; $OCH_3$; NH; $NH_2$; NHCO (amide); combinations thereof; and the like. More preferably, when Y is an end group, it is selected from the group consisting of NHS, COOH, COO—NHS, COO-tertbutyl, tertbutyl, OH, O—NHS, $COOCH_2CH_3$, $COOCH_3$, $OCH_2CH_3$, $OCH_3$, or $NH_2$. On the other hand, when Y is a linker, it is $Y_1$—Z, wherein $Y_1$ is selected from the group consisting of is at least one of COO, CO, O, CONH, or NH and Z is a macromolecule.

Accordingly, the conjugate Z or macromolecule can be a carrier, tracer, or a label, such as protein, enzyme, fluorescent compound, chemiluminescent material, electrochemical mediator, particle, reporter group, enzyme inhibitor, and/or nucleic acid. Illustratively, Z can be any of the following conjugate groups: (a) BSA; (b) KLH; (c) fluorescent tracer; and (d) the like.

In one embodiment, the lamotragine analog can have L-W—X—Y selected from the group consisting of $NHCO(CH_2)_2CONH(CH_2)_2NHCOOH$, $NHCO(CH_2)_2CONH(CH_2)_2NHCOONHS$, $NHCO(CH_2)_2CONH(CH_2)_2NHCOOCH_2CH_3$, $NHCO(CH_2)_2CONH(CH_2)_2NHCO(CH_2)_2COOH$, $NHCO(CH_2)_2CONH(CH_2)_2NHCO(CH_2)_2COONHS$, $NHCO(CH_2)_2CONH(CH_2)_2NHCO(CH_2)_2COOCH_2CH_3$, $NHCO(CH_2)_2CONH(CH_2)_2NHCO(CH_2)_3COOH$, $NHCO(CH_2)_2CONH(CH_2)_2NHCO(CH_2)_3COONHS$, $NHCO(CH_2)_2CONH(CH_2)_2NHCO(CH_2)_3COOCH_2CH_3$, $NHCO(CH_2)_2CONH(CH_2)_2NHCO(CH_2)_6COOH$, $NHCO(CH_2)_2CONH(CH_2)_2NHCO(CH_2)_6COONHS$, $NHCO(CH_2)_2CONH(CH_2)_2NHCO(CH_2)_6COOCH_2CH_3$, $NHCO(CH_2)_2CONH(CH_2)_2NHCH_2PhCOOH$, $NHCO(CH_2)_2CONH(CH_2)_2NHCH_2PhCOONHS$, $NHCO(CH_2)_2CONH(CH_2)_2NHCH_2PhCOOCH_2CH_3$, $NHCO(CH_2)_2CONH(CH_2)_2NHCONH(CH_2)_3COOH$, $NHCO(CH_2)_2CONH(CH_2)_2NHCONH(CH_2)_3COONHS$, $NHCO(CH_2)_2CONH(CH_2)_2NHCONH(CH_2)_3COOCH_3$, $NHCO(CH_2)_2CONHCH_2PhCOOH$, $NHCO(CH_2)_2CONHCH_2PhCOOCH_2CH_3$, $NHCO(CH_2)_2COOH$, $NHCO(CH_2)_2COONHS$, $NHCO(CH_2)_2COOCH_2CH_3$, $NHCO(CH_2)_3COOH$, $NHCO(CH_2)_3COONHS$, $NHCO(CH_2)_3COOCH_2CH_3$, $NHCO(CH_2)_6COOH$, $NHCO(CH_2)_6COONHS$, $NH(CH_2)_2NHCO(CH_2)_6COOCH_2CH_3$, $NH(CH_2)_2NH(CH_2)_3COOC(CH_3)_3$, $NH(CH_2)_2NH(CH_2)_3COOH$, $NH(CH_2)_2NH(CH_2)_3COONHS$, $NHCH_2PhCOOH$, $NHCH_2PhCOONHS$, $NHCOPhCOOH$, $NHCOPhCOONHS$, $OOCNH(CH_2)_3COOCH_2CH_3$, $OOCNH(CH_2)_3COOCH_3$, $OOCNH(CH_2)_3COONHS$, $OOCNH(CH_2)_3COOH$, $NH(CH_2)_3COOH$, $NH(CH_2)_3COONHS$, and the like.

In one embodiment, the lamotragine analog can have L-W—X—Y—Z selected from the group consisting of $NHCO(CH_2)_2CONH(CH_2)_2NHCOO$-BSA, $NHCO(CH_2)_2CONH(CH_2)_2NHCO(CH_2)_2COO$-BSA, $NHCO(CH_2)_2CONH(CH_2)_2NHCO(CH_2)_3COO$-BSA, $NHCO(CH_2)_2CONH(CH_2)_2NHCO(CH_2)_6COO$-BSA, $NHCO(CH_2)_2CONH(CH_2)_2NHCH_2PhCOO$-BSA, $NHCO(CH_2)_2CONH(CH_2)_2NHCONH(CH_2)_3COO$-BSA, $NHCO(CH_2)_2CONHCH_2PhCOO$-BSA, $NHCO(CH_2)_2COO$-BSA, $NHCO(CH_2)_3COO$-BSA, $NH(CH_2)_2NHCO(CH_2)_6COO$-BSA, $NH(CH_2)_2NH(CH_2)_3COO$-BSA, $NHCH_2PhCOO$-BSA, $NHCOPhCOO$-BSA, $OOCNH(CH_2)_3COO$-BSA, $NH(CH_2)_3COO$-BSA, and the like.

In one embodiment, the lamotrigine analogs of Formulas 1A, 2A, and 3A can be used as therapeutic agents. As such, the lamotrigine analogs can be used as anti-epileptic drugs similarly as lamotrigine. However, when a lamotrigine analog is used as an therapeutic agent, Z is preferably nothing so as to not form an immunogen. Thus, the non-immunogenic analogs of lamotrigine can be used in anti-epileptic regimens for animals, including humans.

II. Lamotrigine Immunogens

Implementing an immunoassay for the detection of a small molecule, such as lamotrigine, can be a challenge. This is because such small molecules can often lack antigenicity, which makes it difficult to generate antibodies against lamotrigine, and is particularly problematic with lamotrigine, which lacks immunogenicity. To increase the immunogenicity, larger antigenic compounds, including but not limited to bovine serum albumin, ovalbumin, keyhole limpet hemocyanin, and the like, can be coupled to the drug. Further, detection of the drug in an immunoassay generally requires the use of a detectable label conjugated to an antibody, lamotrigine, or lamotrigine analog.

Immunogens may be made by coupling lamotrigine to an antigenic carrier protein through a linker of one of the lamotrigine analogues. As such, an immunogen based on lamotrigine is also considered a lamotrigine analog. Illustratively, a 5-amino substitution on the benzene ring has been shown to link with a protein, which is described by Sailstad et al, *Ther Drug Monitoring* 13:433-442 (1991), which is incorporated herein by reference. However, the antibodies generated from the immunogen described by Sailstad et al. were not satisfactory in any immunoassay, especially automated immunoassays. The poor immunogenicity can be attributed to poor titer, poor sensitivity, BSA not being as immunogenic as KLH, and a short linker at the 5-position.

Figure 10:
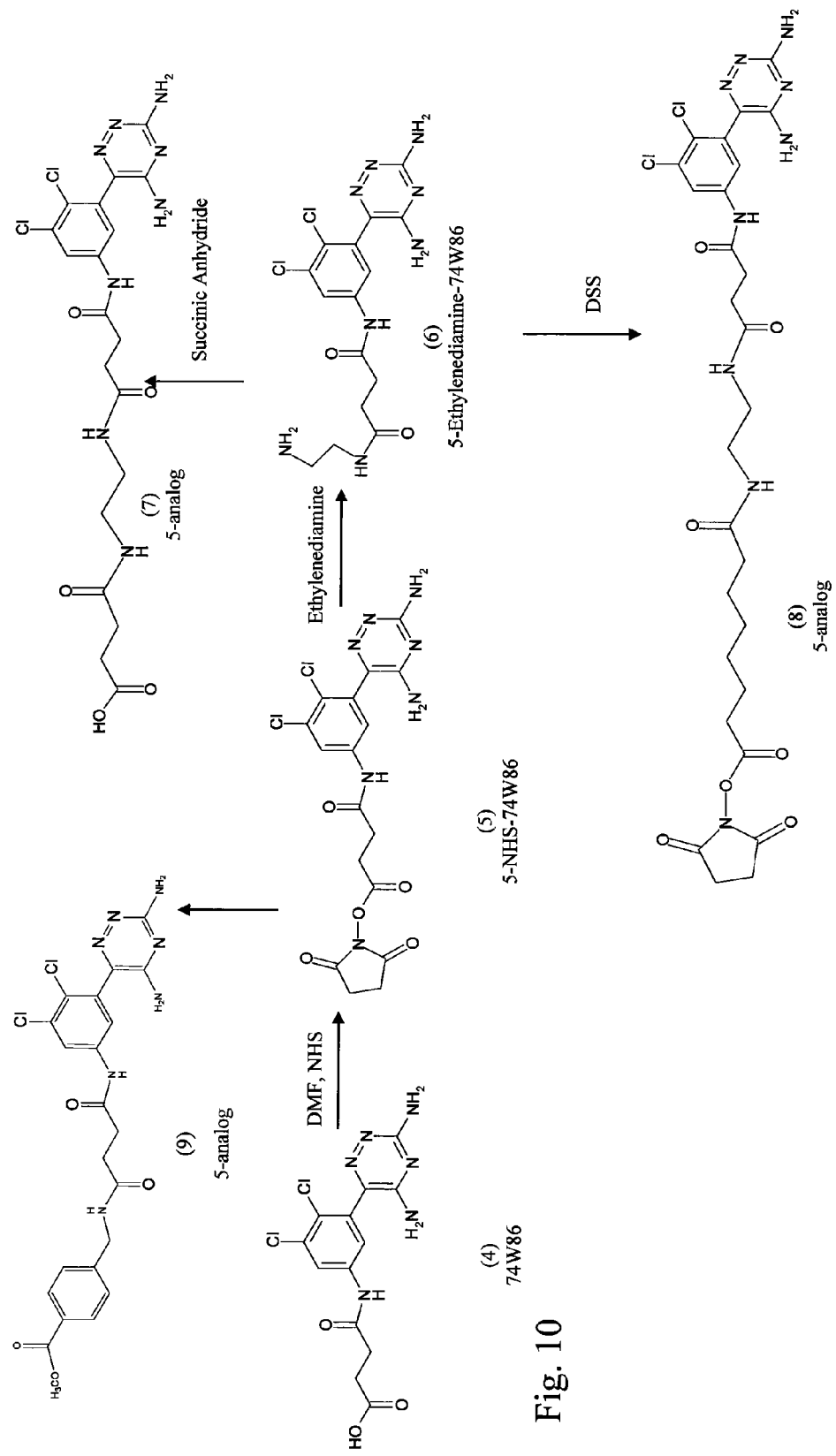
FIG. 10 is a schematic diagram illustrating an embodiment of synthesis protocols for synthesizing lamotrigine analogs.

In an attempt to improve the efficiency of coupling to carrier protein, 74W85 was modified with NHS into an activated ester derivative 5-NHS-74W86 (5) isolated (e.g., L, NH; W is C=O; X is $CH_2CH_2$; Y is NHS activated ester), as shown in FIG. 10. The 5-NHS active ester (5) can be efficiently coupled to a carrier protein because it reacts directly with lysine or other amines within the protein. Examples of such a coupling can be seen in the immunogen 5-KLH-74W86 (20) of FIG. 13E. However, the linker of (20) proved to be too short to provide an accessible epitope for antibody interaction in two immunizations programs described in more detail below.

Due to the unsuccessful immunization programs, new haptens for lamotrigine were explored extensively, which included longer linkers conjugated to the 5-position, and linkers of various length conjugated to the 4-position and 3-position. Accordingly, FIGS. 13A-13D illustrate immunogens prepared in accordance with the present invention and are as follows: (a) 3-lamotrigine immunogen (18); (b) 5-long linker lamotrigine immunogen (16); (c) 5-long linker lamotrigine immunogen (19); and (d) 4-lamotrigine immunogen (17). Specifically, 5-long linker lamotrigine immunogens (16) and (19) have much longer linkers to provide for a more accessible epitope. As such, the lamotrigine moiety is much more accessible for the antibody interaction and is much more immunogenic.

In one embodiment, the present invention relates to immunogens prepared from the forgoing lamotrigine analog scaffolds. Namely, the analogs of Formulas 2B, 3B, and 4B can include the linker moieties as described above, and Z can be an operative group, such as an immunogenic moiety. As such, Z can be any immunogenic moiety that can elicit an immunological response and provide for antibodies to be produced that target at least a portion of the lamotrigine analog.

An immunogenic moiety can include various proteins or polypeptides, which can function as an immunogenic carrier. These types of polypeptides include albumins, serum proteins, globulins, ocular lens proteins, lipoproteins, and portions thereof. Illustrative proteins include bovine serum albumin ("BSA"), keyhole limpet hemocyanin ("KLH"), egg ovalbumin, bovine gamma-globulin ("BGG"), and the like. Alternatively, synthetic polypeptides may be utilized. Additionally, an immunogenic moiety can also be a polysaccharide, which is a high molecular weight polymer. Examples of polysaccharides are starches, glycogen, cellulose, carbohydrate gums such as gum arabic, agar, and the like. Also, an immunogenic moiety can be a polynucleotide, such as DNA or RNA. The polynucleotide can be modified or unmodified, and be comprised of any number of nucleic acids so long as it provides the carrier and/or immunogenic functionality. The polysaccharide can also contain or link to a polypeptide residue, polynucleotide residue, and/or lipid residues. Furthermore, an immunogenic moiety can also be a polynucleotide either alone or conjugate to one of the polypeptides or polysaccharides mentioned above.

An immunogenic moiety or carrier can also be a particle or microparticle. The immunogenic particles are generally at least about 0.02 microns (urn) and not more than about 100 μm, and usually about 0.05 μm to 10 μm in diameter. The particle can be organic or inorganic, swellable or non-swellable, and/or porous or non-porous. Optionally, an immunogenic particle can have a density approximating water, generally from about 0.5 to 1.5 g/ml, and be composed of a material that can be transparent, partially transparent, or opaque. The immunogenic particles can be biological materials such as cells and microorganisms, including non-limiting examples such as erythrocytes, leukocytes, lymphocytes, *Streptococcus, Staphylococcus aureus, E. coli*, and viruses. The particles can also be comprised of organic and inorganic polymers, liposomes, latex, phospholipid vesicles, liposomes, cationic liposomes, anionic liposomes, lipoproteins, lipopolymers, and the like.

In one embodiment, the lamotragine analog can have L—W—X—Y—Z selected from the group consisting of NHCO(CH$_2$)$_2$CONH(CH$_2$)$_2$NHCOO-KLH, NHCO(CH$_2$)$_2$CONH(CH$_2$)$_2$NHCO(CH$_2$)$_2$COO-KLH, NHCO(CH$_2$)$_2$CONH(CH$_2$)$_2$NHCO(CH$_2$)$_3$COO-KLH, NHCO(CH$_2$)$_2$CONH(CH$_2$)$_2$NHCO(CH$_2$)$_6$COO-KLH, NHCO(CH$_2$)$_2$CONH(CH$_2$)$_2$NHCH$_2$PhCOO-KLH, NHCO(CH$_2$)$_2$CONH(CH$_2$)$_2$NHCONH(CH$_2$)$_3$COO-KLH, NHCO(CH$_2$)$_2$CONHCH$_2$PhCOO-KLH, NHCO(CH$_2$)$_2$COO-KLH, NHCO(CH$_2$)$_3$COO-KLH, NH(CH$_2$)$_2$NHCO(CH$_2$)$_6$COO-KLH, NH(CH$_2$)$_2$NH(CH$_2$)$_3$COO-KLH, NHCH$_2$PhCOO-KLH, NHCOPhCOO-KLH, OOCNH(CH$_2$)$_3$COO-KLH, NH(CH$_2$)$_3$COO-KLH, and the like.

Thus, the immunogens prepared in accordance with the present invention can be used to generate antibodies that can have an affinity for lamotrigine as well as lamotrigine analogs.

III. Antibodies for Lamotrigine and Lamotrigine Analogs

In one embodiment, a lamotrigine analog-based immunogen in accordance with the present invention can be used in an embodiment of a method for producing monoclonal and/or polyclonal antibodies. As such, antibodies can be produced from the lamotrigine-based immunogen that interacts and/or binds with lamotrigine. This can allow for the analogs of the present invention to be useful in preparing antibodies for use in immunoassays for identifying the presence of lamotrigine. Also, methods of producing antibodies with immunogens are well known in the art. The immunogens can be used in the screening for the monoclonal and/or polyclonal antibodies that interact and/or bind with lamotrigine.

Additionally, the sera can be obtained, processed and/or purified by well-known techniques for collecting antibodies. As such, monoclonal and/or polyclonal antibodies can be obtained that interact and/or bind with both lamotrigine and a lamotrigine analog. This allows for the lamotrigine-immunogen to be used in preparing antibodies that recognize lamotrigine and can be used in immunodiagnostic assays.

FIG. 1 is a flow diagram illustrating one embodiment of a method 10 for obtaining anti-lamotrigine antibodies, an immunogen based on a lamotrigine analog can be obtained (Block 12). The immunogen can then be combined with an immunogenic formulation (Block 14). Briefly, about 0.5 of an immunogen composition is admixed with about 0.5 ml of complete Freund's adjuvant; however, other amounts of immunogen and/or adjuvant can be used. The immunogenic formulation can then be administered to an antibody producing subject (Block 16), which can be a rat, mouse, pig, rabbit, bird and/or other animal, but preferably mammals. The administration can be via tail vein injection, subcutaneous injection, intravenous injection, or other well-known injection sites. Subsequently, immunogenic boosters can be administered to the animal that received the initial administration (Block 18), wherein the booster can include substantially the same ingredients as the initial formulation and can be administered at predetermined intervals. For example, the initial administration can be followed by subsequent boosters once a week or at other longer or shorter intervals. After at least the initial administration, and optionally after subsequent boosters, the anti-lamotrigine antibodies produced by the animal can be collected (Block 20). The antibodies can be collected by obtaining blood, serum, plasma, or other biological sample from the animal previously administered the immunogen. Optionally, he antibody-containing composition can then be processed as is well known in the art (Block 22), wherein such processing can include techniques that place the antibodies into a format suitable for performing an immunodiagnostic assay. Alternatively, the processing can include screening the antibodies with ELISA by well known and established techniques. As such, the processing can be used to obtain polyclonal antibodies (Block 24), which can also result in purifying polyclonal antibodies (Block 26). Alternatively, techniques well known in the art can be used to obtain monoclonal antibodies, which can also result in purifying monoclonal antibodies.

IV. Immunodiagnostic Assays

The anti-lamotrigine antibodies, either monoclonal or polyclonal, can be used in immunoassays for identifying the presence of lamotrigine in a sample, such as blood, plasma, serum, tissue, and the like. This can be beneficial for identifying or accessing pharmacokinetic and/or pharmacodynamic parameters for lamotrigine in a patient or patient population. Thus, the anti-lamotrigine antibodies can be used in immunodiagnostic assays in place of other antibodies so that the assays can be configured for identifying the presence and optionally, quantifying the amount of lamotrigine. Additionally, the immunodiagnostic assays can use lamotrigine analogs in accordance with the present invention or other lamotrigine analogs.

A. Fluorescence Polarization Immunoassay for Lamotrigine

Fluorescence polarization immunoassay (FPIA) technology is based upon competitive binding between an antigen/drug in a sample and a known concentration of labeled antigen/drug. FPIA technology is described in U.S. Pat. Nos. 4,593,089, 4,492,762, 4,668,640, and 4,751,190, which are incorporated herein by reference. Accordingly, the FPIA reagents, systems, and equipment described in the incorporated references can be used with anti-lamotrigine antibodies which are also anti-lamotrigine analog antibodies.

The FPIA technology can be used to identify the presence of lamotrigine and can be used in assays that quantify the amount of lamotrigine in a sample. In part, the rotational properties of molecules in solution allow for the degree of polarization to be directly proportional to the size of the molecule. Accordingly, polarization increases as molecular size increases. That is, when linearly polarized light is used to excite a fluorescent-labeled or other luminescent-labeled lamotrigine or analog thereof, which is small and rotates rapidly in solution, the emitted light is significantly depolarized. When the fluorescent-labeled lamotrigine or analog interacts with or is bound to an antibody, the rotation is slowed and the emitted light is highly polarized. This is because the antibody significantly and measurably increases the size of the complex. Also, increasing the amount of unlabeled lamotrigine in the sample can result in decreased binding of the fluorescent-labeled lamotrigine or analog by the anti-lamotrigine antibody, and thereby decrease the polarization of light emitted from sample. The quantitative relationship between polarization and concentration of the unlabeled lamotrigine in the sample can be established by measuring the polarization values of calibrations with known concentrations of lamotrigine. Thus, FPIA can be used to identify the presence and concentration of lamotrigine in a sample.

One embodiment of the present invention is an FPIA assay system. An example of components of the FPIA system can include the following: i) monoclonal or polyclonal anti-lamotrigine antibodies capable of binding to lamotrigine and a lamotrigine analog; ii) a sample suspected of containing the lamotrigine; and iii) lamotrigine analog labeled with a fluorescent moiety, such as fluorescein. Alternatively, the system can be provided as a kit exclusive of the sample. Additionally, the system can include various buffer compositions, lamotrigine concentration gradient compositions or a stock composition of lamotrigine, and the like.

Figure 2:
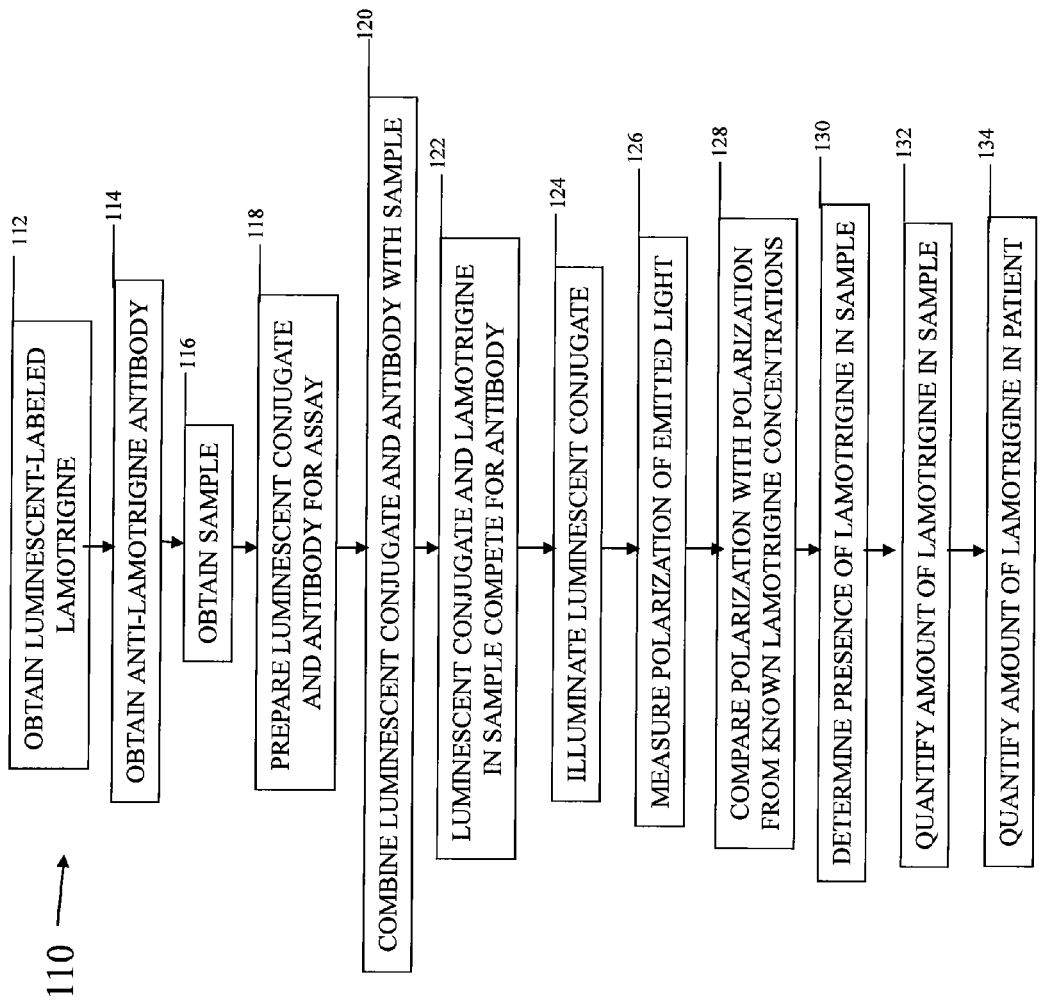
FIG. 2 is a flow diagram illustrating an embodiment of a method for performing an immunodiagnostic assay for lamotrigine.

FIG. 2 is a flow diagram illustrating one embodiment of a method 110 for performing a FPIA assay. As such, a luminescent-labeled lamotrigine or analog conjugate can be obtained (Block 112), and an anti-lamotrigine antibody can be obtained (Block 114). Additionally, a sample, such as a biological sample from a patient being administered lamotrigine, suspected of containing lamotrigine can be obtained (Block 116). Known amounts or concentrations of luminescent-labeled lamotrigine conjugate and anti-lamotrigine antibody can be obtained and formulated into separate compositions, such as in a standard buffer system, for use in a competitive binding assay (Block 118). The anti-lamotrigine antibody and luminescent-labeled lamotrigine conjugate are then combined with the biological sample into a reaction solution (Block 120). A competitive reaction takes place between the luminescent-labeled lamotrigine conjugate and the unknown amount of lamotrigine in the biological sample with the anti-lamotrigine antibody in the reaction solution (Block 122). After adequate duration and/or competition the luminescent conjugate is illuminated (Block 124), which can be by photoillumination, chemical-illumination, temperature-illumination, and the like. The polarization of the light emitted by the illumination is then measured (Block 126) and compared to polarization values of known amounts of lamotrigine and/or luminescent conjugate (Block 128), which can be used to determine whether or not lamotrigine is present in the sample (Block 130). Additionally, comparing the measurements obtained from the biological sample with standardized measurements obtained from known concentration standards can be used to quantify the amount of lamotrigine in the sample (Block 132), and thereby identify the amount of lamotrigine in the patient (Block 134).

B. Homogeneous Microparticle Immunoassay for Lamotrigine

Homogeneous microparticles immunoassay ("HMI") technology, which can be referred to as immunoturbidimetric assays, is based on the agglutination of particles and compounds in solution. When particles and/or chemical compounds agglutinate, particle sizes can increase and increase the turbidity of a solution. Accordingly, anti-lamotrigine antibodies can be used with microparticles and lamotrigine analogs in order to assess the presence, and optionally the amount, of lamotrigine in a sample. HMI technologies can be advantageous because the immunoassays can be performed on blood, blood hemolysate, serum, plasma, tissue, and/or other samples. HMI assays can be configured to be performed with lamotrigine and/or an analog loaded onto a microparticle, or with an anti-lamotrigine antibody loaded onto a microparticle. The use of an analog loaded microparticle can be especially advantageous because of the ability to efficiently load the microparticle. In any event, HMI or immunoturbidimetric assays are well known in the art for measuring agglutination of substances in a sample.

Immunoturbidimetric assay technologies are described in U.S. Pat. Nos. 5,571,728, 4,847,209, 6,514,770, 6,248,597, which are included herein by reference. Briefly, in homogeneous assay methods use is made predominantly of light attenuation, nephelometric, or turbidimetric methods. The formation of an agglutinated compound AB from lamotrigine (A) and anti-lamotrigine antibody microparticle binding partner (B) can be measured by the change which occurs in the scattering or absorption of the incident light directed into the sample. Alternatively, the anti-lamotrigine antibody (A) can bind with a lamotrigine or analog loaded microparticle. When suspendable particles having an immobilized binding partner are used, there is an enhancement of the effects, which makes it possible to determine considerably lower lamotrigine concentrations. These homogeneous methods can be carried out quickly and simply, and permit, in particular, the automation of sample analyses as described in more detail below.

For example, in high volume screening applications it can be desirable to have fully automated methods of analysis. As such, instruments can be designed to detect changes in light scattering by particles, such as sensitized latex particles, as a result of specific reaction with analyte. The assays that utilize such instruments can be made highly sensitive due to the vast surface area of latex particle suspensions and the physical principles of light scattering. The main principle of detection involves the light scattering change when two or more particles come into close contact during agglutination. When a beam of light is passed through a reaction cell containing un-agglutinated particles, there can be a certain degree of light scatter due to refraction, reflection, absorption, and diffraction by the particles. Accordingly, this principle can be beneficial for measuring the ability of a target analyte, such as lamotrigine to inhibit agglutination of particles. During the early stages of an antibody/antigen binding, complexes begin to form, wherein these complexes can substantially alter the angular distribution of the scattered light intensity because the complexes act like larger particles. The change of light scatter as a result of larger particles by agglutination may be measured by turbidimetric detection and other methods, as described in more detail below. Seradyn's Lamotrigine QMS® reagents permit the complete automation and are applicable to many clinical chemistry analyzers.

Figure 3:
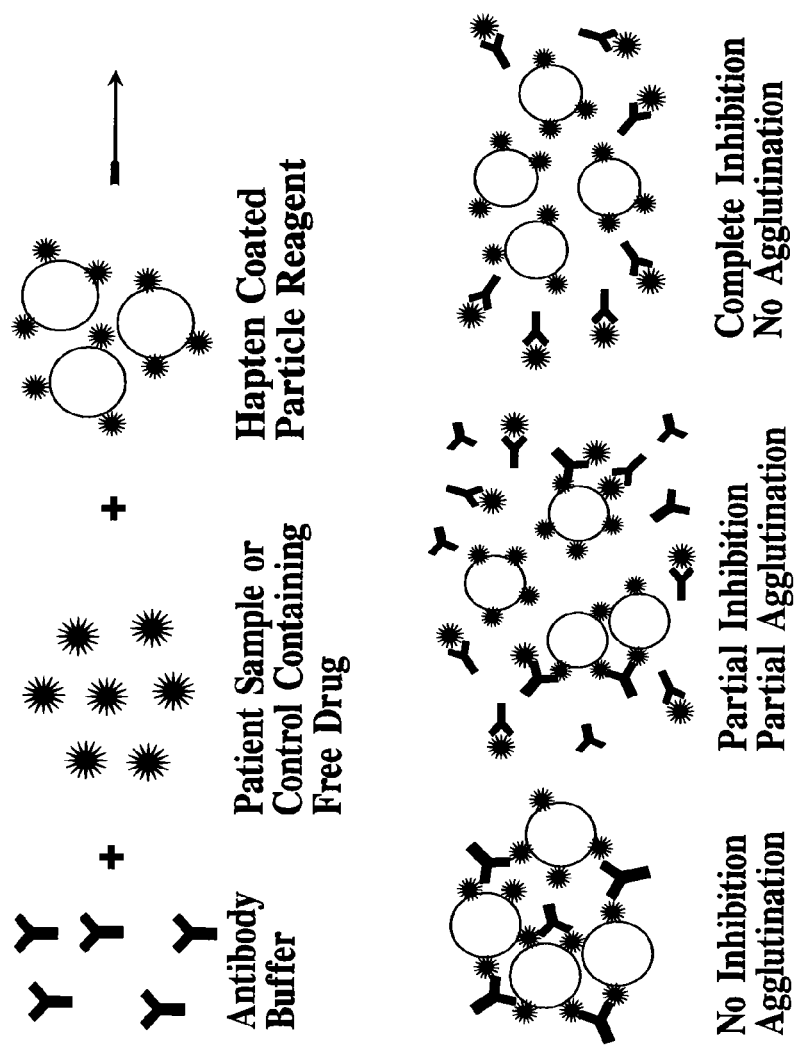
FIG. 3 is a schematic diagram illustrating an embodiment of a competitive binding study based on fluorescent polarization.
Figure 4:
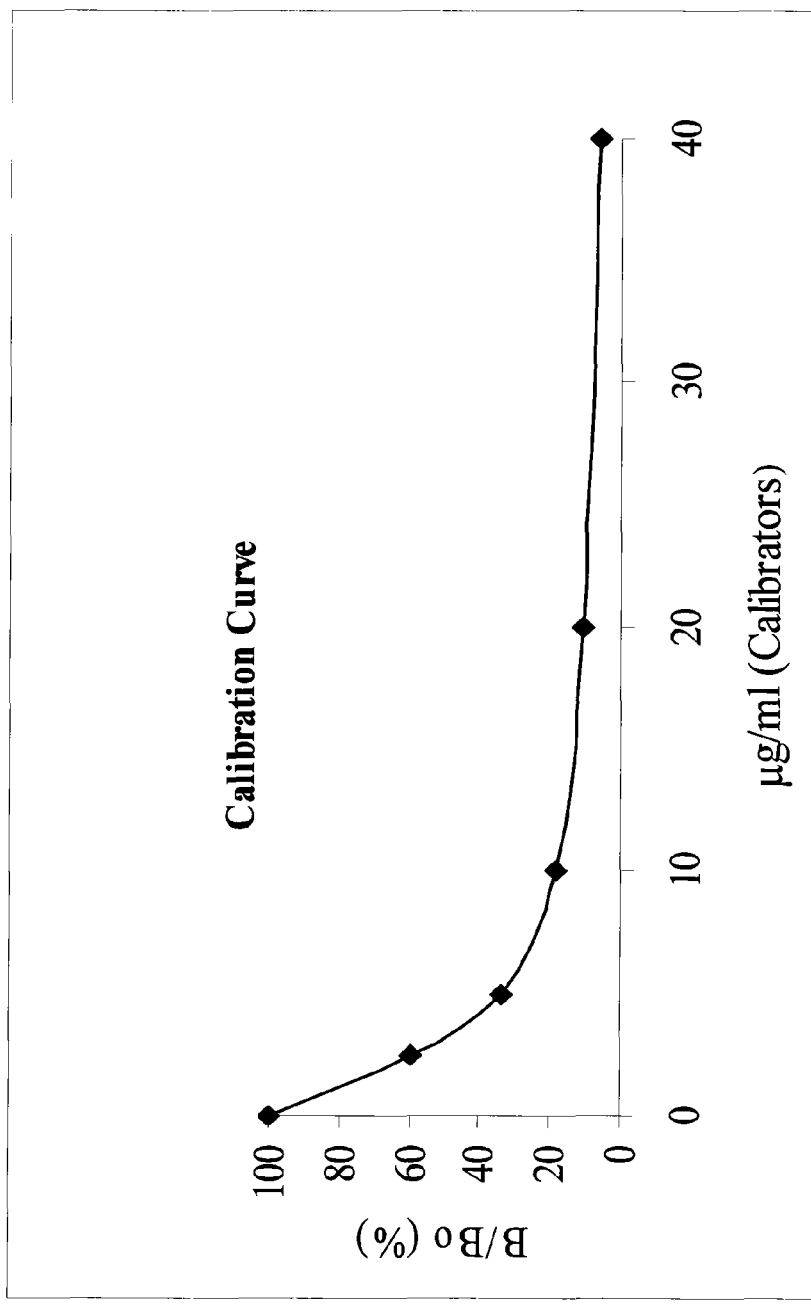
FIG. 4 is a graph illustrating an embodiment of a calibration curve for lamotrigine.

FIG. 3 is an illustration of a competition assay that combines an antibody buffer with a biological sample having a free drug, such as lamotrigine, and a hapten coated particle reagent, wherein the hapten can be a lamotrigine analog. In the instance the biological sample contains little or no lamotrigine, there is no inhibition of agglutination. As the amount of lamotrigine in the sample increases, there can be partial inhibition so as to result in only partial agglutination. Additionally, a large amount of lamotrigine in the sample can result in the complete inhibition of agglutination. Thus, the analysis of agglutination can be used to identify the presence of lamotrigine. Also, the use of a standardized curve of lamotrigine concentrations, as shown in FIG. 4, can be used to identify the amount of lamotrigine in the sample based on the absorbance change from agglutination.

i. Lamotrigine Loaded Microparticles

Figure 5:
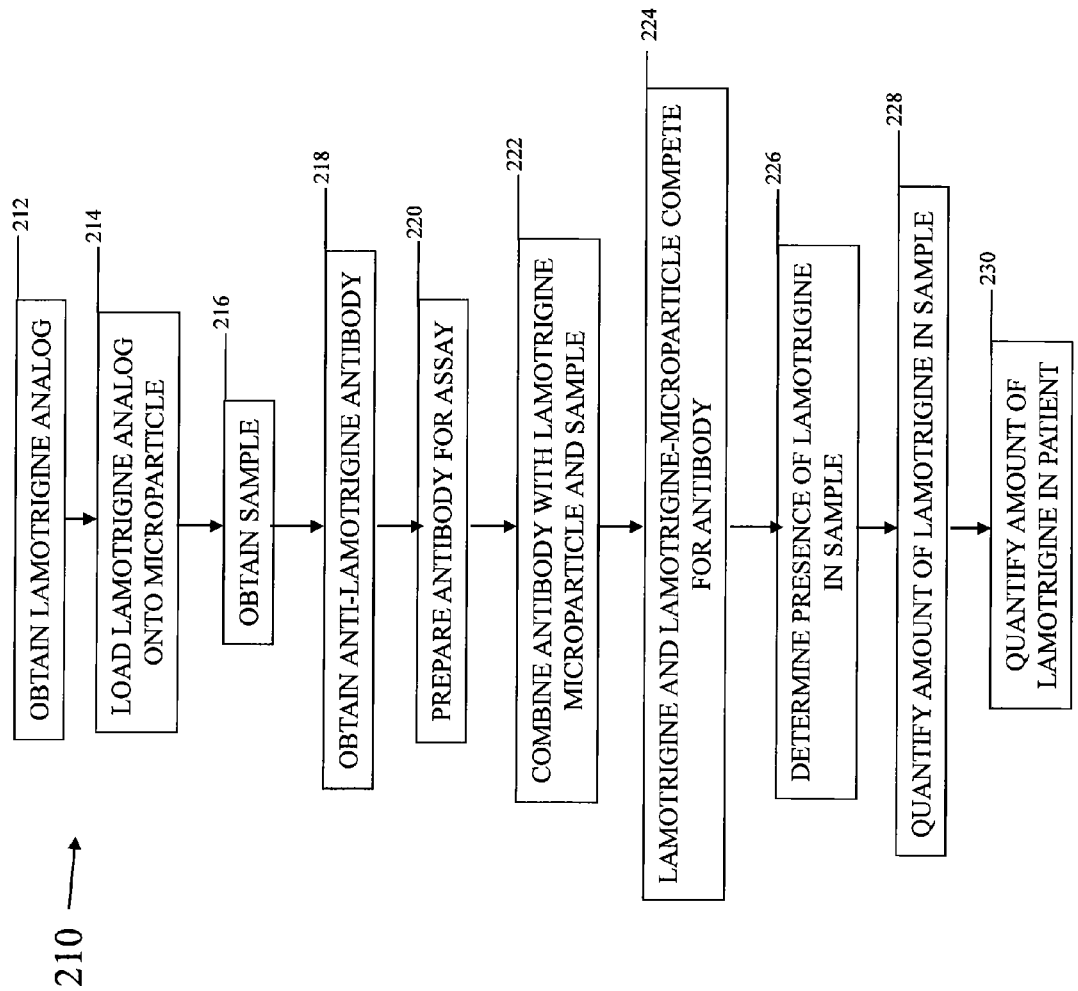
FIG. 5 is flow diagram illustrating an embodiment of a competitive binding study based on agglutination.

FIG. 5 is a flow diagram illustrating one embodiment of a method 210 for performing an HMI assay. Accordingly, lamotrigine analogs can be obtained (Block 212) and loaded on a microparticle (Block 214), such as any of the microparticles manufactured and/or sold by Seradyn, Inc. (Indianapolis, Ind.), which can include polystyrene, carboxylate-modified polystyrene, streptavidin-coated magnetic particles, and the like. A sample, such as a biological sample from a patient being administered lamotrigine, suspected of containing lamotrigine can be obtained (Block 216). An anti-lamotrigine antibody, such as monoclonal or polyclonal, capable of specifically binding lamotrigine and lamotrigine analogs in accordance with the present invention is obtained (Block 218), and then optionally formulated in a standard buffer system (Block 220). The antibody composition is then combined with the lamotrigine-microparticle and biological sample (Block 222), wherein the amounts of antibody and lamotrigine analog bound to the microparticle are known. A competitive reaction takes place between lamotrigine analog immobilized on the microparticles and the lamotrigine in the biological sample for binding to a limited amount of anti-lamotrigine antibody in the reaction solution (Block 224). Agglutination of lamotrigine-loaded microparticles with antibody is inhibited by the presence of lamotrigine in the biological sample, wherein agglutination inhibition is directly proportional to concentration of lamotrigine in the biological sample. This allows for the presence of lamotrigine in the sample to be determined by well-known turbidimetric assays (Block 226). Additionally, comparing the measurements obtained from the biological sample with standardized measurements obtained from known concentration standards can be used to quantify the amount of lamotrigine in the sample (Block 228), and thereby identify the amount of lamotrigine in the patient (Block 230).

One embodiment of the present invention is a lamotrigine loaded microparticle HMI assay system. An example of components of the HMI system can include the following: i) monoclonal or polyclonal anti-lamotrigine antibodies capable of binding lamotrigine and a lamotrigine analog; ii) a sample suspected of containing the lamotrigine; and iii) lamotrigine analog coupled to a microparticle, such as a polystyrene microparticle. Alternatively, the system can be provided as a kit without the sample. Additionally, the system can include various buffer compositions, lamotrigine concentration gradient compositions or a stock composition of lamotrigine, and the like.

ii. Anti-Lamotrigine Loaded Microparticles

In another embodiment, which is similar to that described above with respect to lamotrigine loaded microparticles, an anti-lamotrigine antibody capable of binding lamotrigine and a lamotrigine analog is loaded on the microparticle. The lamotrigine analog can include an operative group of choice, for example, bovine serum albumin, ovalbumin, dextran, and the like. A competitive reaction takes place between the lamotrigine analog and lamotrigine in the patient's sample for binding to anti-lamotrigine antibody immobilized on the microparticles. Again, agglutination of particles is inhibited by the presence of drug in patient sample.

Figure 6:
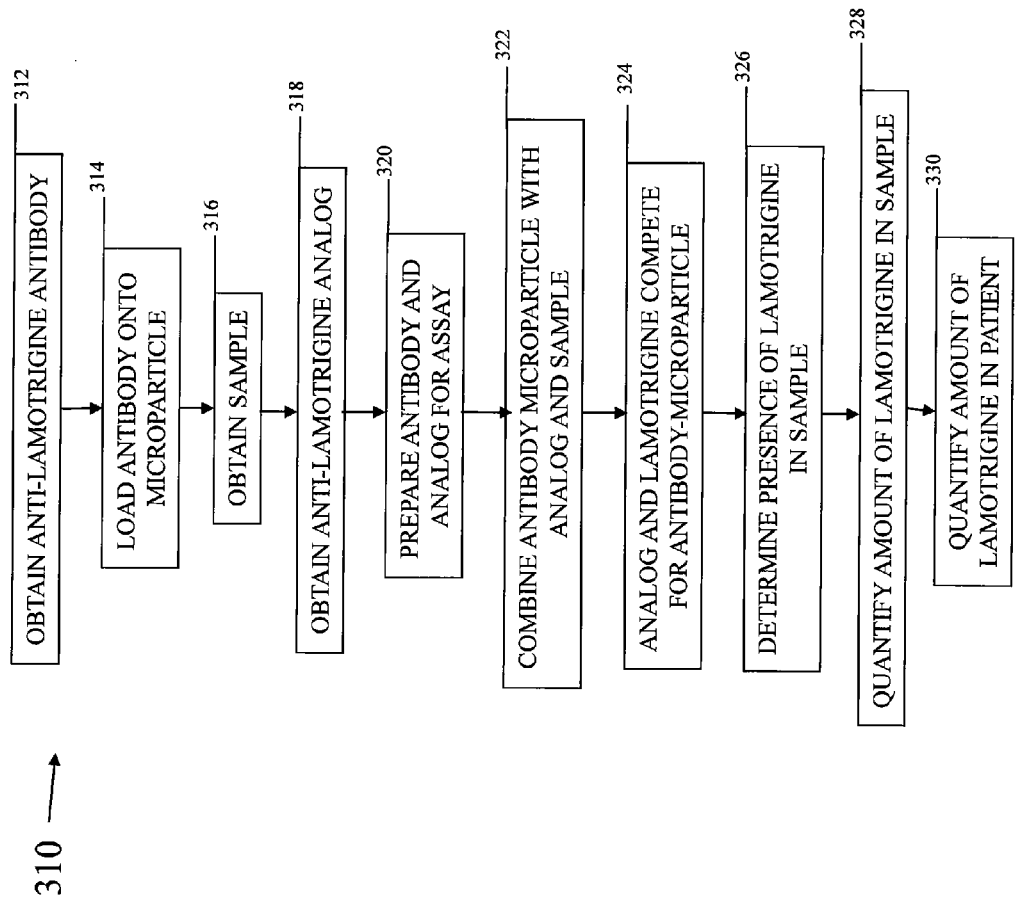
FIG. 6 is a flow diagram illustrating an embodiment of a competitive binding study based on agglutination.

FIG. 6 is a flow diagram illustrating another embodiment of a method 310 for performing an HMI assay. Accordingly, anti-lamotrigine antibodies capable of specifically binding lamotrigine and a lamotrigine analog can be obtained (Block 312) and loaded on a microparticle (Block 314). A sample, such as a biological sample from a patient being administered lamotrigine, suspected of containing lamotrigine can be obtained (Block 316). A lamotrigine analog can be obtained, where the analog can include a suitable operative group (Block 318). Known amounts or concentrations of the lamotrigine analog and anti-lamotrigine antibody-loaded microparticle are then formulated into separate compositions, such as a standard buffer system, for use in a competitive binding assay (Block 320). The antibody-microparticle composition is then combined with the lamotrigine analog composition and biological sample (Block 322). A competitive reaction takes place between the lamotrigine analog and lamotrigine in the biological sample with the anti-lamotrigine antibody immobilized on the microparticles in the reaction solution (Block 324). Agglutination of anti-lamotrigine antibody-loaded microparticles with the lamotrigine analog is inhibited by the presence of lamotrigine in the biological sample, wherein inhibition of agglutination is directly proportional to concentration of lamotrigine in the biological sample. This allows for the presence of lamotrigine in the sample to be determined by well-known turbidimetric assays (Block 326). Additionally, comparing the measurements obtained from the biological sample with standardized measurements obtained from known concentration standards can be used to quantify the amount of lamotrigine in the sample (Block 328), and thereby identify the amount of lamotrigine in the patient (Block 330)

One embodiment of the present invention is an anti-lamotrigine antibody loaded microparticle HMI assay system. An example of components of the HMI system can include the following: i) microparticles loaded with monoclonal or polyclonal anti-lamotrigine antibodies that are capable of binding to lamotrigine and a lamotrigine analog; ii) a sample suspected of containing the lamotrigine; and iii) a lamotrigine analog, which can optionally include a macromolecule or other carrier. Alternatively, the assay system can be provided exclusive of the sample, which can be provided later or from another source. Additionally, the assay system can include various buffer compositions, lamotrigine concentration gradient compositions or a stock composition of lamotrigine or analog, and the like.

C. Cloned Enzyme Donor Immunoassays for Lamotrigine

Cloned enzyme donor Immunoassays ("CEDIA®" a trademark of Roche Diagnostics) has proven to be a highly accurate and effective method for identifying the presence and performing quantitative measurements of therapeutic drugs. The CEDIA® technology has been described in detail in the following patents: (a) U.S. Pat. No. 4,708,929 disclosing competitive homogeneous assay methods; (b) U.S. Pat. No. 5,120,653 disclosing a recombinant DNA sequence for coding the enzyme donor fragment and a host for such a vector; (c) U.S. Pat. No. 5,604,091 disclosing amino acid sequences of the enzyme donor fragment; and (d) U.S. Pat. No. 5,643,734 which teaches kits for CEDIA assays, wherein all of the foregoing patents are incorporated herein by reference. Briefly, CEDIA® technology is based upon the competition of a lamotrigine in the biological sample with analog conjugated to an inactive genetically engineered enzyme-donor ("ED") fragment such as from β-D-galactoside galactohydrolase or β-galactosidase ("β gal") from *E. coli*, for binding to an antibody capable of specifically binding lamotrigine. In the instance the lamotrigine is present in the sample it binds to the antibody, leaving the ED portion of the ED-analog conjugate free to restore enzyme activity of β-D-galactoside galactohydrolase or β gal in the reaction mixture so as to be capable of association with enzyme acceptor ("EA") fragments. The active enzyme is then capable of producing a quantifiable reaction product when exposed to an appropriate substrate. A preferred substrate is chlorophenol red-β-D-galactopyranoside ("CPRG"), which can be cleaved by the active enzyme having the ED and EA fragments into galactose and CPR, wherein CPR is measured by absorbency at about wavelength 570 nm. In the instance lamotrigine is not present in the sample, the antibody binds to the ED-analog conjugate, thereby inhibiting association of the ED fragments with the EA fragments and inhibiting restoration of enzyme activity. The amount of reaction product and resultant absorbance change are proportional to the amount of lamotrigine in the sample.

Figure 7:
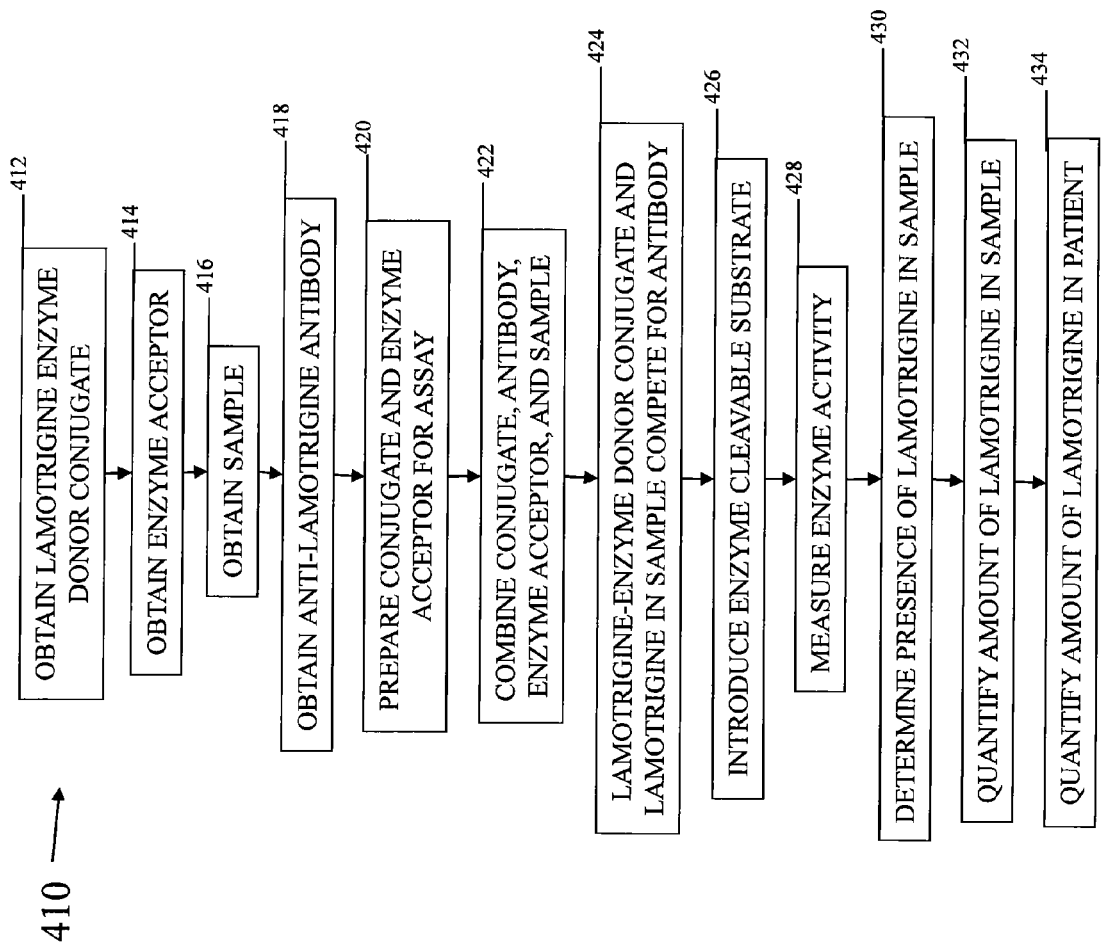
FIG. 7 is a flow diagram illustrating an embodiment of a competitive binding study based on enzymatic activity.

FIG. 7 is a flow diagram illustrating one embodiment of a method 410 for performing a CEDIA® assay. Accordingly, a lamotrigine-ED conjugate can be obtained (Block 412), which can be by conjugating a lamotrigine analog with the ED. Also, an EA corresponding with the ED can be obtained (Block 414). Additionally, a sample, such as a biological sample from a patient being administered lamotrigine, suspected of containing lamotrigine can be obtained (Block 416). Anti-lamotrigine antibody, which can also interact with the lamotrigine-ED conjugate can be obtained by methods in accordance with the present invention (Block 418). Known amounts or concentrations of lamotrigine-ED conjugate, EA, and anti-lamotrigine antibody are obtained and formulated into separate compositions, such as a standard buffer system, for use in a competitive binding assay (Block 420). The lamotrigine-ED conjugate and antibody is then combined with the biological sample into a reaction solution (Block 422). Optionally, the EA is also combined into the reaction solution at this point or later after a sufficient time for competitive interactions with the antibody to occur. A competitive reaction takes place between the lamotrigine-ED conjugate and lamotrigine in the biological sample with the anti-lamotrigine antibody in the reaction solution (Block 424). After the competitive reactions and the EA has been introduced into the reaction solution, an ED-EA enzyme-cleavable substrate is introduced into the reaction solution (Block 426). The enzyme activity between the ED-EA enzyme and enzyme-cleavable substrate is measured (Block 428), which can be by measuring the absorbance of a cleavage product or other well-known measuring technique. The measurement of enzyme activity can be used to determine whether or not lamotrigine is present in the sample (Block 430). Additionally, comparing the measurements obtained from the biological sample with standardized measurements obtained from known concentration standards can be used to quantify the amount of lamotrigine in the sample (Block 432), and thereby identify the amount of lamotrigine in the patient (Block 434).

One embodiment of the present invention is a CEDIA® assay system. An example of components of the CEDIA® system can include the following: i) monoclonal or polyclonal anti-lamotrigine antibodies capable of binding to lamotrigine, a lamotrigine analog, and/or lamotrigine-ED or lamotrigine-EA; ii) a sample suspected of containing the lamotrigine; iii) a lamotrigine analog coupled to an ED or EA; and iv) one of an ED or EA that will associate with the lamotrigine-ED or lamotrigine-EA for restoring enzymatic activity so that an ED and EA are present in the system. Alternatively, the assay system can be provided as a kit exclusive of the sample. Additionally, the assay system can include various buffer compositions, lamotrigine concentration gradient compositions or a stock composition of lamotrigine, and the like.

D. Chemiluminescent Heterogeneous Immunoassays for Lamotrigine

A competitive assay using chemiluminescent microparticle immunoassay ("CMIA") technology can also be used to assess whether or not lamotrigine is present in a sample. Various types of CMIA technologies are well known in the art of heterogeneous immunoassays for determining the presence and/or amount of a chemical entity in a sample, wherein some CMIA technologies can be exemplified by U.S. Pat. Nos. 6,448,091, 5,798,083, and 5,834,206, which are incorporated herein by reference. Such CMIA assays can include the use of anti-lamotrigine antibodies, which are capable of specifically binding to lamotrigine and it analogs, coupled to particles, such as particular magnetic particles or particles suitable for separation by filtration, sedimentation, and/or other means. Additionally, a tracer, which can include a lamotrigine analog linked to a suitable chemiluminescent moiety, for example an acridinium ester, can be used to compete with free lamotrigine in the patient's sample for the limited amount of anti-lamotrigine antibody on the particle. After the sample, tracer, and antibody particles interact and a routine wash step has removed unbound tracer, the amount of tracer bound to antibody particles can be measured by chemiluminescence, wherein chemiluminescence is expressed in Relative Light Units (RULE). The amount of chemiluminescence is inversely related to the amount of free drug in the patient's sample and concentration is determined by constructing a standard curve using known values of the drug.

Figure 8:
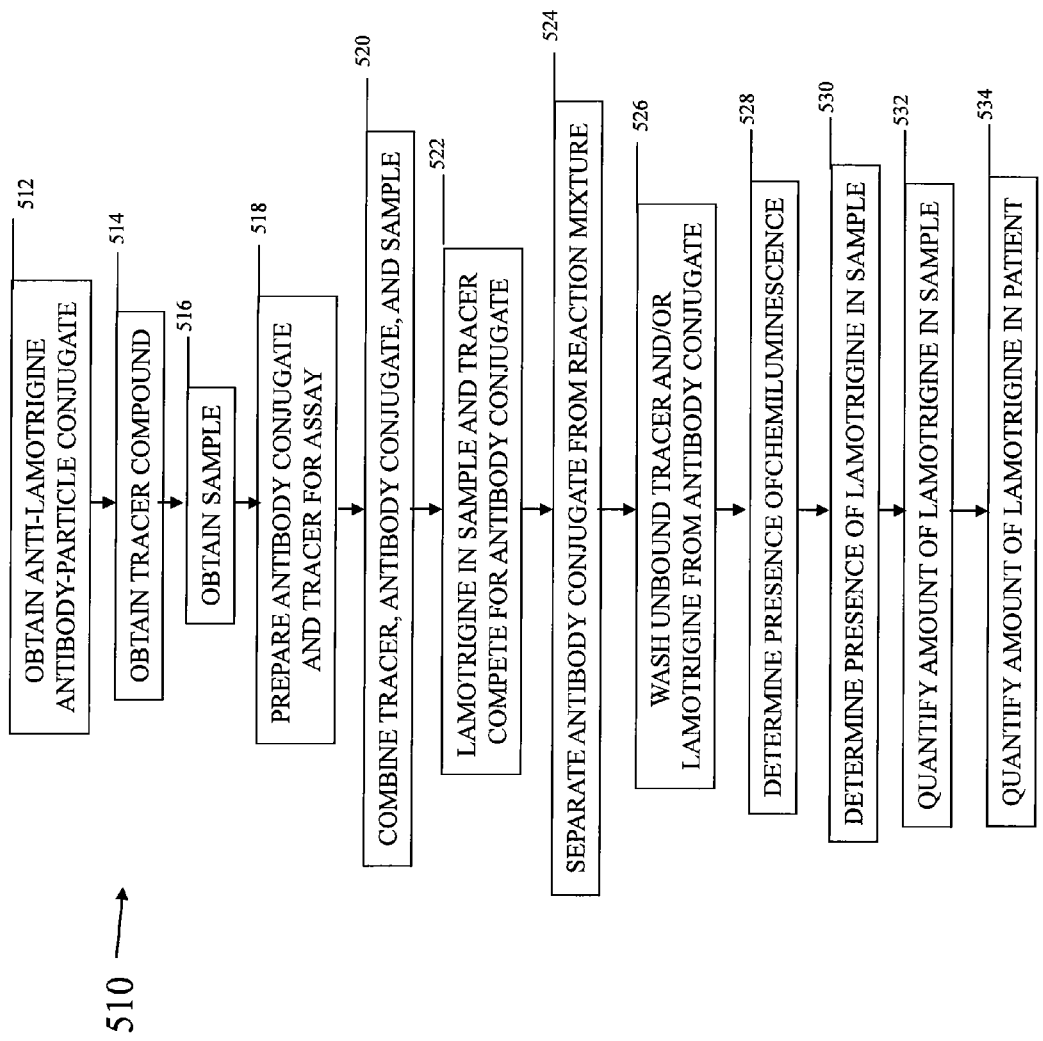
FIG. 8 is a flow diagram illustrating an embodiment of a competitive binding study based on chemiluminescence.

FIG. 8 is a flow diagram illustrating one embodiment of a method 510 for performing a CMIA assay. Accordingly, an anti-lamotrigine antibody-particle conjugate can be obtained (Block 512), which can be performed by coupling the antibody with a particle such as a magnetic particle. Also, a tracer compound including a lamotrigine analog having a chemiluminescent moiety can be obtained (Block 514). Additionally, a sample, such as a biological sample from a patient being administered lamotrigine, suspected of containing lamotrigine can be obtained (Block 516). Known amounts or concentrations of tracer and anti-lamotrigine antibody-particle conjugate can be formulated into separate compositions, such as a standard buffer system, for use in a competitive binding assay (Block 518). The anti-lamotrigine antibody-particle conjugate and tracer is then combined with the biological sample into a reaction solution (Block 520). A competitive reaction takes place between the tracer and lamotrigine in the biological sample with the anti-lamotrigine antibody-particle conjugate in the reaction solution (Block 522). After sufficient duration and/or binding competition, the antibody-particle conjugate is separated from the reaction solution (Block 524). Optionally, any unbound lamotrigine and/or tracer can be removed from the antibody-particle conjugate by a wash or other separation technique (Block 526). The amount of chemiluminescence can be determined by exciting the tracer so that the chemiluminescent moiety emits light by phosphorescence, fluorescence, or other luminescence which is measurable (Block 528). Often, the chemiluminescence is fluorescence, which is measured in RLUs. The measurement of chemiluminescence can be used to determine whether or not lamotrigine is present in the sample (Block 530). Additionally, comparing measurements obtained from the biological sample with standardized measurements obtained from known concentration standards can be used to quantify the amount of lamotrigine in the sample (Block 532), and thereby identify the amount of lamotrigine in the patient (Block 534).

One embodiment of the present invention is a CMIA assay system. An example of components of the CMIA system can include the following: i) particles or microparticles loaded with monoclonal or polyclonal anti-lamotrigine antibodies that are capable of binding to lamotrigine and a lamotrigine analog; ii) a sample suspected of containing the lamotrigine; and iii) an analog tracer. Alternatively, the assay system can be provided as a kit exclusive of the sample. Additionally, the system can include various buffer compositions, lamotrigine concentration gradient compositions or a stock composition of lamotrigine or analog, and the like.

E. Other Immunoassays for Lamotrigine

The lamotrigine analogs, conjugates, antibodies, immunogens and/or other conjugates described herein are also suitable for any of a number of other heterogeneous immunoassays with a range of detection systems including but not limited to enzymatic or fluorescent, and/or homogeneous immunoassays including but not limited to rapid lateral flow assays, and antibody arrays, as well as formats yet to be developed.

While various immunodiagnostic assays have been described herein that utilize the lamotrigine analogs, conjugates, antibodies, immunogens and/or tracers, such assays can also be modified as is well known in the art. As such, various modifications of steps or acts for performing such immunoassays can be made within the scope of the present invention.

EXAMPLES

The following examples are provided to illustrate embodiments of the prevention and are not intended to be limiting. Accordingly, some of the examples have been performed via experiment and some are prophetic based on techniques, standards, and results well known in the art. Also, it should be apparent that the invention can include additional embodiments not illustrated by example. Additionally, many of the examples have been performed with experimental protocols well known in the art using the lamotrigine analogs, antigens, immunogens, and anti-lamotrigine antibodies prepared in accordance with the present invention. Thus, the examples can be supplemented with the following references, which are all incorporated herein by reference: (a) Caryl Griffin et al., *Microparticle Reagent Optimization: A Laboratory Reference Manual from the Authority on Microparticles*, Seradyn (1994); and (b) Boehringer Mannheim Corporation Technical Publications Department, *Hitachi Operation Manual Version B*, Boehringer Mannheim Corporation Laboratory Diagnostic Division (1992); and (c) the NCCLS, approved guideline Aug. 2004.

Example 1

Figure 9:
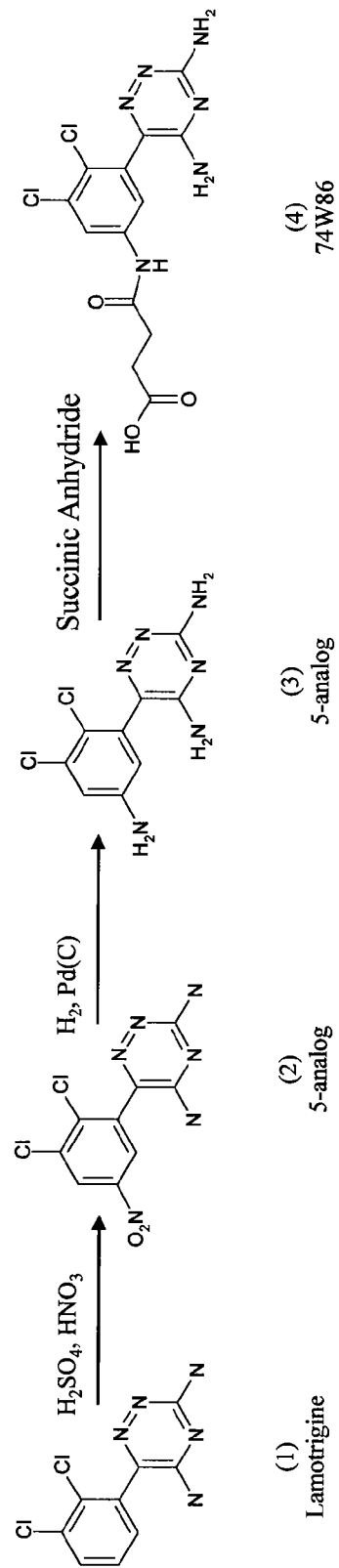
FIG. 9 is a schematic diagram illustrating an embodiment of a synthesis protocol for synthesizing a lamotrigine analog.

FIG. 9 is a schematic representation of a chemical reaction for converting lamotrigine (1) into 5-intermediates and a 5-succinylamino lamotrigine derivative ("74W86") (4), which can be further synthesized into various lamotrigine analogs in accordance with the present invention. Accordingly, lamotrigine (1) is treated with a mixture of nitric acid and sulfuric acid to form 5-nitro lamotrigine analog (2). The 5-nitro lamotrigine analog (2) is then isolated and reduced with hydrogen and Pd catalyst to form the resulting 5-amino lamotrigine analog (3), which is acylated with succinic anhydride to form the 5-succinylamino derivative of lamotrigine, ("74W86") (4). The 5-succinylamino derivative of lamotrigine, ("74W86") (4) is then purified.

Example 2

FIG. 10 is a schematic representation of a chemical reaction for converting 74W86 (4) into an NHS-active ester form in order to improve the efficiency of coupling to carrier proteins and the like. Accordingly, 74W86 (4), obtained via the chemistry described in Example 1, is modified with NHS to obtain the activated ester derivative of lamotrigine, which is 5-NHS-74W86 (5). The active ester 5-NHS-74W86 (5) can be efficiently coupled to a carrier protein or other moiety since it reacts directly with the amine of lysine within the protein, and other amine groups. Also, 5-NHS-74W86 (5) can be coupled to linking groups that have already been conjugated to a carrier protein, wherein the linker includes an amine group to form an amide linking group.

Specifically, a solution of 745 mg of 74W86 (4) in 25 mL anhydrous DMF is cooled to 0° C., and 0.7 mL N,N-diisopropylethyl amine is added to form a reaction mixture. The reaction mixture is reacted by the addition of 785 mg of O-(N-succinimidyl)-N,N,N',N'-tetramethyluronium tetrafluoroborate. The reaction mixture is allowed to warm up to room temperature and stirred overnight. The reaction mixture is concentrated under reduced pressure, and the residue is purified by flash column chromatography using ethyl acetate/methanol as eluent to give approximately 500 mg of active ester derivative 5-NHS-74W86 (5).

Example 3

With continuing reference to FIG. 10, the 5-NHS-74W86 (5) lamotrigine analog, which is obtained via the chemical reaction of Example 2, is conjugated with a linking group. More specifically, the 5-NHS-74W86 (5) analog is reacted with an alkyldiamine, such as ethylenediamine, to produce a lamotrigine analog 5-ethylenediamine 74W86 (6). The reaction is performed by adding 0.5 mL of ethylenediamine to a solution of 300 mg of 5-NHS-74W86 (5) in 3 mL anhydrous DMF to form a reaction mixture. The reaction mixture is stirred at room temperature overnight and concentrated until dry under reduced pressure. The dried residue is purified by flash column chromatography using methanol/ammonium hydroxide as eluent to give approximately 200 mg lamotrigine analog 5-ethylenediamine 74W86 (6). The 5-ethylenediamine 74W86 (6) can be activated for conjugation with additional linking groups or reacted directly with carboxyl groups on other molecules.

Example 4

With continuing reference to FIG. 10, the 5-ethylenediamine 74W86 (6) lamotrigine analog, which is obtained via the chemical reaction of Example 3, is further conjugated with a linking group. More specifically, 5-ethylenediamine 74W86 (6) is acylated by being reacted with succinic anhydride to form a 5-lamtorigine analog (7). The reaction is conducted with about 0.2 mL N,N-diisopropylethyl amine being added to a suspension of 75 mg of lamotrigine derivative (6) in 5 mL anhydrous DMF to form a reaction mixture. The reaction mixture is stirred for 5 min followed by the addition of 83 mg of succinic anhydride. The reaction mixture is stirred for 2 h and concentrated until dry under reduced pressure. The dry residue is purified by flash column chromatography using methanol/ethyl acetate as eluent to give approximately 200 mg 5-lamotrigine analog (7).

Example 5

With continuing reference to FIG. 10, the 5-ethylenediamine 74W86 (6) lamotrigine analog, which is obtained via the chemical reaction of Example 3, is further conjugated with a linking group. More specifically, 5-ethylenediamine 74W86 (6) is acylated by reaction with disuccinimidyl suberate ("DSS") to form the 5-lamotrigine analog (8). The reaction is conducted with about 0.2 mL N,N-diisopropylethyl amine being added to a solution of 2 g of DSS in 6 mL DMF that is chilled in an ice bath, and followed by addition of a suspension of 327 mg of 5-ethylenediamine 74W86 (6) in 15 mL anhydrous DMF to form a reaction mixture. The reaction mixture is stirred for 4 h and concentrated until dry under reduced pressure. The residue is purified by flash column chromatography using methanol/ethyl acetate as eluent to give approximately 350 mg 5-lamotrigine analog (8).

Example 6

With continuing reference to FIG. 10, the 5-NHS-74W86 (5) lamotrigine analog, is further conjugated with a linking group. Accordingly, in a round bottom flask containing a magnetic stirrer, about 59 mg of 5-NHS-74W86 (5) and 40 mg of methyl 4-aminomethyl benzoate hydrochloride are combined. About 2 mL of anhydrous DMF and 0.1 ml of N,N-diisopropylethylamine are added to the flask, and stirred under Ar in a 60° C. oil bath. The reaction is stopped after 24 h. The volatiles are evaporated under reduced pressure and the residue is purified by flash column chromatography using ethyl acetate/methanol as eluent to give 20 mg lamotrigine analog (9).

Example 7

FIG. 11 is a schematic representation of a chemical reaction for converting lamotrigine into 4-intermediates and 4-succinylamino lamotrigine. Accordingly, lamotrigine is treated with a mixture of nitric acid and sulfuric acid to form 4-nitro lamotrigine (10). The 4-nitro lamotrigine (10) intermediate is isolated and reduced with hydrogen via a Pd catalyst to form a 4-amino lamotrigine (11) intermediate, which is then acylated with succinic anhydride to form the 4-succinylamino lamotrigine (12) analog. The 4-succinylamino lamotrigine (12) analog is purified, and then can be further reacted with linker groups or carrier moieties in order to form analogs and conjugates in accordance with the present invention.

Example 8

With continuing reference to FIG. 11, the 4-succinylamino lamotrigine (12) analog is reacted with NHS to form an activated ester such as 4-NHS-succinylamino lamotrigine (13) analog. Accordingly, the 4-succinylamino lamotrigine (12) analog is reacted with NHS under reaction conditions substantially similar as in Example 2. The 4-NHS-succinylamino lamotrigine (13) analog is then purified.

Example 9

FIG. 12 is a schematic representation of a chemical reaction for converting lamotrigine into 3-intermediates and 3-succinyl lamotrigine (14). Accordingly, about 1.0 mL N,N-diisopropylethyl amine is added to a solution of 2 g of lamotrigine in 30 mL anhydrous DMF. The mixture is stirred for 5 min followed by the addition of 600 mg of succinic anhydride to form a reaction mixture. The reaction mixture is stirred overnight and concentrated until dry under reduced pressure. The dry residue is purified by flash column chromatography using methanol/ammonium hydroxide as eluent to yield approximately 1 g of 3-succinyl lamotrigine (14), which is characterized by Formula 4A with the following: L is NH.

Example 10

With continuing reference to FIG. 12, the 3-succinyl lamotrigine (14) is modified to an active ester. Accordingly, a solution of 400 mg of 3-succinyl lamotrigine (14) in 20 mL anhydrous DMF is cooled to 0° C., and 0.3 mL N,N-diisopropylethyl amine is added to form a reaction mixture. Subsequently, about 450 mg of O-(N-succinimidyl)-N,N,N',N'-tetramethyluronium tetrafluoroborate is added to the reaction mixture. The reaction mixture is allowed to warm up to room temperature and stirred for 4 h. The reaction mixture is then concentrated to obtain a dry residue under reduced pressure, and the dry residue is purified by flash column chromatography using ethyl acetate/methanol as eluent to yield approximately 235 mg of 3-NHS-succinyl lamotrigine (14).

Example 11

Figure 13A:
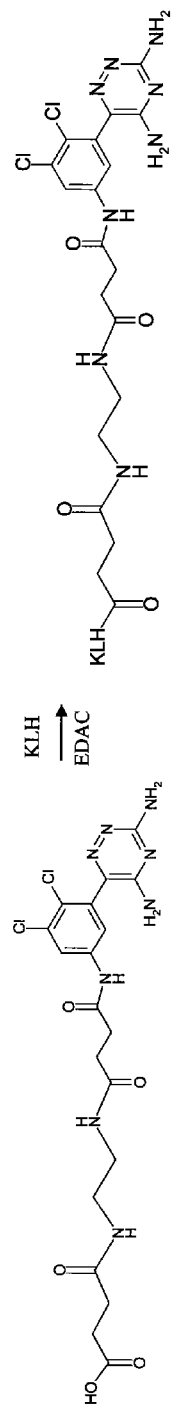
FIGS. 13A-13E are schematic diagrams illustrating embodiments of synthesis protocols for synthesizing a lamotrigine-based immunogens.

FIGS. 13A-13D are schematic representations of chemical reactions for converting lamotrigine analogs to lamotrigine analog conjugates, which can be used as immunogens to produce anti-lamotrigine antibodies and to produce conjugates for use in various immunodiagnostic assays as described herein. More particularly, active esters of lamotrigine analogs (7), (13), (15) and (8) can be coupled to immunogenic carrier proteins, such as keyhole limpet hemocyanin ("KLH"). FIG. 13A is an schematic diagram illustrating an exemplary synthesis method used to form immunogen (16), which is a 5-KLH-lamotrigine analog conjugate having a long linker. The reaction is conducted by cooling a solution of 80 mg of KLH in 8 ml PBS (0.1 M sodium phosphate, 0.15 M sodium chloride pH 7.2) in an ice bath. Next, a solution of 18 mg of 5-lamotrigine analog (7) in 1 mL PBS buffer PH 7.2 is added to the protein solution drop-wise to form a reaction mixture. The reaction mixture is allowed to stir at room temperature for 10 minutes then 60 mg ED AC [1-ethyl-3-(3- dimethylaminopropyl) carbodiimide hydrochloride] in 0.5 mL DI water is added and stirred for 30 minutes. The resulting conjugate is placed in a dialysis tube (10,000 MW cut-off), and dialyzed PBS in pH 7.2 at 4° C., which is then followed by five changes with PBS at pH 7.2 (1 L each for at least 6 hours each). The protein concentration of the resulting immunogen (16) is determined using a BCA assay.

Example 12

Figure 13B:
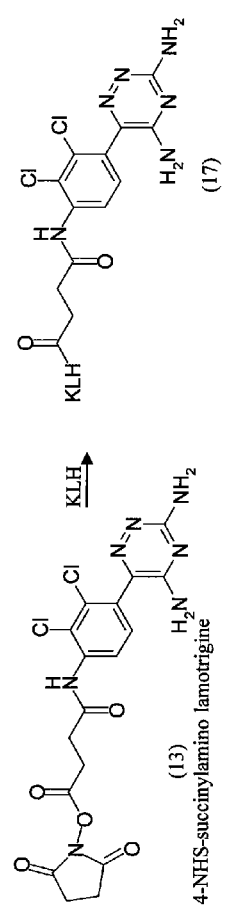

FIG. 13B is a schematic diagram illustrating an alternative chemical reaction to provide an additional immunogen (17). A solution of 60 mg of KLH in 6 mL PBS at pH 7.2 (0.1 M sodium phosphate, 0.15 M sodium chloride) is cooled in an ice bath before 3.8 mL of DMSO is added to the KLH solution drop-wise, and maintained below room temperature. A solution of 17.4 mg of lamotrigine analog (13) in 1 mL DMSO is added to the protein solution drop-wise to form a reaction mixture. The reaction mixture is allowed to stir at room temperature for 40 h. The resulting conjugate, 4-KLH immunogen (17), is placed in a dialysis tube (10,000 MW cut-off) and dialyzed in serial dialysis baths of 1 L of 35% DMSO in pH 7.2 PBS, 1 L of 10% DMSO in pH 7.2 PBS, and 1 L of 10% DMSO in PBS at room temperature, which is then followed by four changes with PBS at 4° C. (1 L each for at least 6 hours each). The immunogen (17) can be used in preparing monoclonal and polyclonal antibodies that can interact and bind with lamotrigine and lamotrigine analogs by methods described herein and well known in the art.

Example 13

Figure 13C:
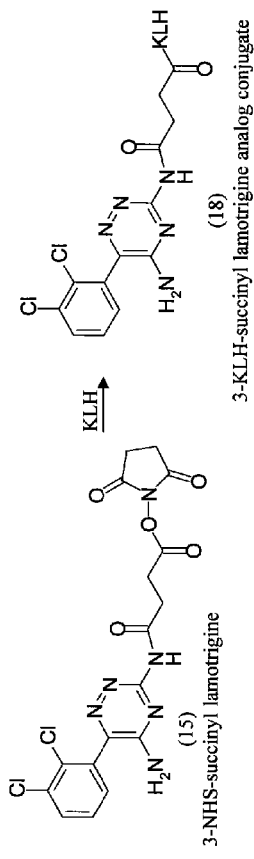

FIG. 13C is a schematic diagram illustrating an alternative chemical reaction to provide an additional immunogen (18). As such, a solution of 60 mg of KLH in 6 mL PBS at pH 7.2 (0.1 M sodium phosphate, 0.15 M sodium chloride) is cooled in an ice bath before 3.8 mL of DMSO is added to the KLH solution drop-wise, and maintained below room temperature. A solution of 12.7 mg of lamotrigine analog (15) in 1 mL DMSO is added to the protein solution drop-wise to form a reaction mixture. The reaction mixture is allowed to stir at room temperature for 40 h. The resulting conjugate is placed in a dialysis tube (10,000 MW cut-off) and serially dialyzed in 1 L of 35% DMSO in PBS at pH 7.2, 1 L of 10% DMSO in PBS at pH 7.2, 1 L of 10% DMSO in PBS at pH 7.2 at room temperature, which is followed by four changes with PBS at pH 7.2 at 4° C. (1 L each for at least 6 hours each). The protein concentration of immunogen (18) is determined as approximately 2.17 mg/mL using BCA assay. The resulting immunogen (18), and other immunogens prepared with similar chemical reactions, can be used to produce monoclonal and/or polyclonal antibodies by methods described herein and well known in the art.

Example 14

Figure 13D:
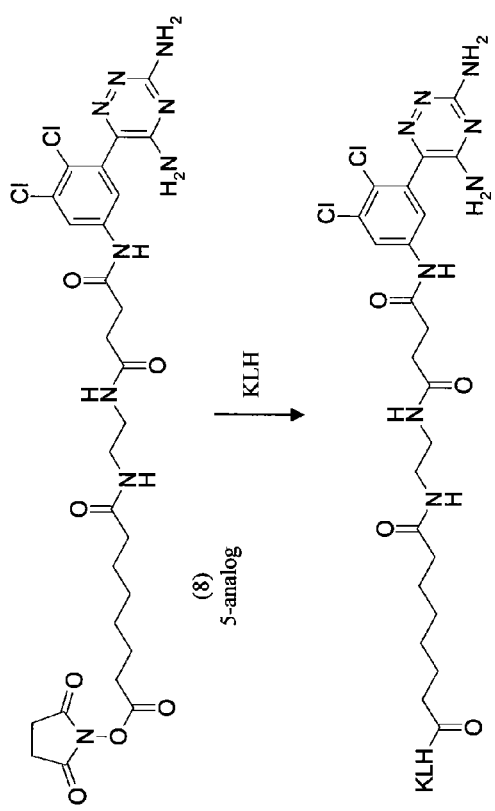

FIG. 13D is a schematic diagram illustrating an alternative chemical reaction to provide an additional immunogen (19). Accordingly, a reaction scheme substantially similar to the reactions described in Examples 11-13 can be employed with lamotrigine analog (8) as the starting material. Briefly, a solution of 60 mg of KLH in 6 mL PBS at pH 7.2 (0.1 M sodium phosphate, 0.15 M sodium chloride) is cooled in an ice bath, and 3.8 mL of DMSO are added to the KLH solution drop-wise and maintained below room temperature. A solution of 17.4 mg of lamotrigine derivative (8) in 1 mL DMSO is added to the protein solution drop-wise to form a reaction mixture. The reaction mixture is stirred at room temperature for 40 h. The resulting conjugate, 5-KLH analog (19), is placed in a dialysis tube (10,000 MW cut-off) and dialyzed in 1 L of 35% DMSO in PBS at pH 7.2, 1 L of 10% DMSO in PBS at pH 7.2, 1 L of 10% DMSO in PBS at pH 7.2 at room temperature, and followed by four changes with PBS at pH 7.2 at 4° C. (1 L each for at least 6 hours each). The resulting 5-immunogen (19), and other immunogens prepared with similar chemical reactions, can be used to produce monoclonal and/or polyclonal antibodies by methods described herein and well known in the art.

Example 15

Figure 13E:
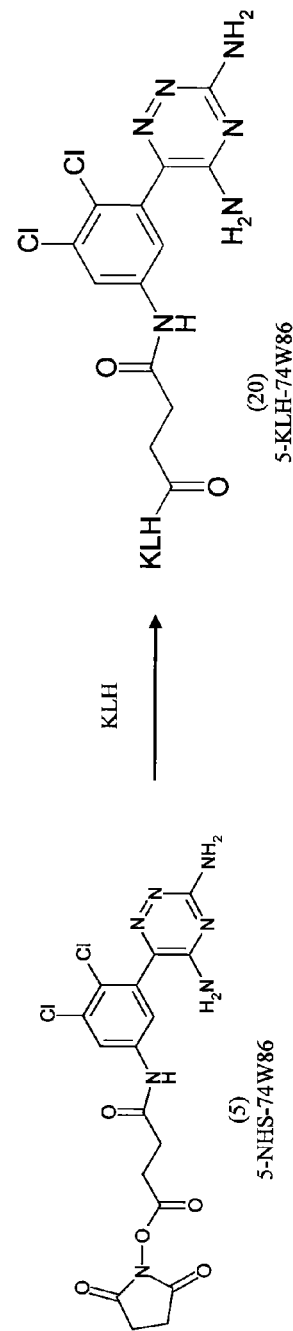

Additionally, FIG. 13E is a schematic diagram illustrating a similar reaction scheme to those described in Examples 10-13 can be employed with lamotrigine analog (5) to make a corresponding immunogen (20). However, it has been determined that the immunogen (19) has a short linker at the 5-position, which has resulted in data that shows to yield poor results possibly due to the polar nature of 74W86-immunogens.

Example 16

FIG. 14A is a schematic representation of a chemical reaction for converting a lamotrigine analog to a lamotrigine analog conjugate, which can be used as antigens, competitors, and immunogens for producing anti-lamotrigine antibodies in various immunodiagnostic assays as described herein. Accordingly, a reaction scheme substantially similar to the reactions described in Examples 11-14 can be employed with lamotrigine analog (8) as the starting material. Briefly, a solution of 60 mg of BSA in 6 mL PBS at pH 7.2 (0.1 M sodium phosphate, 0.15 M sodium chloride) is cooled in an ice bath, and 3.8 mL of DMSO are added to the KLH solution drop-wise and maintained below room temperature. A solution of 18.2 mg of lamotrigine derivative (8) in 1 mL DMSO is added to the protein solution drop-wise to form a reaction mixture. The reaction mixture is stirred at room temperature for 40 h. The resulting conjugate, 5-BSA analog (19), is placed in a dialysis tube (10,000 MW cut-off) and serially dialyzed in 1 L of 35% DMSO in PBS at pH 7.2, 1 L of 10% DMSO in PBS at pH 7.2, 1 L of 10% DMSO in PBS at pH 7.2 at room temperature, and followed by four changes with PBS at pH 7.2 at 4° C. (1 L each for at least 6 hours each). The resulting 5-BSA conjugate (21), can be used as "competitors" in heterogeneous and homogeneous immunodiagnostic assays as described herein, as well as in ELISA screening and other immunoassays. Also, immunogens (21) can be used for preparing anti-lamotrigine antibodies in accordance with the present invention, especially when the BSA moiety is substituted with a KLH moiety.

Example 17

FIG. 14B is a schematic representation of chemical reaction for converting the 4-NHS-succinylamino lamotrigine analog (13) to an antigen that can interact with an anti-lamotrigine antibody. Accordingly, the 4-lamotrigine analog (13) can be reacted with carrier protein, such as BSA or HSA, in order to form a 4-BSA conjugate or antigen (22), as shown. The synthesis protocol can be substantially similar to the reaction described in Example 16.

Example 18

Figure 14C:
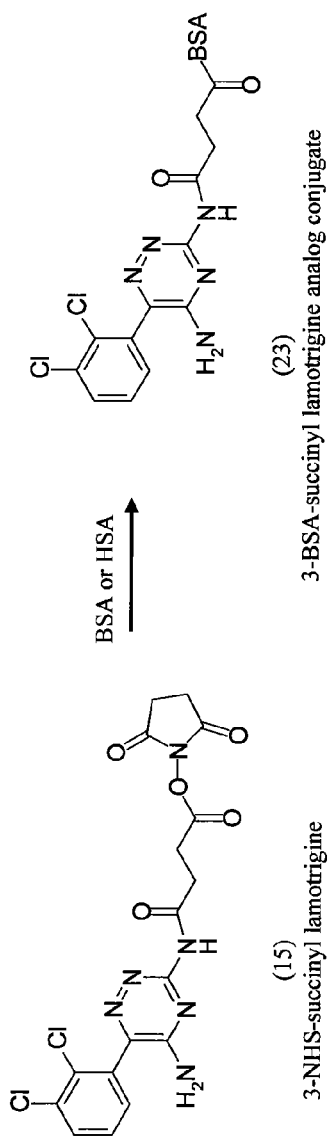

FIG. 14C is a schematic representation of chemical reaction for converting the 3-NHS-succinyl lamotrigine analog (5) to a 3-BSA conjugate or antigen (23), as shown. The synthesis protocol can be substantially similar to the reaction described in Example 16.

Example 19

Figure 14D:
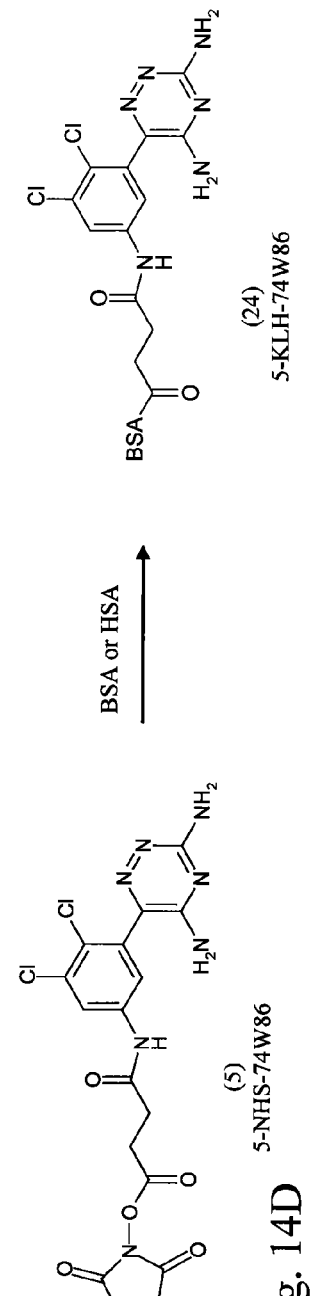

FIG. 14D is a schematic representation of chemical reaction for converting the 5-NHS-succinyl lamotrigine analog (14) to a 5-BSA conjugate or antigen (24), as shown. The synthesis protocol can be substantially similar to the reaction described in Examples 16, 17, and 18. However, it has been determined that the antigen (24) has a short linker at the 5-position, which has resulted in data that shows to yield poor results possibly due to the polar nature of 74W86-antigens.

Example 20

Figure 15A:
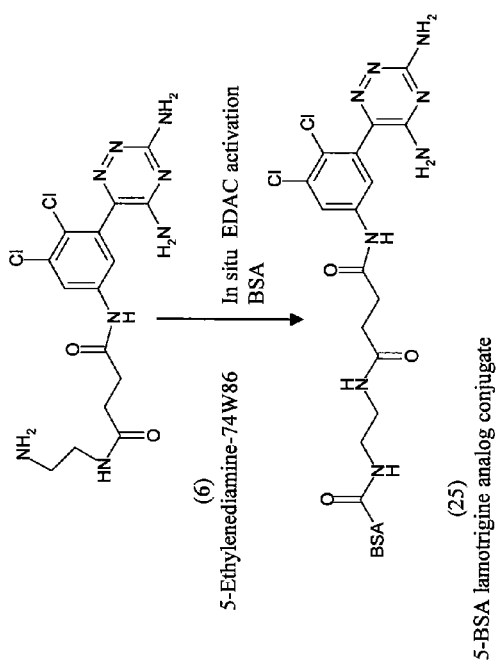
FIGS. 15A-15B are schematic diagrams illustrating embodiments of synthesis protocols for synthesizing a lamotrigine-based antigens.

FIG. 15A is a schematic representation of a chemical reaction for converting a lamotrigine analog to a lamotrigine analog antigen (25). Carboxylate groups (aspartic acid, glutamic acid) in proteins may be derivatized through the use of amide bond forming agents or through reactive carbonyl intermediates. Accordingly, a carrier protein such as BSA or HSA can be activated with 1-ethyl-3-(3-dimethylaminopropyl) carbodiimide hydrochloride ("EDAC"), as described in more detail below, in order to form an active intermediate of the actived BSA or HSA. The active intermediate can then be coupled to lamotrigine analog (6), in order to form a 5-BSA conjugate or antigen (25). The reaction is conducted by cooling a solution of 51 mg of BSA in 4 mL PBS (0.1 pH 7.2 M sodium phosphate, 0.15 M sodium chloride) in an ice bath and the solution is allowed to stir in an ice bath for 30 min. Subsequently, 1 mL of DMSO and 10 mg of lamotrigine analog (6) in 0.4 ml DMSO is added dropwise to the BSA solution. The solution is allowed to warm to room temperature while stirring. A solution of 25 mg of EDAC in 0.4 mL DI water is added to the above BSA protein solution. The solution is stirred for 4 hours. The resulting conjugate is placed in a dialysis tube (10,000 MW cut-off) and serially dialyzed in 1 L of 30% DMSO in PBS at pH 7.2, 1 L of 10% DMSO in PBS at pH 7.2, 1 L of 10% DMSO in PBS at pH 7.2 at room temperature, and followed by four changes with PBS at pH 7.2 at 4° C. (1 L each for at least 6 hours each). The protein concentration of the resulting immunogen (25) is determined using BCA assay to be about 6.4 mg/ml.

Example 21

Figure 15B:
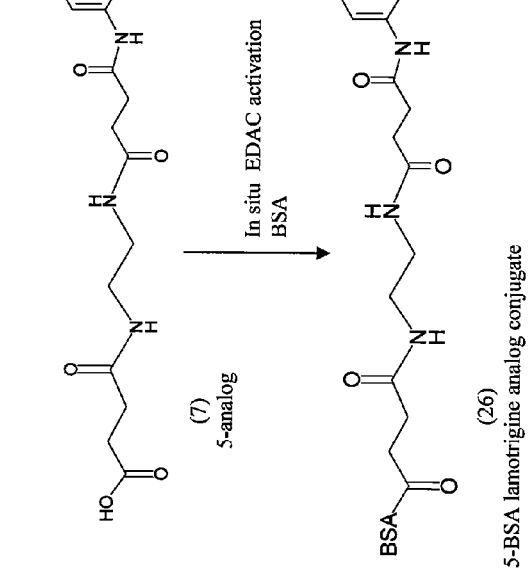

FIG. 15B is a schematic representation of chemical reactions for converting lamotrigine analog (7) to lamotrigine analog antigen (26). Accordingly, lamotrigine analog (7) can be coupled to carrier protein in situ via EDAC activation. The resulting immunogens or conjugates (26) can be used as competitor in heterogeneous and homogeneous immunodiagnostic assays as described herein, as well as in ELISA screening and other immunoassays. Also, immunogens (26) can be used for preparing anti-lamotrigine antibodies in accordance with the present invention, especially when the BSA moiety is substituted with a KLH moiety. Accordingly, a 5-lamotrigine analog (7) can be reacted with EDAC, as described in more detail below, in order to form an active intermediate of the 5-lamotrigine analog (7). The active intermediate can then be coupled to a carrier protein, such as BSA or HSA, in order to form a 5-BSA conjugate or antigen (26), as shown. The reaction is conducted by cooling a solution of 51 mg of BSA in 5 mL PBS (0.1 pH 7.2 M sodium phosphate, 0.15 M sodium chloride) in an ice bath and the solution is maintained below room temperature. Subsequently, a solution of 12 mg of 5-lamotrigine analog (7) in 1 mL PBS pH 7.2 buffer is added to the protein solution drop-wise. The solution is stirred for 10 min then is added 40 mg EDAC in 0.5 mL DI water. The reaction mixture is allowed to stir at room temperature for 30 minutes. The resulting conjugate is placed in a dialysis tube (10,000 MW cut-off), and dialyzed in 1 L×7 of 100% PBS in pH 7.2 at 4° C. at room temperature, which is then followed by five changes with PBS at pH 7.2 (1 L each for at least 6 hours each). The protein concentration of the resulting conjugate (26) is determined using BCA assay to be about 6.9 mg/ml.

FIG. 22

FIG. 16A is a schematic diagram illustrating a chemical reaction for coupling a lamotrigine analog (2) with a fluorescent label, such as FITC. In a round bottom flask wrapped with aluminum foil, a reaction solution of 10 mg FITC (Fluoresceine-5-isothiocyanate), 0.1 ml N,N-diisopropylethylamine and 8 mg of lamotrigine analog (2) is formed. The reaction solution is stirred for 18 hours, and the volatiles are evaporated under reduced pressure. The residue is re-dissolved in methanol and purified from preparative TLC plates using solvent ethyl acetate/methanol. The tracer (27) is dissolved in methanol and stored in freezer.

Example 23

FIG. 16B is a schematic diagram illustrating a chemical reaction for coupling a lamotrigine analog (6) with a fluorescent label, such as FAM. In a round bottom flask wrapped with aluminum foil, a reaction solution of 10 mg FAM (Carboxyfluorescein succinimidyl ester), 0.1 mL N,N-diisopropylethylamine and 12 mg of lamotrigine analog (6) is prepared. The reaction solution is stirred for 18 hours, and the volatiles are evaporated under reduced pressure. The residue is re-dissolved in methanol and purified from preparative TLC plates using solvent ethyl acetate/methanol. The tracer (28) is dissolved in methanol and stored in freezer.

Example 24

Figure 17:
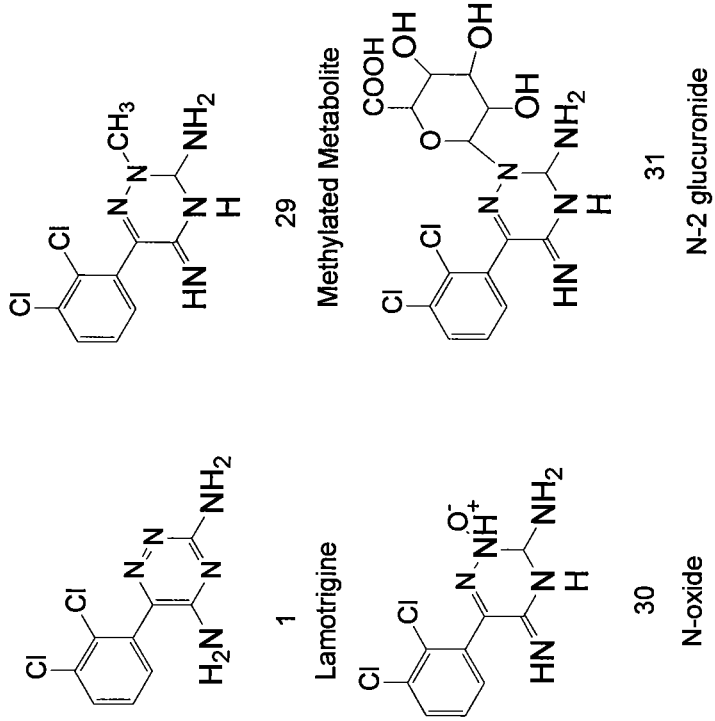
FIG. 17 are schematic diagrams of lamotrigine and embodiments of lamotrigine metabolites.

A polyclonal antisera is obtained and an assay is performed in order to determine the amount of cross-reactivity of the polyclonal antibody with lamotrigine and lamotrigine metabolites. A known amount of lamotrigine is used to react with an anti-lamotrigine antibody prepared in accordance with the present invention. The known concentration of lamotrigine is used to calculate the amount of cross-reactivity between the antibody preparation and the metabolites as follows: N-methyl (29); N-oxide (30); and N-2 gluronide (31). The chemical structures of lamotrigine (1) N-methyl (29); N-oxide (30); and N-2 gluronide (31) are shown in FIG. 17. The percent of cross-reactivity equals 100 times the observed concentration of lamotrigine in μg/mL, which is then divided by the concentration of added metabolites in μg/mL. No cross-reactivity is observed in specimens containing those metabolites. High concentrations of these compounds are spiked into human serum and tested as samples. The metabolites are assayed and compared to control serum (no lamot rigine). Cross reactivity is calculated using the following equation:

$$\% \text{ cross reactivity} = \frac{\text{Recovered Concentration}}{\text{Concentration of cross reactant}} \times 100\%$$

The results indicate that at a concentration of 500 µg/mL, N-2 methyl and N-2 glucuronide do not have any cross-reactivity. Also, the cross-reactivity of N-2 oxide at 500 µg/mL is less then 3%.

Example 25

A polyclonal antibody that binds with lamotrigine is prepared using a lamotrigine analog having an immunogenic conjugate. More particularly, the lamotrigine immunogen (20) having the KLH immunogenic moiety was used to generate the anti-lamotrigine polyclonal antibody, which is well known in the art. An immunogenic composition is prepared by mixing about 0.5 mL of an immunogen (20) containing composition with about 0.5 mL of Freund's adjuvant. The resulting 1 mL immunogenic cocktail is then injected in each rabbit. Subsequent immunogenic injections having the same cocktail are administered to the rabbits every four weeks in order to cause the rabbit to produce anti-lamotrigine polyclonal antibody. Sera from two rabbits, Rabbit number 1309 and 1310, are screened via ELISA using antigens, as described below.

Example 26

ELISA plates for use in an ELISA assay were prepared in order to study the polyclonal antibody prepared as described in Example 25. As such, various lamotrigine antigens (21), (23), and (24) were coated on different ELISA plates before being subjected to the anti-lamotrigine polyclonal antibody and competing free lamotrigine. More particularly, the lamotrigine antigens were diluted in coating buffer, and then added to the wells of ELISA plate. After the ELISA plate was incubated for 60 min at 37° C., the solvent in the coating buffer was decanted and a blocking buffer was added to the plate. The plate was incubated again for 60 min at 37° C., and the solvent in the blocking buffer was decanted from the plate. The ELISA plate was then stored with the blocking agent in the wells at 2-8° C. for up to 1 week.

Example 27

The antibody titer for a polyclonal antibody prepared in accordance with Example 25 was determined using ELISA plates as prepared in Example 26. As such, a serial dilution was performed to produce the same 100 µL volume in each well. The antibody dilutions were prepared between 1:10 and 1:2000 in PBS at pH 7.4 and containing 0.1% BSA. The samples were diluted 10 fold, and the dilutions were started at 1:100 and serially diluted 10 fold across the plate. Subsequently, a 100 µL of antibody sample was added to each well on the ELISA plate. The plate was then incubated for 60 min at 37° C., and washed three times with 250 µL of PBS at pH 7.4 with 0.05% tween. Next, 125 µL of a diluted second antibody conjugate (in PBS, pH 7.4), which is different from the antigen previous coated onto the plate, was added to each well of the plate. Titer was determined experimentally by incubating the plate for 60 min at 37° C., which was then washed three times with 250 µL of PBS at pH 7.4 with 0.05% tween. After washing, about 125 µL of 2,2'-azino-bis(3-ethylbenzthiazoline-6-sulfonic acid ("ABTS") substrate was added to each well in the plates, and the plate was incubated again for 20 min. The plate was read at 405 nm, and the titer results are provided in Table 1.

TABLE 1

| | | ELISA Titer | | |
|---|---|---|---|---|
| Rabbit No. | Immunogen | Antigen 24 | Antigen 23 | Antigen 21 |
| 1309 | 20 | 1:12000 | 1:19000 | 1:11000 |
| 1310 | 20 | 1:210 | 1:1200 | 1:900 |

These results indicate that the titer was not sufficient for the microparticle agglutination immunoassay. This is because the microparticles agglutination immunoassay should be conducted with a titer of at least 1:100,000. As such, the immunogen (20) did not produce sufficient antibodies for use in commercial immunodiagnostic assay protocols.

Example 28

The avidity of the anti-lamotrigine antibodies prepared with immunogen (20) for lamotrigine analogs were determined by a binding inhibition study. As such, samples were prepared in 1 mL of PBS at pH 7.4 with 0.1% BSA. A composition having 30% Bmax titer or 50% Bmax titer was used to divide the obtained titer value into approximately half the titer value. Accordingly, this can accommodate a 1:1 dilution which occurs when the anti-lamotrigine antibody is mixed with the inhibiting protein. Using 30% Bmax, an antibody titer of 1:12000 is diluted to 1:6000 during the sample preparation stage. About 50 µL of lamotrigine at different concentrations or calibrator values, (0, 2.5, 5, 10, 20, 40 µg/ml) were then applied to the plate as prepared in accordance with Example 25. About 50 µL of the diluted antibody was dispensed into the plate, and compositions in the plate were mixed for 1 min on a horizontal plate shaker. The plate was characterized by a first row not containing lamotrigine or anti-lamotrigine antibody, and the first row was used as the negative control. A second row not containing lamotrigine was used as the positive control. The plate was incubated for 60 min, and washed three times with 250 µL of PBS at pH 7.4 with 0.05% tween. About 125 µL of a diluted second antibody conjugate, which is different from immunogen 15, such as antigens (21), (23), or (24), in PBS at pH 7.4 was added to each well of the plate. Titer was determined experimentally by the plate being incubated for 60 min at 37° C. and washed 3 times with 250 µL PBS, pH 7.4 with 0.05% tween. Subsequently, about 125 µL of ABTS substrate was added to each well of the plates and the plate was incubated for 20 min. The plate was read at 405 nm, and the results are provided in Tables 2 and 3.

TABLE 2

| Rabbit No. 1309 | Antigen 24 | | Antigen 23 | | Antigen 21 | |
|---|---|---|---|---|---|---|
| Lamotrigine (µg/ml) | $A_{405}$ | B/Bo | $A_{405}$ | B/Bo | $A_{405}$ | B/Bo |
| 0 | 0.8 | 1.00 | 0.4 | 1.00 | 0.55 | 1.00 |
| 2.5 | 0.78 | 0.98 | 0.35 | 0.88 | 0.46 | 0.84 |
| 5 | 0.75 | 0.94 | 0.33 | 0.83 | 0.40 | 0.73 |
| 10 | 0.72 | 0.90 | 0.35 | 0.88 | 0.42 | 0.76 |
| 20 | 0.65 | 0.81 | 0.33 | 0.83 | 0.40 | 0.73 |
| 40 | 0.6 | 0.75 | 0.36 | 0.9 | 0.38 | 0.69 |

TABLE 3

| Rabbit No. 1310 | Antigen (24) | | Antigen (23) | | Antigen (21) | |
|---|---|---|---|---|---|---|
| Lamotrigine (µg/ml) | $A_{405}$ | B/Bo | $A_{405}$ | B/Bo | $A_{405}$ | B/Bo |
| 0 | 1.35 | 1.00 | 0.60 | 1.00 | 0.7 | 1.00 |
| 2.5 | 1.30 | 0.96 | 0.20 | 0.33 | 0.3 | 0.43 |
| 5 | 1.20 | 0.89 | 0.21 | 0.35 | 0.3 | 0.43 |
| 10 | 1.15 | 0.85 | 0.25 | 0.42 | 0.3 | 0.43 |
| 20 | 1.00 | 0.74 | 0.23 | 0.38 | 0.28 | 0.4 |
| 40 | 0.99 | 0.73 | 0.23 | 0.38 | 0.27 | 0.39 |

B is the absorbance value at 405 nm for the test sample, and Bo is the absorbance value at 405 nm in the absence of a competing analyte (A405 @ zero calibrator), wherein Bo is B at zero calibrator, or no analyte. B/Bo indicates inhibition upon addition of competing analyte (e.g., ELISA format). The absorbance (B) is dependant on immunoreactions and reaction conditions (buffer, reaction times, parameters, etc). Higher absorbance can be attributed by strong immunoreactions when an antigen binds strongly to an antibody strongly, which can be by adding more reagents, by changing of assay parameter, or by changing reaction time, or by changing reaction temperature.

A known amount of analyte, which is a calibrator having a known concentration of 0-40 µg/ml competes with lamotrigine analog on the ELISA plate for anti-lamotrigine antibody. The absorbance (B) at a given analyte concentrate can be lower than the absorbance free of analyte when the B/Bo is less than or equal to 1. If free drug or analyte binds strongly with the antibody, it can freely compete with antigen for the available antibody. Absorbance B can then drop quickly as the available antibody binds only with free drug, which also results in B/Bo decrease quickly. If the binding between free drug and antibody is week, the free drug does not displace the antigen from the antibody, and the absorbance B may slightly drop. The B/Bo decreases from 1.00 over the span of calibrator range, wherein the changes in B/Bo over the span of calibrator range are dependant of immunoreactions between the antigen, free drug, and antibody. The difference in an immunoreaction (e.g., competition or B/Bo) at various concentrations is essential in competitive immunoassays. The larger difference in B/Bo over the span of assay range at each calibrator concentration can result in a more accurate measurement. Over the span of assay calibration range, B/Bo is dependant on antigen and antibody interactions. High absorbance (e.g., OD between 0.5 to 1.5) and large differences in B/Bo at each level of known analyte concentration (calibrator) are important in reliable and reproducible immunoassay. A large dynamic range of B/Bo (e.g., large difference of B/Bo over incremental changes in analyte concentration) over the assay range and a strong absorbance (B) is required to obtain the accuracy and precision for a commercial immunoassay.

In tables 2 and 3 (e.g., Rabbit 1309), the antigen (24) provides highest absorbance (B or Bo), and B/Bo decreases over the span of calibrator range. The Antigen (24) has a similar structure as the immunogen (20), where only carrier protein is different. Due to the similarity in structure, the epitope on the antigen is the same as the epitope stimulated antibody response, and the antibody can recognize the linker as well as drug. Thus, highest absorbance is expected because it takes more free drugs to compete with antigen for antibody, and leads to small decrease in B/Bo over the span of assay range.

Antigen (23) has a different structure than immunogen (e.g., different linker, different site of derivatization, and different carrier protein), which results in the absorbance (B) being the lowest. Antigen (21) has a different structure than immunogen (e.g., different linker, same site of derivatization, and different carrier protein). The absorbance (B) falls in the middle, which is different from the immunogen, and the differences in B/Bo over span of assay range are the largest. However, the antigens (24), (23), (21) are not optimal against the antibody due to poor titer and poor B/Bo profile.

Example 29

A polyclonal antibody that binds with lamotrigine was prepared using a protocol similar as described in Example 25. More particularly, the lamotrigine immunogen (18) having the KLH immunogenic moiety was used to generate the anti-lamotrigine polyclonal antibody.

Example 30

ELISA plates for use in an ELISA assay were prepared substantially in accordance with Example 26 in order to study the polyclonal antibody prepared as described in Example 27. More particularly, the antigens (24), (23), (21), (25), and (26) were coated onto ELISA plates.

Example 31

The antibody titer for a polyclonal antibody prepared in accordance with Example 29 was determined using ELISA plates as prepared as in Example 30. The protocol for determining the antibody titer was followed as described in Example 27. Accordingly, the plate was read at 405 nm, and the titer results are provided in Table 4.

TABLE 4

| Rabbit No. | Immunogen | ELISA titer | | | | |
|---|---|---|---|---|---|---|
| | | Antigen 24 | Antigen 23 | Antigen 21 | Antigen 25 | Antigen 26 |
| 2689 | 18 | 1:240 | 1:160000 | 1:800 | 1:400 | 1:400 |
| 2690 | 18 | 1:100 | 1:45000 | 1:200 | 1:400 | 1:300 |

These results indicate that the titer was not sufficient for the microparticle agglutination immunoassay because the microparticles agglutination immunoassay should be conducted with a titer of at least 1:100,000. However, the titer with respect to antigen (23) was significantly higher in comparison with the antibodies generated with immunogen (20). In part, the high titer with respect to antigen (23) can be attributed to the similarity of the chemical constructs of antigen (23) in comparison with immunogen (18), which are only different by the KLH conjugate being substituted with BSA. As such, it is possible the anti-lamotrigine antibody generated with the immunogen (18) may be suitable for use in commercial immunodiagnostic assay protocols with antigen (23) as the competitor.

Example 32

The avidity of the anti-lamotrigine antibodies prepared with immunogen (18) for lamotrigine analogs were determined by a binding inhibition study performed with a protocol substantially similar as described in Example 28. More particularly, the antigens (23) and (21) were used. The plate was read at 405 nm, and the results are provided in Tables 5 and 6.

TABLE 5

| Rabbit No. 2689 | Antigen 23 | | Antigen 21 | |
|---|---|---|---|---|
| Lamotrigine (μg/ml) | $A_{405}$ | B/Bo | $A_{405}$ | B/Bo |
| 0 | 0.50 | 1.00 | 0.80 | 1.00 |
| 2.5 | 0.30 | 0.60 | 0.45 | 0.56 |
| 5 | 0.01 | 0.02 | 0.35 | 0.44 |
| 10 | 0.01 | 0.02 | 0.30 | 0.38 |
| 20 | 0.01 | 0.02 | 0.20 | 0.25 |
| 40 | 0.01 | 0.02 | 0.15 | 0.19 |

TABLE 6

| Rabbit No. 2690 | Antigen 23 | | Antigen 21 | |
|---|---|---|---|---|
| Lamotrigine (μg/ml) | $A_{405}$ | B/Bo | $A_{405}$ | B/Bo |
| 0 | 0.75 | 1.00 | 0.5 | 1.00 |
| 2.5 | 0.05 | 0.07 | 0.25 | 0.50 |
| 5 | 0.05 | 0.06 | 0.28 | 0.56 |
| 10 | 0.02 | 0.03 | 0.2 | 0.40 |
| 20 | 0.02 | 0.03 | 0.18 | 0.36 |
| 40 | 0.01 | 0.01 | 0.16 | 0.32 |

The immunogen (20) has a short linker, and is not as immunogenic as immunogen (19). The antibody produced from immunogen (20) shows titer as low as 1:210 and as high as 1:11000, and has a change in B/Bo over the span of assay range being too small or too large. The immunogen (18) has a short linker, and is not as immunogenic as immunogen (19). The antibody produced from immunogen (18) shows good titer (e.g., Rabbit 2690 titer 1:45,000; Rabbit 2689 titer 1:160,000) against antigen (23), but low titer against all other antigens.

Antigen (23) has the similar structure as the immunogen (18) (e.g., only carrier protein is different). Due to the similarity in structure, the epitope on the antigen is the substantially the same as the epitope stimulated antibody response. As such, the antibody can recognize the linker as well as the drug, and the highest absorbance is observed. The improvement of titer in the antibody from rabbits 2689 and 2690, which was up to 1:160,000 and 1:45,000, respectively, may be caused by the increased recognition of the antigen by the antibody.

The incremental changes in B/Bo over the span of assay range shows promising B/Bo profile. Antigen (21) is a good competitor against lamotrigine for the antibody when only B/Bo is considered. The antibody shows a low titer (poor recognition) against antigen (21), which may be because this antigen has a different structure than immunogen (18) (e.g., different linker, same site of derivatization, and different carrier protein).

Example 33

A polyclonal antibody that binds with lamotrigine was prepared using a protocol similar as described in Example 25. More particularly, the lamotrigine immunogen (19) having the KLH immunogenic moiety was used to generate the anti-lamotrigine polyclonal antibody.

Example 34

ELISA plates for use in an ELISA assay were prepared substantially in accordance with Example 26 in order to study the polyclonal antibody prepared as described in Example 33. More particularly, the antigens (24), (23), (21), (25), and (26) were coated onto ELISA plates.

Example 35

The antibody titer for a polyclonal antibody prepared in accordance with Example 33 was determined using ELISA plates as prepared as in Example 34. The protocol for determining the antibody titer was followed as described in Example 27. Accordingly, the plate was read at 405 nm, and the titer results are provided in Table 7.

TABLE 7

| Rabbit | | ELISA titer | | | | |
|---|---|---|---|---|---|---|
| No. | Immunogen | Antigen 24 | Antigen 23 | Antigen 21 | Antigen 25 | Antigen 26 |
| 2693 | 19 | 1:300000 | 1:310000 | 1:700000 | 1:4400000 | 1:1900000 |
| 2694 | 19 | 1:200000 | 1:1700000 | 1:850000 | 1:4400000 | 1:1800000 |

The anti-lamotrigine polyclonal antibodies prepared with immunogen 19, which includes a long linker between the lamotrigine scaffold and the immunogenic moiety, exhibit high titers that are suitable for microparticle agglutination immunoassays. As such, long linkers can be beneficial for imparting efficacious immunogenicity to an immunogen based on the lamotrigine drug. As such, the linker of immunogen 19, or those having similar length or other property, can be conjugated at the 4-position and the 3-position of lamotrigine analogs.

Example 36

The avidity of the anti-lamotrigine antibodies prepared with immunogen (19) for lamotrigine analogs were determined by a binding inhibition study performed with a protocol substantially similar as described in Example 26. More particularly, the antigens (24), (23), (21), (25), and (26) were used. The plate was read at 405 nm, and the results are provided in Tables 8 and 9.

TABLE 8

| Rabbit No. 2693 | Antigen 24 | | Antigen 23 | | Antigen 21 | | Antigen 25 | | Antigen 26 | |
|---|---|---|---|---|---|---|---|---|---|---|
| Lam. (μg/ml) | $A_{405}$ | B/Bo | $A_{405}$ | B/Bo | $A_{405}$ | B/Bo | $A_{405}$ | B/Bo | $A_{405}$ | B/Bo |
| 0 | 0.28 | 1.00 | 0.68 | 1.00 | 1.55 | 1.00 | 0.32 | 1.00 | 1.1 | 1.00 |
| 2.5 | 0.08 | 0.29 | 0.08 | 0.12 | 1.52 | 0.98 | 0.16 | 0.50 | 0.4 | 0.36 |
| 5 | 0.05 | 0.18 | 0.08 | 0.12 | 1.45 | 0.94 | 0.15 | 0.47 | 0.28 | 0.25 |
| 10 | 0.04 | 0.14 | 0.08 | 0.12 | 1.40 | 0.90 | 0.08 | 0.04 | 0.24 | 0.22 |
| 20 | 0.03 | 0.11 | 0.08 | 0.12 | 1.28 | 0.83 | 0.07 | 0.22 | 0.20 | 0.18 |
| 40 | 0.02 | 0.07 | 0.08 | 0.12 | 1.20 | 0.77 | 0.07 | 0.22 | 0.16 | 0.15 |

TABLE 9

| Rabbit No. 2693 | Antigen 24 | | Antigen 23 | | Antigen 21 | | Antigen 25 | | Antigen 26 | |
|---|---|---|---|---|---|---|---|---|---|---|
| Lam. (μg/ml) | $A_{405}$ | B/Bo | $A_{405}$ | B/Bo | $A_{405}$ | B/Bo | $A_{405}$ | B/Bo | $A_{405}$ | B/Bo |
| 0 | 0.83 | 1.00 | 0.44 | 1.00 | 1 | 1.00 | 0.72 | 1.00 | 1.80 | 1.00 |
| 2.5 | 0.28 | 0.34 | 0.08 | 0.18 | 0.90 | 0.90 | 0.36 | 0.50 | 1.16 | 0.64 |
| 5 | 0.22 | 0.27 | 0.08 | 0.18 | 0.85 | 0.85 | 0.32 | 0.44 | 1.04 | 0.58 |
| 10 | 0.15 | 0.18 | 0.08 | 0.18 | 0.80 | 0.80 | 0.28 | 0.39 | 0.88 | 0.49 |
| 20 | 0.12 | 0.14 | 0.08 | 0.18 | 0.78 | 0.78 | 0.20 | 0.28 | 0.80 | 0.44 |
| 40 | 0.10 | 0.12 | 0.08 | 0.18 | 0.70 | 0.70 | 0.18 | 0.25 | 0.68 | 0.38 |

Immunogen (19) has a long linker and the epitope is more accessbile for antibody interaction, and was the most immunogenic with the antibody having the highest titer of up to 1:4,400,000. All antigens (e.g., 21, 23, 24, 25, 26) show fair to good competition with lamotrigine free drug for the polyclonal antibody produced from immunogen (19).

Antigen (24) has a short linker and the site of derivatization is the same as immunogen (19). The weaker recognition of antibody by antigen (24) leads to relatively less titer of up to 1:300,000. The binding of antigen (24) and antibody is comparatively weaker due to less available surface area for antibody interaction. The B/Bo shows sharp decrease even at very small concentrations of lamotrigine, where incremental changes in B/Bo at higher lamotrigine concentrations shows the feasibility of antigen (24).

Antigen (23) has a short linker and the site of derivatization is different from immunogen (19). The comparatively weaker recognition of antibody by antigen (23) leads to relatively lower titer of up to 1:700,000. The binding of antigen (23) and antibody is very weaker due to less available surface area and less recognition for antibody interaction. The B/Bo shows sharp decrease even at very small concentration of lamotrigine, which indicates a preference for lamotrigine instead of the lamotrigine analog.

Antigen (21) has a similar structure as the immunogen (19), except having a different carrier protein. The antibody shows moderate titer against antigen (21).

Antigen (25) has a shorter but similar linker than immunogen (19). In fact, the analog (6) used in the preparation of antigen (25) is the precursor of analog (8), which is used in the preparation of immunogen (19). Strong recognition resulted from the similarity in structure leads to very high titer of up to 1:4,400,000. Antigen (25) freely competes against free drug for antibody due to the difference in structure, and shown incremental changes in B/Bo. Antigen (25) and the polyclonal antibody could be used in commercial immunoassay because of the high titer and good B/Bo profile.

Antigen (26) has a very long linker, which is second longest next to antigen (21). The increased immureaction between antigen (25) and antibody leads to high titer of up to 1,900,000. Antigen (26) freely competes against free drug for antibody due to the difference in structure, and shown incremental changes in B/Bo. Antigen (26) and the polyclonal antibody are currently used in commercial immunoassay because of high titer and good B/Bo profile. Thus, the anti-lamotrigine polyclonal antibodies prepared with immunogen 19 were shown to have favorable avidity, and showed competitive binding profiles suitable for immunodiagnostic assays.

Example 37

The antibody titer for a polyclonal antibody prepared in accordance with Example 33 was determined using ELISA plates as prepared similarly as in Example 34; however, anti-rabbit IgG and anti-rabbit IgM were coated onto the ELISA plate. The protocol for determining the antibody titer was followed as described in Example 27, except antigen 21 was used. Accordingly, the plate was read at 405 nm, and the titer results are provided in Table 10.

TABLE 10

| Subclass IgG/IgM ELISA test | Titer, against antigen 20 | |
|---|---|---|
| Rabbit No. | Anti-rabbit IgG | Anti-rabbit IgM |
| 2693 | 1:1700000 | 1:70 |
| 2694 | 1:3500000 | 1:100 |

The titer shows that both anti-rabbit IgG and anti-rabbit IgM were activated against the antigen. The polyclonal antisera are mostly IgG antibodiess due to the fact that the antibodies show much higher titer against anti-rabbit IgG.

Example 38

Anti-lamotrigine antibodies that bind with lamotrigine and analogs were prepared for use in immunodiagnostic assays. The monoclonal antibodies were prepared in nine female Balb/C mice that were 16 weeks of age or older, which were immunized by multiple injections of immunogen (19). The immunogenic injection solution for each mouse included 250 μL of an immunogenic solution comprising immunogen (19), which was mixed with 250 μL of complete Freund's adjuvant. The immunogenic injection solution was loaded into an appropriately sized syringe fitted with a 37 gauge hypodermic needle and injected into each mouse. The booster injections were repeated after 14 days, but using incomplete Freund's adjuvant. The booster injections were repeated again on day 60 and day 80. Additionally, on day 45 the mice were tested for anti-lamotrigine antibody by acquiring blood via a tail bleed, wherein the antibodies were tested by ELISA to determine titer and avidity.

Example 39

ELISA plates for use in an ELISA assay were prepared substantially in accordance with Example 26 in order to study the antibody prepared as described in Example 38. More particularly, the antigen (21) was coated onto ELISA plates. Briefly, antigen (21) was diluted in a coating buffer and was added to the wells of the ELISA plate. After being incubated for 60 min at 37° C., the buffer solvent was decanted and a blocking buffer was added to the plates. The plate was again incubated for 60 min at 37° C. and the blocking solvent was decanted from the plate. The plate was then stored with the blocking agent in the wells at 2-8° C. for up to 1 week.

Example 40

The anti-lamotrigine antibody titer was determined using the blood obtained from the tail bleed described in Example 36. The titer determination protocol was initiated by the bleeds being serially diluted from 1:100 to 1:10,000,000 by using a 10-fold dilution. The dilutions are prepared in microcentrifuge tubes containing PBS at pH 7.4. About 100 μL of sample obtained from the blood was added to each well on the ELISA plate. The plate was then incubated for 60 min at 37° C. and washed three times with 250 μL of PBS at pH 7.4 with 0.05% tween. About 125 μL of a diluted second antibody conjugate in PBS at pH 7.4 was added to each well of the plate. About 125 μL of ABTS substrate was added to each well of the plates and the plate was incubated for 20 min before being read at 405 nm, where the results are shown in Table 11.

TABLE 11

| Dilution | Mouse # (ELISA titer, against antigen 21) | | | | | | | | |
|---|---|---|---|---|---|---|---|---|---|
| | 1 | 2 | 3 | 4 | 5 | 7 | 8 | 9 | 10 |
| 1:100 | 3.44 | 3.50 | 3.516 | 3.539 | 3.541 | 3.5845 | 3.3305 | 3.401 | 3.4495 |
| 1:1000 | 3.31 | 3.28 | 3.448 | 3.4095 | 3.455 | 3.5885 | 3.4135 | 3.211 | 3.183 |
| 1:10000 | 3.18 | 3.20 | 3.2285 | 3.2135 | 3.0945 | 3.2785 | 3.0835 | 2.907 | 2.9205 |
| 1:100000 | 2.21 | 1.24 | 2.873 | 2.585 | 2.5615 | 2.804 | 2.7455 | 2.1635 | 2.1495 |
| 1:1000000 | 0.62 | 0.22 | 1.178 | 0.7735 | 0.848 | 0.9655 | 1.0545 | 0.508 | 0.518 |
| 1:10000000 | 0.25 | 0.10 | 0.2475 | 0.1875 | 0.167 | 0.2315 | 0.21 | 0.1465 | 0.1255 |

The titer is calculated by an end point titer having about 10% of the maximum OD. In Table 11, the average maximum OD is 3.5., and the antibody titer is 10% of maximum O.D. of 0.35. Mouse 3 has the highest titer because at 1:1,000,000 dilution and at 1:10000000 dilution, it has the highest absorbance (OD)

Example 41

The avidity of the anti-lamotrigine antibodies prepared with immunogen (19) in accordance with the protocol described in Example 38 for generating monoclonal antibodies was determined by a bind inhibition study performed with a protocol substantially similar as described in Example 28. More particularly, the antigen (21) was used. The plate was read at 405 nm, and the results are provided in Tables 12 and 13.

TABLE 12

| Lamotrigine concentration | Absorbance (ELISA Avidity) Mouse # | | | | | | | | |
|---|---|---|---|---|---|---|---|---|---|
| (μg/ml) | 1 | 2 | 3 | 4 | 5 | 7 | 8 | 9 | 10 |
| 0 | 0.6995 | 0.9205 | 0.7555 | 0.8865 | 0.816 | 0.4645 | 0.6215 | 0.5515 | 0.5105 |
| 280 | 0.6965 | 0.8135 | 0.693 | 0.781 | 0.7055 | 0.356 | 0.4305 | 0.347 | 0.4475 |

TABLE 13

| | Mouse # | | | | | | | | |
|---|---|---|---|---|---|---|---|---|---|
| | 1 | 2 | 3 | 4 | 5 | 7 | 8 | 9 | 10 |
| % inhibition | 0.43 | 11.62 | 8.27 | 11.9 | 13.54 | 23.36 | 30.73 | 37.08 | 12.34 |
| B/Bo × 100 | 99.57 | 88.38 | 91.73 | 88.1 | 86.46 | 76.64 | 69.27 | 62.92 | 87.66 |

Fusion candidate was chosen based on the titer (e.g., the amount of the antibody in the blood) and avidity (e.g., specificity against lamotrigine) of the polyclonal antisera. B/Bo indicates inhibition upon addition of a competing analyate, where B/Bo=100–% inhibition. Table 13 shows that polyclonal antibody from mouse No. 1, No. 2, No. 3, No. 4, and No. 10 show preference for the lamotrigine analog (ELISA). Polyclonal antibody from mouse No. 8 and No. 9 show a large difference in B/Bo (or % inhibition) over the span of assay (0-200 μg/ml).

Example 40

A fusion candidate was prepared in order to generate monoclonal antibodies that can bind with lamotrigine and analogs. The fusion candidate was chosen based on avidity and/or the titer or amount of the antibody in the blood. If sensitivity (e.g., to detect low concentration of analyate) or specificity (e.g., to differentiate between analyate and cross reactant) are the desired quality of monoclonal antibody, mouse No. 9 and mouse No. 8 are the prime candidates.

Highest titer values indicate the highest amount of antibody in the blood, and the success rate is the highest when the antibody concentrate in spleen is highest. Thus, Mouse No. 1 is the candidate for the likely fusion success The procedure for producing the fusion candidate was conducted by the immunized mouse being given a final booster injection three to five days before the fusion. This booster injection was administered 4 weeks after the previous injection, where this interval can allow most of the circulating antibodies to be cleared from the blood stream by the mouse. The final booster injection is used for two purposes: (1) to induce a good, strong response; and (2) to synchronize the maturation of the response. This can allow an increase in the relative concentration of the appropriate B-lymphocyte fusion partners. The final boost was direct at the spleen since it is the best choice for lymphocyte isolation. The spleen of the mouse was removed using aseptic technique and placed in 10 mL of complete culture medium in a sterile petri dish, and was then ground between two sterile frosted microscope slides. The resulting single-cell suspension was drawn off and counted using a hemocytometer. Myeloma cells were mixed into the spleen cells in a ratio of 1:5 and centrifuged for 15 min at about 800×G. The supernatant liquid was drawn off and discarded, and 15 mL of serum-free IMDM culture media was added. The cells were re-suspended and again centrifuged. The resulting cell pellet was fused using polyethylene glycol/DMSO.

After fusion, the cells were diluted in Iscove's Dulbecco's medium supplemented with 10% fetal bovine serum (Hyclone Labs), 10%> condimed HI, 50 mM 2-mercaptoethanol, 20 mM ethanolamine, hypoxanthine-methotrexate-thymidine, 4 mM glutamine, and pen/strep antibiotics. This mixture of fused cells was plated at 200 μL/well into sterile 96-well microculture plates. The covered plates were placed in an incubator for 6 days at 37 degree C. in 5% $CO_2$.

Example 43

The avidity of the anti-lamotrigine antibodies prepared with immunogen (19) in accordance with the protocol described in Example 42 for generating monoclonal antibodies was determined by a binding inhibition study performed with a protocol substantially similar as described in Example 26. More particularly, antigen (21) was used. The plate was read at 405 nm, and the results are provided in Tables 14 and 15.

TABLE 14

| Lamotrigine | Absorbance (ELISA) Clones (after Fusion) | | | | | | |
|---|---|---|---|---|---|---|---|
| concentration (μg/mL) | 1D11 | 3E8 | 4G6 | 5G11 | 8B10 | 4B11 | 7E10 |
| 0 | 1 | 0.1485 | 1.7225 | 1.333 | 1.2675 | 1.07 | 1.2665 |
| 280 | 0.9475 | 0.126 | 0.201 | 0.853 | 0.755 | 0.636 | 0.823 |

TABLE 15

| | Clones (after fusion screening) | | | | | | |
|---|---|---|---|---|---|---|---|
| | 1D11 | 3E8 | 4G6 | 5G11 | 8B10 | 4B11 | 7E10 |
| % inhibition | 5.25 | 15.15 | 88.33 | 36.01 | 40.43 | 40.56 | 35.02 |
| B/Bo × 100 | 94.75 | 84.85 | 11.67 | 63.99 | 59.57 | 59.44 | 64.98 |

The Inhibition profile from Table 15 shows the fused clone 4G6 prefers free drug (e.g., large % inhibition or smallest B/Bo) and the fused clone 3E8 prefers the lamotrigine analog (21).

Example 44

After fusion, as described in Example 43, 1× clones were prepared. Accordingly, after a positive tissue culture supernatant has been identified, the next step is to clone the antibody-producing cell. The original positive well often contains more than one clone of hybridoma cells, and many hybrid cells have an unstable assortment of chromosomes. Single-cell cloning ensures that cells that produce the antibody of interest are truly monoclonal and are stable. The hybridoma cells were cloned by limiting dilutions. A growth medium was added to a well containing fused cells. The clones grew rapidly and the 1× clones were ready for screening (ELISA and QMS) after two weeks. The avidity of the anti-lamotrigine antibodies was determined by a binding inhibition study performed with a protocol substantially similar as described in Example 28. More particularly, antigen (21) was used. The plate was read at 405 nm, and the results are provided in Tables 16 through 21.

TABLE 16

| Lamotrigine | Absorbance (ELISA) 1X Clones | | | | | | |
|---|---|---|---|---|---|---|---|
| concentration (μg/mL) | 1D11-1 | 1D11-10 | 1D11-30 | 3E8-7 | 3E8-14 | 3E8-25 | 4G6-5 |
| 0 | 2.123 | 2.33 | 2.05 | 2.13 | 2.21 | 2.27 | 1.87 |
| 200 | 0.475 | 1.12 | 0.38 | 0.67 | 0.455 | 0.814 | 0.39 |

TABLE 17

| | 1X Clones | | | | | | |
|---|---|---|---|---|---|---|---|
| | 1D11-1 | 1D11-10 | 1D11-30 | 3E8-7 | 3E8-14 | 3E8-25 | 4G6-5 |
| % inhibition | 77.6 | 51.9 | 81.5 | 68.4 | 79.4 | 64.2 | 78.7 |

TABLE 18

| Lamotrigine concentration (μg/mL) | Absorbance (ELISA) 1X Clones | | | | | | |
|---|---|---|---|---|---|---|---|
| | 4G6-21 | 4G6-28 | 5G11-7 | 5G11-18 | 5G11-34 | 8B10-9 | 8B10-14 |
| 0 | 2.05 | 2.08 | 2.24 | 2.15 | 2.38 | 1.98 | 1.68 |
| 200 | 0.34 | 0.31 | 1.17 | 0.7015 | 1.39 | 0.22 | 0.42 |

TABLE 19

| % inhibition | 4G6-21 | 4G6-28 | 5G11-7 | 5G11-18 | 5G11-34 | 8B10-9 | 8B10-14 |
|---|---|---|---|---|---|---|---|
| 0 | 83.1 | 85 | 47 | 67 | 42 | 89 | 75 |

TABLE 20

| Lamotrigine concentration (µg/mL) | Absorbance (ELISA) 1X Clones | | | | | | |
|---|---|---|---|---|---|---|---|
| | 8B10-23 | 4B11-3 | 4B11-11 | 4B11-17 | 7E10-8 | 7E10-26 | 7E10-37 |
| 0 | 2.03 | 1.89 | 1.92 | 2.61 | 2.25 | 2.36 | 2.45 |
| 200 | 1.02 | 0.24 | 0.24 | 0.56 | 0.96 | 0.85 | 0.60 |

TABLE 21

| % inhibition | 1X Clones | | | | | | |
|---|---|---|---|---|---|---|---|
| | 8B10-23 | 4B11-3 | 4B11-11 | 4B11-17 | 7E10-8 | 7E10-26 | 7E10-37 |
| 0 | 49.5 | 87.1 | 87.7 | 78.4 | 57.2 | 64 | 75.4 |

The larger percent inhibition indicates that the clone prefers the free lamotrigine over the lamotrigine analog (21).

A QMS® assays was performed to test the 1× clones prepared as in Example 44. The screening on QMS® is not optimized (assay parameter and titer of the 1× clones). The data is shown on Table 22.

TABLE 22

| Lamotrigine concentration (µg/mL) | Delta Absorbance (Immunoturbidimetric Format) 1X Clones | | |
|---|---|---|---|
| | 4G6-21 | 4G6-28 | 5G11-34 |
| 0 | 1.1254 | 0.7830 | 0.2172 |
| 40 | 0.0024 | 0.0013 | 0.0000 |
| % inhibition | 99.8 | 99.8 | 99.9 |

It can be observed from the Table 22 that the 1× clones recognize the lamotrigine analog (21), and the ability of lamotrigine free drug to inhibit the immunoreaction indicates the binding is specific to lamotrigine as opposed to non-specific binding of protein carrier. Thus, the clones may be used in an immunoassay.

Example 45

The QMS® lamotrigine assay is an automated homogeneous particle-enhanced turbidimetric immunoassay used for the analysis of lamotrigine in serum or plasma. A QMS® assay was performed to test the polyclonal antibodies prepared as in Example 34. The QMS assay for lamotrigine was conducted using a liquid, ready-to-use, two-reagent kit, which contains: R1, which is comprised of sheep polyclonal antibodies that bind with lamotrigine prepared from immunogen (19) at less than <1% in bis-tris buffer with about sodium 0.05% azide; and R2, which is comprised of lamotrigine-coated microparticles with antigen (26) at less than 0.5% with sodium azide at 0.05%. The QMS lamotrigine assay can be calibrated using a full calibration (6-point) procedure to generate a calibration curve similar to FIG. 4, wherein Seradyn QMS lamotrigine calibrators (0.0, 2.5, 5, 10, 20, 40 µg/ml) are used. The results are provided in Table 23.

TABLE 23

| Polyclonal antibody R1 Lamotrigine (µg/mL) sample | Rate (Delta Absorbance) Lamotrigine antigen (22) coated Latex |
|---|---|
| 0 | 179 |
| 2.5 | 107 |
| 5 | 60 |
| 10 | 34 |
| 20 | 18 |
| 40 | 11 |

When a sample containing lamotrigine is added, the agglutination reaction is partially inhibited and observed by slowing down the rate of absorbance change. A s such, a concentration-dependent classic agglutination inhibition curve can be obtained with maximum rate of agglutination at the lowest lamotrigine concentration (e.g., at zero µg/ml) and the lowest agglutination rate at the highest lamotrigine concentration (e.g., 40 µg/ml). The incremental changes in rate over the assay range shown in Table 23 indicate the antibody, antigen (competitor), and the free drug (lamotrigine) interaction is suitable for a commercial immunoassay for use in an automated system.

Example 46

An experiment was performed to compare an automated homogeneous particle-enhanced turbidimetric immunoassay to an HPLC method for detecting lamotrigine. The method comparison assay is an experiment designed to evaluate the bias between two methods that measure the same analyte. A QMS® assay was performed as described in Example 45 to test the polyclonal antibodies prepared as in Example 34. As such, lamotrigine patient samples are assayed and compared to a reference method HPLC. The purpose of the evaluation is to determine if the two methods yield equivalent results within statistical power of the experiment. The comparison experiment was conducted with twenty five patient samples consisting of serum or sodium heparinized plasma. Concentrations in the turbidimetric immunoassay ranged from 1.59 to 35 µg/mL and concentrations on the HPLC ranged from 1.3 to 32.9 µg/mL. Results from the automated QMS® lamotrigine assay were compared with the results from HPLC and shown in Tables 23 and 24.

TABLE 23

| Seradyn ID # | HPLC Result | Seradyn QMS (H717) | | |
|---|---|---|---|---|
| | | Rep 1 | Rep 2 | Mean |
| 0001 | 4.2 | 5.14 | 5.16 | 5.2 |
| 0002 | 1.3 | 1.6 | 1.57 | 1.6 |
| 0003 | 7.7 | 8.37 | 8.29 | 8.3 |
| 0004 | 9.6 | 8.92 | 8.87 | 8.9 |
| 0005 | 1.8 | 1.95 | 1.97 | 2.0 |
| 0006 | 10.3 | 12.63 | 13.33 | 13.0 |
| 0007 | 8.2 | 9.08 | 8.91 | 9.0 |
| 0008 | 9.1 | 10.22 | 10.11 | 10.2 |
| 0009 | 2.4 | 2.66 | 2.75 | 2.7 |
| 0010 | 15.6 | 16.93 | 16.38 | 16.7 |
| 0011 | 5.5 | 6.13 | 5.91 | 6.0 |
| 0012 | 19.8 | 21.56 | 21.45 | 21.5 |
| 0013 | 12.7 | 14.55 | 14.48 | 14.5 |
| 0014 | 12.3 | 13.73 | 13.99 | 13.9 |
| 0015 | 21.2 | 24.13 | 24.36 | 24.2 |
| 0016 | 16.7 | 18.68 | 18.9 | 18.8 |
| 0017 | 3.1 | 3.29 | 3.44 | 3.4 |
| 0018 | 3.6 | 4.33 | 4.27 | 4.3 |
| 0019 | 2.8 | 3.41 | 3.36 | 3.4 |
| 0020 | 6.7 | 7.98 | 7.72 | 7.9 |
| 0021 | 13.7 | 15.31 | 15.55 | 15.4 |
| 0022 | 11.1 | 12.93 | 13.24 | 13.1 |
| 0023 | 18.1 | 18.32 | 18.75 | 18.5 |
| 0024 | 18.8 | 25.35 | 22.45 | 23.9 |
| 0025 | 32.8 | 38.37 | 32.88 | 35.6 |

TABLE 24

| | Method HPLC |
|---|---|
| n | 25 |
| Y-intercept | 0.0151 |
| Slope | 1.107 |
| Correlation Coefficient | 0.994 |

Figure 18:
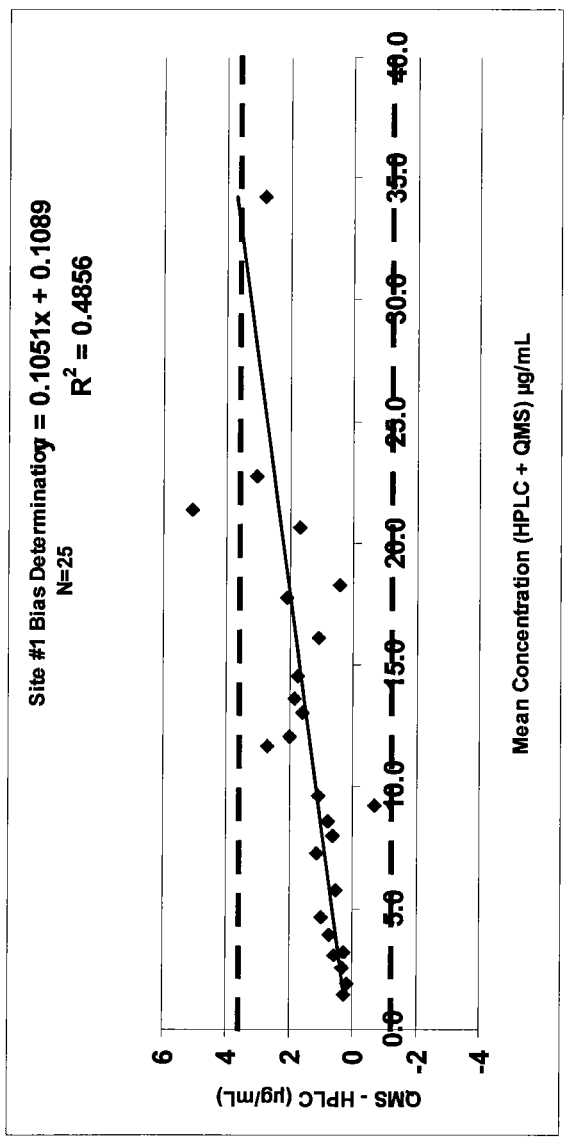
FIG. 18 is a graph of an embodiment of a comparative study between an automated immunoassay and an HPLC method.
Figure 19:
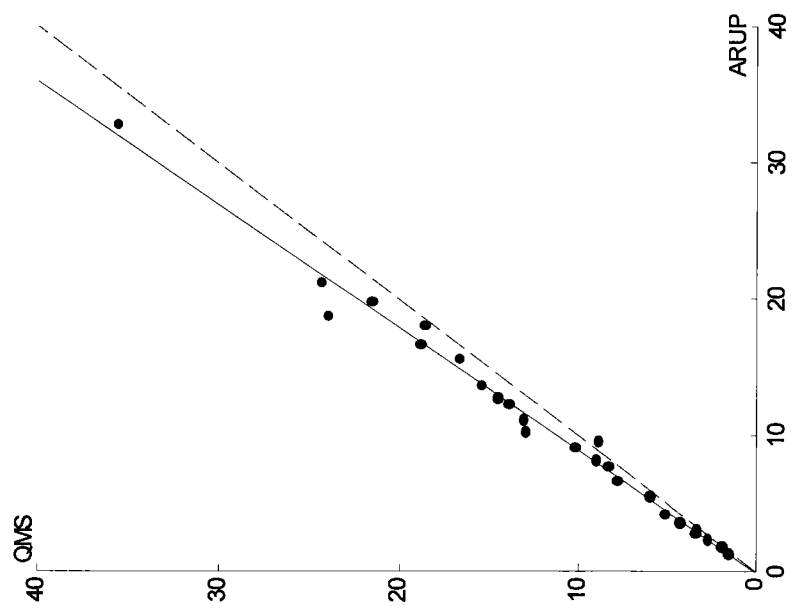
FIG. 19 is a graph of a an embodiment of a comparative study between an automated immunoassay and an HPLC method.

As shown in FIG. 18, the difference between the automated homogeneous particle-enhanced turbidimetric immunoassay and the HPLC method was determined to be less than about 10%. As can be seen in FIG. 19, the concentrations in the turbidimetric immunoassay ranged from 1.59 to 35 μg/mL and concentrations on the HPLC ranged from 1.3 to 32.9 μg/mL. The slope of the QMS® lamotrigine assay on the turbidimetric immunoassay was 1.107 with an intercept of 0.0151, which was compared to the HPLC method prepared by ARUP (Salt Lake City Utah) HPLC/UV. The correlation coefficient (R) was 0.994. Bias plot shows 10% bias between HPLC and QMS values. Thus, the data shows that QMS® assay is a suitable replacement for HPLC reference method.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An antibody composition for use in an immunodiagnostic assay for detecting the presence of lamotrigine in a sample from a patient treated with lamotrigine, the composition comprising:

an anti-lamotrigine antibody produced by an immunogenic composition including a lamotrigine derivative, the lamotrigine derivative having a chemical structure of Formula 1;

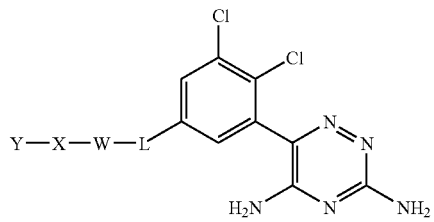

Formula 1 wherein:

L is NH;

W is $CO(CH_2)_2CONH(CH_2)_2$;

X is $NHCO(CH_2)_6$;

Y is $Y_1$—Z, wherein $Y_1$ is CO and Z is BSA or KLH; and wherein the anti-lamotrigine antibody has at least one binding domain capable of binding lamotrigine, and wherein the antibody has a titer at least 1:100,000.

2. The antibody composition as in claim 1, wherein the antibody is a monoclonal antibody.

3. The antibody composition as in claim 1, wherein the antibody is a polyclonal antibody.

4. A polyclonal or monoclonal antibody composition for use in an immunodiagnostic assay for detecting the presence of lamotrigine in a sample, the polyclonal or monoclonal antibody composition comprising:

an anti-lamotrigine antibody produced by an immunogenic composition including a lamotrigine derivative, the lamotrigine derivative having a chemical structure of Formula 1;

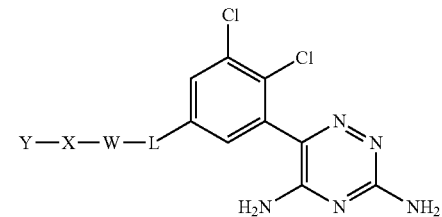

Formula 1 wherein:

L is NH;

W is $CO(CH_2)_2CONH(CH_2)_2$;

X is $NHCO(CH_2)_6$;

Y is $Y_1$—Z, wherein $Y_1$ is CO and Z is BSA or KLH; and the anti-lamotrigine antibody having at least one binding domain capable of binding lamotrigine, and wherein the antibody has a titer at least 1:100,000.

5. The polyclonal or monoclonal antibody composition as in claim 4, wherein the antibody is a monoclonal antibody.

6. The polyclonal or monoclonal antibody composition as in claim 4, wherein the antibody is a polyclonal antibody.

7. A method for producing an anti-lamotrigine antibody, comprising:

administering at least a first dose of an immunogenic composition including a lamotrigine derivative to an antibody producing subject, the lamotrigine derivative having a chemical structure of Formula;

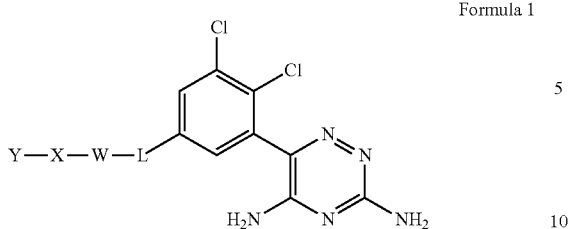

Formula 1 wherein:
L is NH;
W is $CO(CH_2)_2CONH(CH_2)_2$;
X is $NHCO(CH_2)_6$;
Y is $Y_1$-Z, wherein $Y_1$ CO and Z is BSA or KLH; and
collecting the antibodies from the antibody producing subject; and
purifying and/or screening the antibodies collected from the antibody producing subject.

8. The method of claim 7, further comprising administering to the antibody producing subject at least a second dose of the immunogenic composition prior to collecting the antibody from the antibody producing subject.

9. The method of claim 7, wherein the collecting includes at least one of obtaining blood, serum, plasma, or other biological sample from the antibody producing subject.

10. The method of claim 7, wherein the screening includes and ELISA assay.

* * * * *